US010584348B2

(12) United States Patent
Kondo et al.

(10) Patent No.: US 10,584,348 B2
(45) Date of Patent: Mar. 10, 2020

(54) PLANT IN WHICH EXPRESSION OF A CLATHRIN AND/OR COATOMER SUBUNIT IS SUPPRESSED OR INHIBITED, A METHOD FOR INCREASING THE PRODUCTION OF PLANT BIOMASS AND A METHOD FOR PRODUCING A PLANT

(71) Applicant: TOYOTA JIDOSHA KABUSHIKI KAISHA, Toyota-shi (JP)

(72) Inventors: Satoshi Kondo, Miyoshi (JP); Chikara Ohto, Toyota (JP); Hiroki Sugimoto, Nagakute (JP); Nobuhiko Muramoto, Nagakute (JP); Tomoko Tanaka, Nagakute (JP); Norihiro Mitsukawa, Nagakute (JP); Ritsuko Yogo, Nagakute (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 162 days.

(21) Appl. No.: 14/700,763

(22) Filed: Apr. 30, 2015

(65) Prior Publication Data

US 2015/0329871 A1 Nov. 19, 2015

(30) Foreign Application Priority Data

May 15, 2014 (JP) ................................. 2014-101407

(51) Int. Cl.
*C12N 15/82* (2006.01)

(52) U.S. Cl.
CPC ..... *C12N 15/8261* (2013.01); *C12N 15/8218* (2013.01); *Y02A 40/146* (2018.01)

(58) Field of Classification Search
None
See application file for complete search history.

(56) References Cited

U.S. PATENT DOCUMENTS

| 7,214,786 B2 | 5/2007 | Kovalic et al. |
| 7,569,389 B2 | 8/2009 | Feldmann et al. |
| 7,834,146 B2 | 11/2010 | Kovalic et al. |
| 8,299,318 B2 | 10/2012 | Brover et al. |
| 2004/0216190 A1* | 10/2004 | Kovalic ................. C07H 21/04 800/289 |
| 2006/0150283 A1* | 7/2006 | Alexandrov ......... C07K 14/415 800/288 |
| 2007/0079400 A1* | 4/2007 | Allen .................... C07K 14/415 800/287 |
| 2009/0094717 A1* | 4/2009 | Troukhan ............. C07K 14/415 800/290 |

FOREIGN PATENT DOCUMENTS

WO 2009/037279 A1 3/2009

OTHER PUBLICATIONS

Whisstock & Lesk, Q Rev Biophys. 36(3):307-40 (2003).*
Van Camp, Curr Opin Biotech 16:147-53 (2005).*
Tittonell et al., Agric Ecosys & Environ 105:213-20 (2005).*
Arabidopsis eFP Browser_At3g09800_2016.*
Fuji et al., Plant Physiol 172(2):211-19 (2015).*
At3g09800_www.arabidopsis.org_2016.*
At4g08520_www.arabidopsis.org_2016.*
Fourgoux-Nicol et al., Plant Mol Biol 40:857-72 (1999).*
The Plant List, *Brassicaceae*, accessed May 5, 2017.*
NCBI Blast SAH 1 At4g13940 v SAH 2 At3g23810, accessed May 8, 2017.*
Rocha et al., Plant Cell 17:404-17 (2005).*
Davies, Nutr Rev 61(6):S124-34 (2003).*
H. Tahara et al., "Clathrin is involved in organization of mitotic spindle and phragmoplast as well as in endocytosis in tobacco cell cultures", Protoplasma, Mar. 13, 2007, p. 230:1-11.
Mats X Andersson et al., "A chloroplast-localized vesicular transport system: a bio-informatics approach", BMC Genomics, Jul. 5, 2004, p. 5:40.
Salanoubat et al., "*Arabidopsis thaliana* coatomer subunit zeta-2 mRNA, complete cds", Accession No. NM_111815, retrieved from https://www.ncbi.nlm.nih.gov/nuccore/NM_111815.4 on Sep. 5, 2017.
Mayer et al., "*Arabidopsis thaliana* putative coatomer subunit zeta-3 mRNA, complete cds", Accession No. NM_116921, retrieved from https://www.ncbi.nlm.nih.gov/nuccore/NM_116921.4 on Sep. 5, 2017.

* cited by examiner

*Primary Examiner* — Russell T Boggs
(74) *Attorney, Agent, or Firm* — Sughrue Mion, PLLC

(57) ABSTRACT

This invention is intended to increase biomass production through suppression of expression of a gene functioning in relation to intracellular vesicular transport or inhibition of functions of a protein encoded by such gene. To this end, expression of a gene encoding the coatomer adapter zeta subunit is suppressed, the coatomer adapter zeta subunit is inhibited, expression of a gene encoding the clathrin adaptor small (sigma) subunit is suppressed, or the clathrin adaptor small (sigma) subunit is inhibited.

2 Claims, 4 Drawing Sheets

Specification includes a Sequence Listing.

US 10,584,348 B2

PLANT IN WHICH EXPRESSION OF A CLATHRIN AND/OR COATOMER SUBUNIT IS SUPPRESSED OR INHIBITED, A METHOD FOR INCREASING THE PRODUCTION OF PLANT BIOMASS AND A METHOD FOR PRODUCING A PLANT

TECHNICAL FIELD

The present invention relates to a plant in which expression of a given gene is suppressed, a method for increasing biomass production by suppressing the expression of such gene, and a method for producing a plant capable of producing increased biomass.

BACKGROUND ART

The term "biomass" generally refers to a total amount of organisms that inhabit or exist in a given area. When such term is used with regard to plants, in particular, it refers to dry weight per unit area. Biomass units are quantified in terms of mass or energy. The expression "biomass" is synonymous with "seibutsutairyo" or "seibutsuryo." In the case of plant biomass, the term "standing crop" is occasionally used for "biomass." Since plant biomass is generated by fixing atmospheric carbon dioxide with the use of solar energy, it can be regarded as so-called "carbon-neutral energy." Accordingly, an increase in plant biomass is effective for the preservation of the global environment, the prevention of global warming, and mitigation of greenhouse gas emissions. Thus, technologies for increasing the production of plant biomass have been industrially significant.

Plants are cultivated for the purpose of using some tissues thereof (e.g., seeds, roots, leaves, or stems) or for the purpose of producing various materials, such as fats and oils. Examples of fats and oils produced from plants that have heretofore been known include soybean oil, sesame oil, olive oil, coconut oil, rice oil, cottonseed oil, sunflower oil, corn oil, safflower oil, palm oil, and rapeseed oil. Such fats and oils are extensively used for household and industrial applications. Also, fats and oils produced from plants are used for biodiesel fuel or bioplastic raw materials, and the applicability thereof for alternative energy to petroleum is increasing.

In particular, an energy crop such as sugarcane can be used as a raw material for biofuel. Thus, the increased production of the total mass of a plant itself (the amount of plant biomass) is expected. Under such circumstances, improvement in productivity per unit of cultivation area is required in order to increase the amount of plant biomass production. It has been found that, if the number of cultivated plants is assumed to be constant per unit of cultivation area, improvement in the amount of biomass per plant would be necessary.

However, it is considered that, since many genes are related to the amount of plant biomass (a so-called "kind of quantitative trait"), individual gene introduction, deletion, or modification is insufficient for effectively increasing the production of plant biomass. For example, U.S. Pat. No. 7,834,146 discloses a technique comprising introducing one or more polypeptides selected from among approximately 180 exemplified polypeptides into a plant (i.e., activation), thereby improving the efficiency of a plant in terms of nitrogen use and increasing biomass production. Such approximately 180 kinds of polypeptides contain clathrin-associated protein complex small subunits (yeast AP-2; Yjr058c). However, there has been no disclosure of evidence demonstrating the effects of the clathrin-associated protein complex small subunits for increasing biomass production.

Vesicular transport is a mechanism for intracellular or extracellular transportation of a substance through a vesicle. A wide variety of substances, including proteins and lipids, are transported through vesicles. In general, it is known that inhibition of intracellular vesicular transport leads to an increase in the size of a cell, although the biomass amount is small (Tahara et al., 2007, Clathrin is involved in organization of mitotic spindle and phragmoplast as well as in endocytosis in tobacco cell cultures, Protoplasma, 230: 1-11). Also, Andersson, M. X. and Sandelius, A. S., 2004, A chloroplast-localized vesicular transport system: A Bioinformatics Approach, BMC Genomics, 5: 40 describes that proteins associated with transportation to the chloroplast thylakoid membrane can be predicted via bioinformatics analysis, and it lists genomic homologs of *Arabidopsis thaliana* associated with proteins associated with membrane transportation in yeast identified via homology analysis. According to Andersson, M. X. and Sandelius, A. S., 2004, A chloroplast-localized vesicular transport system: A Bioinformatics Approach, BMC Genomics, 5: 40, proteins homologous to yeast Ret3 are At3g09800 and At4g08520 of *Arabidopsis thaliana*.

No plants derived from *Arabidopsis thaliana* through At3g09800 overexpression or deletion have been known. However, U.S. Pat. Nos. 7,834,146, 7,214,786, 8,299,318, 7,569,389, and WO 2009/037,279 disclose that biomass production can be increased through overexpression of a gene encoding a protein having, for example, approximately 70% or higher sequence similarity to a protein encoded by At3g09800.

DISCLOSURE OF THE INVENTION

Objects to be Attained by the Invention

It was not known whether or not biomass production would be increased by suppressing expression of a gene functioning in relation to intracellular vesicular transport or inhibiting functions of a protein encoded by such gene. Accordingly, the present invention is intended to provide a plant capable of producing increased biomass through suppression of expression of a gene functioning in relation to intracellular vesicular transport or inhibition of functions of a protein encoded by such gene, a method for increasing biomass production, and a method for producing a plant capable of producing increased biomass.

Means for Attaining the Objects

The present inventors have conducted concentrated studies in order to attain the objects described above. As a result, they discovered that biomass production would be increased by suppressing a particular gene that functions in relation to vesicular transport in a plant cell. This has led to the completion of the present invention.

The present invention includes the following.
(1) A plant in which expression of a gene encoding the coatomer adapter zeta subunit is suppressed or the coatomer adapter zeta subunit is inhibited, or in which expression of a gene encoding the clathrin adaptor small (sigma) subunit is suppressed or the clathrin adaptor small (sigma) subunit is inhibited.
(2) The plant according to (1), wherein the gene encodes any of proteins (a) to (c) below:

(a) a protein comprising the amino acid sequence as shown in SEQ ID NO: 2 or 4;

(b) a protein comprising an amino acid sequence having 60% or higher sequence similarity to the amino acid sequence as shown in SEQ ID NO: 2 or 4 and functioning as the coatomer adapter zeta subunit or the clathrin adaptor small (sigma) subunit; or (c) a protein encoded by a polynucleotide hybridizing under stringent conditions to a polynucleotide comprising a nucleotide sequence complementary to the nucleotide sequence as shown in SEQ ID NO: 1 or 3 and functioning as the coatomer adapter zeta subunit or the clathrin adaptor small (sigma) subunit.

(3) The plant according to (1), wherein the gene encodes a protein comprising an amino acid sequence as shown in any of even-numbered sequences of SEQ ID NOs: 1 to 62 or comprising a nucleotide sequence as shown in any of odd-numbered sequences of SEQ ID NOs: 1 to 62.

(4) The plant according to (1), wherein the gene expression is suppressed by RNA interference.

(5) A method for increasing the production of plant biomass comprising suppressing expression of a gene encoding the coatomer adapter zeta subunit or inhibiting the coatomer adapter zeta subunit, or comprising suppressing expression of a gene encoding the clathrin adaptor small (sigma) subunit or inhibiting the clathrin adaptor small (sigma) subunit in a plant.

(6) The method according to (5), wherein the gene encodes any of proteins (a) to (c) below:

(a) a protein comprising the amino acid sequence as shown in SEQ ID NO: 2 or 4;

(b) a protein comprising an amino acid sequence having 60% or higher sequence similarity to the amino acid sequence as shown in SEQ ID NO: 2 or 4 and functioning as the coatomer adapter zeta subunit or the clathrin adaptor small (sigma) subunit; or (c) a protein encoded by a polynucleotide hybridizing under stringent conditions to a polynucleotide comprising a nucleotide sequence complementary to the nucleotide sequence as shown in SEQ ID NO: 1 or 3 and functioning as the coatomer adapter zeta subunit or the clathrin adaptor small (sigma) subunit.

(7) The method according to (5), wherein the gene encodes a protein comprising an amino acid sequence as shown in any of even-numbered sequences of SEQ ID NOs: 1 to 62 or comprising a nucleotide sequence as shown in any of odd-numbered sequences of SEQ ID NOs: 1 to 62.

(8) The method according to (5), wherein the gene expression is suppressed by RNA interference.

(9) A method for producing a plant comprising:

a step of suppressing expression of a gene encoding the coatomer adapter zeta subunit or inhibiting the coatomer adapter zeta subunit, or a step of suppressing expression of a gene encoding the clathrin adaptor small (sigma) subunit or inhibiting the clathrin adaptor small (sigma) subunit in a plant; and a subsequent step of measuring the amount of biomass produced by a progeny plant and selecting a plant line exhibiting significantly increased biomass production.

(10) The method according to (9), wherein the gene encodes any of proteins (a) to (c) below:

(a) a protein comprising the amino acid sequence as shown in SEQ ID NO: 2 or 4;

(b) a protein comprising an amino acid sequence having 60% or higher sequence similarity to the amino acid sequence as shown in SEQ ID NO: 2 or 4 and functioning as the coatomer adapter zeta subunit or the clathrin adaptor small (sigma) subunit; and (c) a protein encoded by a polynucleotide hybridizing under stringent conditions to a polynucleotide comprising a nucleotide sequence complementary to the nucleotide sequence as shown in SEQ ID NO: 1 or 3 and functioning as the coatomer adapter zeta subunit or the clathrin adaptor small (sigma) subunit.

(11) The method according to (9), wherein the gene encodes a protein comprising an amino acid sequence as shown in any of even-numbered sequences of SEQ ID NOs: 1 to 62 or comprising a nucleotide sequence as shown in any of odd-numbered sequences of SEQ ID NOs: 1 to 62.

(12) The method according to (9), wherein the gene expression is suppressed by RNA interference.

Effects of the Invention

According to the present invention, plant biomass production can be increased by suppressing a particular gene that functions in relation to vesicular transport in a plant cell, and a plant capable of producing a sufficient amount of biomass can be produced.

BEST MODE FOR CARRYING OUT THE INVENTION

Figure 1:
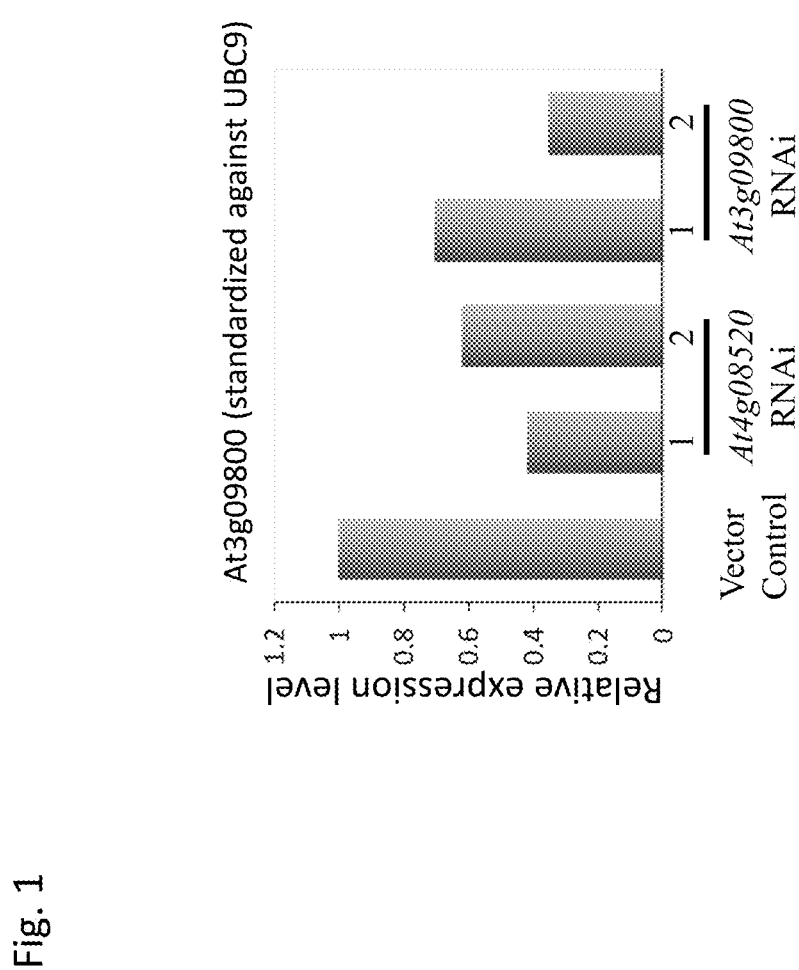
FIG. 1 shows a characteristic diagram showing the results of real-time PCR analysis of the At3g09800 gene expression level in a transformant.

Hereafter, the present invention is described in detail.

The plant according to the present invention is capable of producing increased biomass through suppression of expression of a gene functioning in relation to intracellular vesicular transport and/or inhibition of functions of a protein encoded by such gene. More specifically, the term "a gene that functions in relation to vesicular transport" refers to either or both a gene that encodes the coatomer adapter zeta subunit (ζ-COP) and a gene that encodes the clathrin adaptor small (sigma) subunit. When a plant is capable of producing increased biomass, the amount of biomass produced by such plant is significantly greater than the amount produced by wild-type plants comprising the genes as described above.

Expression of the gene described above may be suppressed or functions of a protein encoded by such gene may be inhibited in the whole plant or at least some plant tissues. The term "plant tissues" used herein refers to a plant organ, such as a leaf, stem, seed, root, or flower.

When expression of a gene is to be suppressed in the present invention, such gene is deleted, or the expression level of such gene is suppressed or lowered. Deletion of a gene is elimination of a part or the entire coding region of the gene from the chromosome or destruction of the gene through incorporation of a transposon or the like into a coding region of the gene. The gene expression level can be lowered by any means without particular limitation. For example, the gene expression control region may be modified to lower the transcription level, or the gene transcript may be selectively degraded.

Examples of techniques for gene suppression that can be employed in the present invention include the transposon technique, the transgene technique, the post-transcriptional gene silencing technique, the RNAi technique, the nonsense mediated decay (NMD) technique, the ribozyme technique, antisense technique, the micro-RNA (miRNA) technique, the small interfering RNA (siRNA) technique, the co-suppression technique, the zinc finger nuclease (ZFN) technique, the transcription activator-like effector (TALE) nuclease technique, and the clustered regularly interspaced short palindromic repeat (CRISPR) technique.

When a protein encoded by the coatomer adapter zeta subunit gene is inhibited from functioning, such protein is inhibited from functioning as the coatomer adapter complex. When a protein encoded by the gene of the clathrin adaptor small (sigma) subunit is inhibited from functioning, such protein is inhibited from functioning as the clathrin adaptor complex. Specific examples of techniques include expression of an antibody recognizing such protein as an antigen and expression of a protein having antagonistic activity against such protein.

A gene encoding the coatomer adapter zeta subunit (ζ-COP) and a gene encoding the clathrin adaptor small (sigma) subunit can be identified as endogenous genes in various plants. For example, a gene encoding the coatomer adapter zeta subunit (ζ-COP) and a gene encoding the clathrin adaptor small (sigma) subunit of *Arabidopsis thaliana* are known as At3g09800 and At4g08520, respectively.

The nucleotide sequence of the gene identified as At3g09800 and the amino acid sequence of a protein encoded by such gene are shown in SEQ ID NOs: 1 and 2, respectively. The nucleotide sequence of the gene identified as At4g08520 and the amino acid sequence of a protein encoded by such gene are shown in SEQ ID NOs: 3 and 4, respectively.

A gene encoding the coatomer adapter zeta subunit (ζ-COP) and a gene encoding the clathrin adaptor small (sigma) subunit, the expression of which are to be suppressed, are not limited to At3g09800 identified with SEQ ID NOs: 1 and 2 and At4g08520 identified with SEQ ID NOs: 3 and 4. That is, expression of a homologous gene endogenous in *Arabidopsis thaliana* or a homologous gene endogenous in a plant other than *Arabidopsis thaliana* may be suppressed. Such homologous genes are not particularly limited, and they can be identified by searching a database containing gene sequences of various organisms. Specifically, the DDBJ/EMBL/GenBank International Nucleotide Sequence Database or the SWISS-PROT database is searched, for example, using the nucleotide sequences and the amino acid sequences as shown in SEQ ID NOs: 1 to 4 as query sequences, so that the sequences can be easily searched for in such a known database and identified.

The term "homologous gene" generally refers to a gene that has branched off from a common ancestor gene through evolution, including a homologous gene (ortholog) of 2 types of species and a homologous gene (paralog) generated by overlapping branching that takes place within the same species. In other words, the term "homologous gene" refers to a homologous gene such as an ortholog or a paralog.

Table 1 shows homologous genes endogenous in *Arabidopsis thaliana* and homologous genes in plants other than *Arabidopsis thaliana*. Table 1 also shows yeast homologous genes. In addition, sequence numbers of nucleotide sequences of homologous genes and amino acid sequences of proteins encoded by the homologous genes are shown in Table 1.

TABLE 1

| Origin | Gene | Nucleotide sequence | Amino acid sequence |
|---|---|---|---|
| *Arabidopsis thaliana* | At4g08520 | SEQ ID NO: 3 | SEQ ID NO: 4 |
| *Arabidopsis thaliana* | At3g09800 | SEQ ID NO: 1 | SEQ ID NO: 2 |
| *Arabidopsis thaliana* | At1g60970 | SEQ ID NO: 5 | SEQ ID NO: 6 |
| *Arabidopsis thaliana* | At1g15370 | SEQ ID NO: 7 | SEQ ID NO: 8 |
| *Arabidopsis thaliana* | At1g47830 | SEQ ID NO: 9 | SEQ ID NO: 10 |
| *Arabidopsis thaliana* | At2g17380 | SEQ ID NO: 11 | SEQ ID NO: 12 |
| *Arabidopsis thaliana* | At2g19790 | SEQ ID NO: 13 | SEQ ID NO: 14 |
| *Arabidopsis thaliana* | At3g50860 | SEQ ID NO: 15 | SEQ ID NO: 16 |
| *Arabidopsis thaliana* | At4g35410 | SEQ ID NO: 17 | SEQ ID NO: 18 |
| Poplar | ABK92638(*Populus trichocarpa*) | SEQ ID NO: 19 | SEQ ID NO: 20 |
| *Picea sitchensis* | ABR17033(*Picea sitchensis*) | SEQ ID NO: 21 | SEQ ID NO: 22 |
| Corn | ACG48704(*Zea mays*) | SEQ ID NO: 23 | SEQ ID NO: 24 |
| Corn | ACN27243(*Zea mays*) | SEQ ID NO: 25 | SEQ ID NO: 26 |
| Bird's foot trefoil | AFK49535(*Lotus japonicus*) | SEQ ID NO: 27 | SEQ ID NO: 28 |
| *Brassica rapa* | BAA92778(*Brassica rapa*) | SEQ ID NO: 29 | SEQ ID NO: 30 |
| Barley | BAK05989(*Hordeum Vulgare*) | SEQ ID NO: 31 | SEQ ID NO: 32 |
| *Medicago truncatula* | CAI29266(*Medicago truncatula*) | SEQ ID NO: 33 | SEQ ID NO: 34 |
| *Chlorella* | EFN57218(*Chlorella variabilis*) | SEQ ID NO: 35 | SEQ ID NO: 36 |
| Coccomyxaceae | EIE23550(*Coccomyxa subellipsoidea*) | SEQ ID NO: 37 | SEQ ID NO: 38 |
| Rice | NP_001046672(*Oryza sativa*)Os02g0317400 | SEQ ID NO: 39 | SEQ ID NO: 40 |
| Tomato | NP_001233898(*Solanum lycopersicum*) | SEQ ID NO: 41 | SEQ ID NO: 42 |
| Tomato | NP_001233904(*Solanum lycopersicum*) | SEQ ID NO: 43 | SEQ ID NO: 44 |
| Soybean | NP_001236887(*Glycine max*) | SEQ ID NO: 45 | SEQ ID NO: 46 |
| *Chlamydomonas* | XP_001701294(*Chlamydomonas reinhardtii*) | SEQ ID NO: 47 | SEQ ID NO: 48 |
| *Physcomitrella patens* | XP_001753235(*Physcomitrella patens*) | SEQ ID NO: 49 | SEQ ID NO: 50 |
| Grape | XP_002277175(*Vitis vinifera*) | SEQ ID NO: 51 | SEQ ID NO: 52 |
| *Arabidopsis lyrata* | XP_002872400(*Arabidopsis lyrata*) | SEQ ID NO: 53 | SEQ ID NO: 54 |
| *Volvox* | XP_002958079(*Volvox carteri*) | SEQ ID NO: 55 | SEQ ID NO: 56 |
| *Selaginella moellendorffii* | XP_002975157(*Selaginella moellendorffii*) | SEQ ID NO: 57 | SEQ ID NO: 58 |
| Soybean | XP_003542071(*Glycine max*) | SEQ ID NO: 59 | SEQ ID NO: 60 |
| *Brachypodium distachyon* | XP_003564572(*Brachypodium distachyon*) | SEQ ID NO: 61 | SEQ ID NO: 62 |

TABLE 1-continued

| Origin | Gene | Nucleotide sequence | Amino acid sequence |
| --- | --- | --- | --- |
| Yeast | APS1(YLR170C) | SEQ ID NO: 63 | SEQ ID NO: 64 |
| Yeast | APS2(YJR058C) | SEQ ID NO: 65 | SEQ ID NO: 66 |
| Yeast | APS3(YJL024C) | SEQ ID NO: 67 | SEQ ID NO: 68 |
| Yeast | RET3(YPL010W) | SEQ ID NO: 69 | SEQ ID NO: 70 |

Genes listed in Table 1 encode proteins having 60% or higher sequence similarity to the amino acid sequence as shown in SEQ ID NO: 2 or 4, and such genes are highly likely to encode proteins having functions that are the same as those of the protein encoded by At3g09800 or At4g08520. Accordingly, the biomass produced by corresponding plants listed in Table 1 can be increased by suppressing expression of the genes listed in Table 1 or inhibiting proteins encoded by the genes listed in Table 1.

Sequence similarity is determined as a value indicating similarity between two amino acid sequences using sequence similarity search software such as Genetyx (Ver. 9), BLAST, PSI-BLAST, or HMMER in the default configuration.

Degrees of identity and sequence similarity of the homologous genes listed in Table 1 with At3g09800 and At4g08520 at the amino acid level are summarized in Table 2.

A gene to be suppressed in the plant according to the present invention as described above may encode a protein comprising an amino acid sequence exhibiting 60% or higher, preferably 70% or higher, more preferably 80% or higher, further preferably 90% or higher, and most preferably 95% or higher sequence similarity to the amino acid sequence as shown in SEQ ID NO: 2 or 4 and functioning as the coatomer adapter zeta subunit or the clathrin adaptor small (sigma) subunit. Alternatively, a gene to be suppressed in the plant according to the present invention as described above may encode a protein comprising an amino acid sequence exhibiting 60% or higher, preferably 70% or higher, more preferably 80% or higher, further preferably 90% or higher, and most preferably 95% or higher sequence identity to the amino acid sequence as shown in SEQ ID NO: 2 or 4 and functioning as the coatomer adapter zeta subunit or the clathrin adaptor small (sigma) subunit.

If a gene to be suppressed remains unknown as described above, a homologous gene of the plant according to the present invention may be identified in accordance with a conventional technique. When the plant genome information

TABLE 2

| | To At4g08520 | | To At3g09800 | |
| --- | --- | --- | --- | --- |
| Gene | Identity | Similarity | Identity | Similarity |
| At4g08520 | — | — | 93 | 100 |
| At3g09800 | 93 | 100 | — | — |
| At1g60970 | 74 | 96 | 75 | 96 |
| At1g15370 | 20 | 60 | 22 | 60 |
| At1g47830 | 22 | 60 | 22 | 65 |
| At2g17380 | 20 | 64 | 19 | 64 |
| At2g19790 | 23 | 68 | 21 | 66 |
| At3g50860 | 21 | 67 | 22 | 67 |
| At4g35410 | 21 | 67 | 20 | 67 |
| ABK92638(Populus trichocarpa) | 76 | 97 | 77 | 97 |
| ABR17033(Picea sitchensis) | 74 | 95 | 72 | 95 |
| ACG48704(Zea mays) | 73 | 95 | 74 | 94 |
| ACN27243(Zea mays) | 72 | 95 | 73 | 95 |
| AFK49535(Lotus japonicus) | 74 | 94 | 76 | 95 |
| BAA92778(Brassica rapa) | 94 | 100 | 96 | 100 |
| BAK05989(Hordeum Vulgare) | 69 | 94 | 69 | 93 |
| CAI29266(Medicago truncatula) | 74 | 94 | 75 | 94 |
| EFN57218(Chlorella variabilis) | 52 | 89 | 51 | 89 |
| EIE23550(Coccomyxa subellipsoidea) | 59 | 92 | 62 | 91 |
| NP_001046672(Oryza sativa)Os02g0317400 | 72 | 96 | 72 | 95 |
| NP_001233898(Solanum lycopersicum) | 77 | 97 | 76 | 96 |
| NP_001233904(Solanum lycopersicum) | 74 | 96 | 76 | 96 |
| NP_001236887(Glycine max) | 74 | 95 | 78 | 95 |
| XP_001701294(Chlamydomonas reinhardtii) | 55 | 90 | 56 | 90 |
| XP_001753235(Physcomitrella patens) | 70 | 94 | 69 | 94 |
| XP_002277175(Vitis vinifera) | 76 | 95 | 75 | 96 |
| XP_002872400(Arabidopsis lyrata) | 98 | 100 | 93 | 100 |
| XP_002958079(Volvox carteri) | 55 | 90 | 56 | 90 |
| XP_002975157(Selaginella moellendorffii) | 69 | 93 | 69 | 94 |
| XP_003542071(Glycine max) | 74 | 95 | 75 | 94 |
| XP_003564572(Brachypodium distachyon) | 73 | 93 | 73 | 93 |
| APS1(YLR170C) | 22 | 67 | 21 | 67 |
| APS2(YJR058C) | 14 | 65 | 15 | 65 |
| APS3(YJL024C) | 27 | 76 | 25 | 74 |
| RET3(YPL010W) | 29 | 78 | 29 | 78 | remains unknown, accordingly, a genome library or a cDNA library may be constructed in accordance with a conventional technique, hybridization may be carried out using the full length or a part of a nucleotide sequence complementary to the nucleotide sequence as shown in SEQ ID NO: 1 or 3 as a probe, and a gene to be suppressed can be identified. In other words, a homologous gene can be identified as a gene encoding a protein encoded by a polynucleotide hybridizing under stringent conditions to a polynucleotide comprising a nucleotide sequence complementary to the nucleotide sequence as shown in SEQ ID NO: 1 or 3 and functioning as the coatomer adapter zeta subunit or the clathrin adaptor small (sigma) subunit.

Under stringent conditions, namely, a specific hybrid is formed, but a non-specific hybrid is not formed. For example, such conditions comprise hybridization at 45° C. with 6×SSC (sodium chloride/sodium citrate), followed by washing at 50° C. to 65° C. with 0.2 to 1×SSC and 0.1% SDS. Alternatively, such conditions comprise hybridization at 65° C. to 70° C. with 1×SSC, followed by washing at 65° C. to 70° C. with 0.3×SSC. Hybridization can be performed by a conventional technique, such as a method described in J. Sambrook et al., Molecular Cloning; A Laboratory Manual, 2nd Ed., Cold Spring Harbor Laboratory, 1989.

Any plants can be modified without particular limitation. Examples of target plants include, but are not limited to, dicotyledons and monocotyledons, such as plants belonging to the families Brassicaceae, Gramineae, Solanaceae, Leguminosae, and Salicaceae (see below).

Family Brassicaceae: *Arabidopsis thaliana, Aburana* (rapeseed) (*Brassica rapa, Brassica napus*), cabbage (*Brassica oleracea* var. *capitata*), rapeseed (*Brassica rapa, Brassica napus*), ging-geng-cai (*Brassica rapa* var. *chinensis*), turnip (*Brassica rapa* var. *rapa*), coleseed greens (*Brassica rapa* var. *hakabura*), potherb mustard (*Brassica rapa* var. *lancinifolia*), komatsuna (*Brassica rapa* var. *peruviridis*), pak choi (*Brassica rapa* var. *chinensis*), Japanese radish (daikon) (*Brassica Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia, and the like.

Family Leguminosae: soy (*Glycine max*), pea (*Pisum sativum*), broad bean (*Vicia faba*), wisteria (*Wisteria floribunda*), peanut (*Arachis hypogaea*), bird's foot trefoil (*Lotus corniculatus* var. *japonicus*), common bean (*Phaseolus vulgaris*), azuki bean (*Vigna angularis*), Acacia, and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), copernicia, and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var. *gourda*), and the like.

Family Rosaceae: almond (*Amygdalus communis*), rose (*Rosa*), strawberry (*Fragaria*), cherry (*Prunus*), apple (*Malus pumila* var. *domestica*), and the like.

Family Caryophyllaceae: carnation (*Dianthus caryophyllus*) and the like.

Family Salicaceae: poplar (*Populus trichocarpa, Populus nigra, Populus tremula*) and the like.

Family Myrtaceae: eucalyptus (*Eucalyptus camaldulensis, Eucalyptus grandis*) and the like.

Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), miscanthus (Japanese silver grass) (*Miscanthus virgatum*), sorghum, switch grass (*Panicum*), and the like.

Family Liliaceae: tulip (*Tulipa*), lily (*Lilium*), and the like.

Production of monocotyledons capable of accumulating large quantities of soluble sugars is preferable. Among monocotyledons, it is particularly preferable that target plants be those belonging to the family Gramineae, such as rice, wheat, barley, sugarcane, and corn.

Other Steps and Techniques

Following the step of suppressing the gene expression or inhibiting functions of a protein encoded by such gene, a step of selecting an individual exhibiting an adequate phenotype from among plants can be carried out in accordance with a conventional technique. Selection methods are not particularly limited; a plant body or an arbitrary organ or tissue may be weighed and a plant that has produced a significantly greater amount of biomass than a wild-type plant may be selected.

In addition, a progeny plant can be produced from the resulting plant in accordance with a conventional technique. Specifically, a progeny plant that has produced a greater amount of biomass may be selected on the basis of the amount of biomass, and a stable plant line capable of producing a greater amount of biomass may be produced in accordance with the results of selection.

In addition, examples of the term "plant(s)" used in the present invention at least include grown plants, plant cells, plant tissues, calluses, and seeds. According to the present invention, specifically, any forms of plants that can be finally grown to mature plants are regarded as being "plants." Also, examples of plant cells include various forms of plant cells, such as suspended culture cells, protoplasts, and leaf sections. Plants can be obtained through the growth and differentiation of such plant cells. In addition, regeneration of plants from plant cells can be performed using a conventionally known method depending on plant cell type.

According to the present invention, as described above, a plant capable of producing a significantly greater amount of biomass per plant than the amounts produced by wild-type plants can be provided through suppression of expression of a relevant gene or inhibition of functions of a protein encoded by such a gene. When biomass production is significantly increased, the total weight of each plant is greater at the statistically significant level than that of a wild-type plant. In such a case, even when some plant tissues become particularly large and the sizes of the other tissues are equivalent to those of wild-type plants, it is concluded that the production of biomass is increased if the total weight of the entire plant is greater.

According to the present invention, the production of plant biomass is increased. Accordingly, productivity can be improved in both of the following cases: a case in which production of the whole plant is intended; and a case in which production of certain plant tissues (e.g., seeds) or components of a plant is intended. When production of fats and oils contained in plant seeds is intended, for example, the amounts of fats and oils that can be harvested per unit of area under cultivation can be improved to a great extent. Examples of fats and oils include, but are not particularly limited to, plant-derived fats and oils such as soybean oil, sesame oil, olive oil, coconut oil, rice oil, cottonseed oil, sunflower oil, corn oil, safflower oil, and rapeseed oil. Also, the fats and oils thus produced can be used for extensive applications, including household and industrial applications. In addition, such fats and oils can be used as raw materials for biodiesel fuel. According to the present invention, more specifically, fats and oils for household or industrial applications, biodiesel fuel, and the like can be produced at low cost with the use of plants in which expression of a relevant gene has been suppressed or functions of a protein encoded by such a gene have been inhibited.

EXAMPLES

Hereafter, the present invention is described in greater detail with reference to examples, although the technical scope of the present invention is not limited to the following examples.

Example 1

In this example, a transformant in which the At3g09800 or At4g08520 gene of *Arabidopsis thaliana* had been overexpressed and a transformant in which expression of the At3g09800 or At4g08520 gene had been suppressed were prepared, and the effects thereof for increasing biomass production were examined.
[Preparation of Construct]
In order to overexpress the At3g09800 or At4g08520 gene, pBI 35S:At3g09800 and pBI 35S:At4g08520 were prepared. At the outset, specifically, cDNA of *Arabidopsis thaliana* (Col-0) was amplified via PCR as a template with the use of primers (At3g09800: 5'-tccccgggtggtcagtcccttat-gtctcctgattcttgtcct-3' (SEQ ID NO: 71), 5'-ttgaac-gatcggggaaattcgagctctcatgtaagcagacttcttgc-3' (SEQ ID NO: 72), and 5'-ttggagagaacacgggggactctagaggatcccgggtggtca-gtc-3' (SEQ ID NO: 73); and At4g08520: 5'-tccccgggtggtca-gtcccttatggcagggactaatgattct-3' (SEQ ID NO: 74), 5'-ttgaac-gatcggggaaattcgagctcttatgtaagaagacttctcgc-3' (SEQ ID NO: 75), and 5'-ttggagagaacacgggggactctagaggatcccgggtggtca-gtc-3' (SEQ ID NO: 76)), and ORFs of At3g09800 and At4g08520 were isolated. These DNA fragments were cloned into the pBI121 vector cleaved with BamHI and SacI using the In-Fusion Dry-Down PCR Cloning Kit w/Cloning Enhancer (Clontech) (i.e., in-fusion reaction) to obtain pBI 35S:At3g09800 and pBI 35S:At4g08520.

In order to suppress expression of the At3g09800 or At4g08520 gene, in contrast, pBI 35SS:At3g09800RNAi and pBI 35SS:At4g08520RNAi were prepared. At the outset, specifically, cDNA of *Arabidopsis thaliana* (Col-0) was amplified via PCR as a template with the use of primers (At3g09800: 5'-atgtctcctgattcttgtcct-3' (SEQ ID NO: 77) and 5'-cacctcatgtaagcagacttcttgc-3' (SEQ ID NO: 78); and At4g08520: 5'-atggcagggactaatgattct-3' (SEQ ID NO: 79) and 5'-caccttatgtaagaagacttctcgc-3' (SEQ ID NO: 80)), and ORFs of At3g09800 and At4g08520 were isolated and cloned into the pENTR/D-TOPO vector using the pENTR Directional TOPO Cloning Kits (Invitrogen) (pENTR At3g09800 and pENTR At4g08520). ORFs of At3g09800 and At4g08520 of the vectors were cloned into pBI-sense and antisense-GW (INPLANTA INNOVATIONS INC) using the Gateway LR Clonase II Enzyme Mix (Invitrogen) (i.e., LR reactions) to obtain pBI 35SS:At3g09800RNAi and pBI 35SS:At4g08520RNAi.
[Preparation of Transformed *Arabidopsis thaliana* Plants]
The 4 types of vectors mentioned above were transformed into wild-type *Arabidopsis thaliana* (Col-0) plants by the floral-dip method (Clough and Bent, 1998). T1 plants were selected in MS medium containing kanamycin (final concentration: 30 mg/ml) and carbenicillin (final concentration: 100 mg/ml). The selected plants were then transplanted into a pot using Supermix A (Sakata Seed Corporation).
[Confirmation of Suppression of Gene Expression]

The transformed plants obtained above and the vector control plants were subjected to real-time PCR to analyze the expression levels of the At3g09800 and At4g08520 genes. T3 seeds of these transformed plants and the vector control plants were used.

At the outset, T3 seeds of each plant line were sowed in sucrose-free MS medium (prepared with the use of gellan gum; final concentration: 0.5%) and plants were subjected to vernalization for 3 days. Thereafter, all terrestrial parts of the plants grown for 23 to 26 days (including the period of vernalization) at 22° C. with a light period of 16 hours and a dark period of 8 hours were sampled (each pool consisting of two plants).

Subsequently, total RNAs were extracted from the sampled plants using the RNeasy Plant Mini Kit (QIAGEN) and the RNase-Free DNase Set (QIAGEN). cDNA was then synthesized from 2.0 μg of total RNA per 20 μl of a reaction solution using High-Capacity RNA-to-cDNA kit (ABI). Thereafter, real-time PCR was carried out using Power SYBR® Green PCR Master Mix (Applied Biosystems) in the composition shown in Table 3.

TABLE 3

| cDNA solution | 0.5 μL |
|---|---|
| PCR Masster Mix | 5.0 μL |
| Primer-F (3 μM) | 1.0 μL |
| Primer-R (3 μM) | 1.0 μL |
| dH$_2$0 | 2.5 μL |
| Total | 10.0 μL |

PCR and fluorescence detection were carried out using a 7000 Sequence Detection System (Applied Biosystems) under the conditions described below.

TABLE 4

| 50° C. 2 min | |
|---|---|
| 95° C. 10 min | |
| 95° C. 15 sec | ⎫ |
| 60 ° C. 1 min | ⎬ 40 cycles |
| 95° C. 15 sec | ⎭ |
| 60° C. 20 sec | |
| 95° C. 15 sec | |

The primers used for gene expression analysis are shown in Table 5.

TABLE 5

| At4g08520 | 5'-ggaaagtagcaatgcaaagcg-3' | (SEQ ID NO: 81) |
|---|---|---|
| | 5'-agatatggttggttacaagggct-3' | (SEQ ID NO: 82) |
| At3g09800 | 5'-ttcttgaaacggatccaaacgtc-3' | (SEQ ID NO: 83) |
| | 5'-attgtgtcgccatgatggaac-3' | (SEQ ID NO: 84) |

TABLE 5-continued

| At4g27960 | 5'-tcacaatttccaaggtgctgc-3' | (SEQ ID NO: 85) |
| (UBC9) | 5'-tcatctgggtttggatccgt-3' | (SEQ ID NO: 86) |

[Results]

Figure 2:
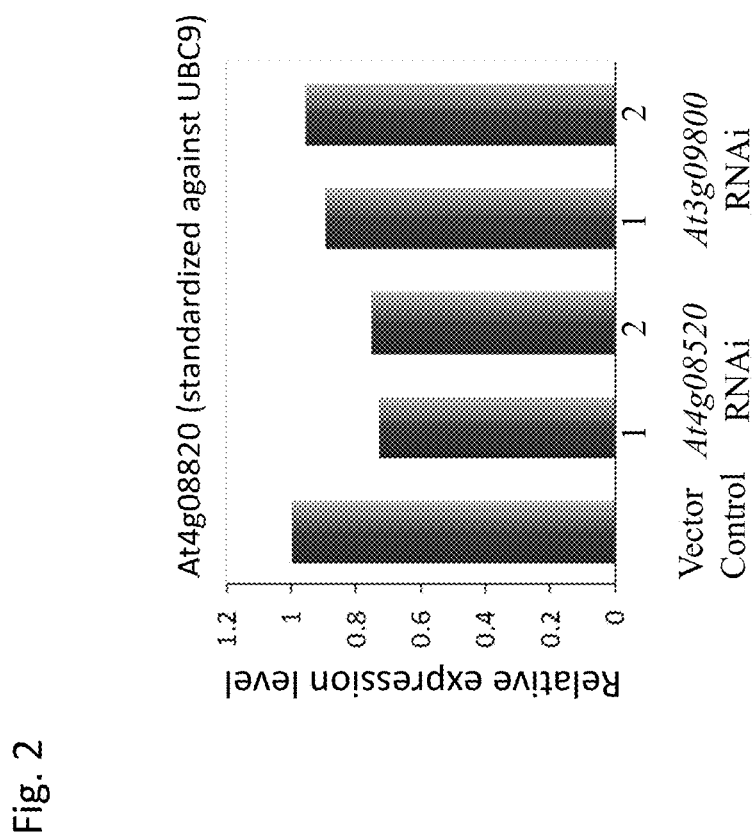
FIG. 2 shows a characteristic diagram showing the results of real-time PCR analysis of the At4g08520 gene expression level in a transformant.

FIG. 1 and FIG. 2 show the results of real-time PCR analysis of the At3g09800 and At4g08520 gene expression levels in the transformed plants into which pBI 35SS:At3g09800RNAi and pBI 35SS:At4g08520RNAi had been introduced, respectively, and the vector control plants. The At3g09800 and At4g08520 gene expression levels shown in FIG. 1 and FIG. 2 are standardized against the At4g27960 expression level. As is apparent from FIG. 1 and FIG. 2, the At3g09800 and At4g08520 gene expression levels were suppressed to a significant extent in the transformed plants compared with those in the vector control plants.

Figure 3:
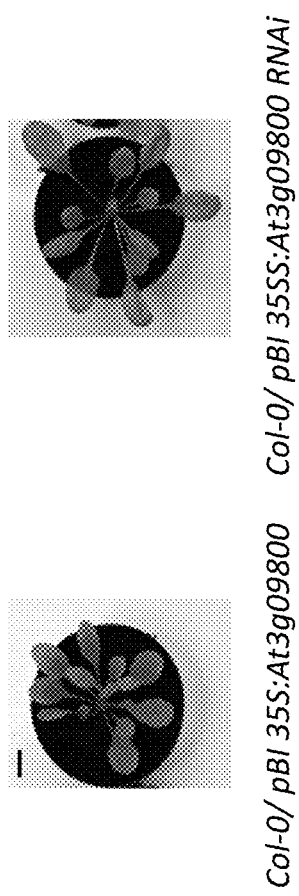
FIG. 3 shows a photograph showing a transformant in which the At3g09800 gene is overexpressed and the At3g09800 gene expression is suppressed.
Figure 4:
FIG. 4 shows a photograph showing a vector control line and a transformant in which the At3g09800 gene expression is suppressed.
Figure 4:
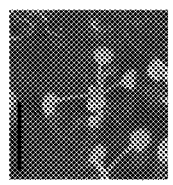

FIG. 3 shows a photograph of the transformed *Arabidopsis thaliana* plants into which pBI 35S:At3g09800 had been introduced and the transformed *Arabidopsis thaliana* plants into which pBI 35SS:At3g09800RNAi had been introduced. Also, FIG. 4 shows a photograph of the vector control plants and the transformed *Arabidopsis thaliana* plants into which pBI 35SS:At4g08520RNAi had been introduced. The photographs shown in FIG. 3 and FIG. 4 each show plants 12 days after transplantation (i.e., 36 days after sowing). The scale bars in FIG. 3 and FIG. 4 each indicate 10 mm. As shown in FIG. 3 and FIG. 4, the sizes of the At3g09800-overexpressing plants was substantially the same as those of the control plants into which pBI121 (35S:GUS) had been introduced. In contrast, the sizes of the transformed *Arabidopsis thaliana* plants into which pBI 35SS:At3g09800RNAi or pBI 35SS:At4g08520RNAi had been introduced were significantly greater than those of the control plants.

Accordingly, suppression of the At3g09800 or At4g08520 gene was found to lead to an increase in production of plant biomass.

The invention claimed is:

1. A method for producing a progeny plant comprising:
modifying a plant by suppressing expression of a gene encoding a coatomer adapter zeta subunit or inhibiting a coatomer adapter zeta subunit, or by suppressing expression of a gene encoding a clathrin adaptor small (sigma) subunit or inhibiting a clathrin adaptor small (sigma) subunit, wherein expression of the gene or activity of the coatomer adapter zeta subunit or the clathrin adaptor small (sigma) subunit is lower than that of a wild type plant as a result of said modifying;
measuring the amount of biomass produced by the modified plant, and selecting said modified plant based upon increased biomass production as compared to a wild type plant; and
producing a progeny plant from the selected modified plant, wherein said progeny plant exhibits increased biomass production as compared to a wild type plant, wherein the coatomer adapter zeta subunit is a protein comprising the amino acid sequence of SEQ ID NO: 30, and wherein the clathrin adaptor small (sigma) subunit is a protein comprising the amino acid sequence of SEQ ID NO: 54.

2. The method according to claim 1, wherein the suppression is accomplished by RNA interference.

* * * * *

SEQUENCE LISTING

<160> NUMBER OF SEQ ID NOS: 86

<210> SEQ ID NO 1
<211> LENGTH: 920
<212> TYPE: DNA
<213> ORGANISM: Arabidopsis thaliana
<220> FEATURE:
<221> NAME/KEY: CDS
<222> LOCATION: (165)..(704)

<400> SEQUENCE: 1

```
cagatcccga taagcagtgt gacactgaaa cagcgaaagg agctctctct cactccgagg     60
cgatttcttc tgtctcgacg atcttgcgct tttcacattt gaatcctcca atccattact    120
tcttctccga tctttattc cggtacatct caagtcttac aaca atg tct cct gat      176
                                                  Met Ser Pro Asp
                                                   1 tct tgt cct ttg gta aag aac att ctt ctt cta gac tct gaa gga aag     224
Ser Cys Pro Leu Val Lys Asn Ile Leu Leu Leu Asp Ser Glu Gly Lys
 5                  10                  15                  20 cgt gtg gct gtc aag tat tac tcg gat gac tgg cca act aat gcc gcc     272
Arg Val Ala Val Lys Tyr Tyr Ser Asp Asp Trp Pro Thr Asn Ala Ala
                 25                  30                  35 aag tta agt ttt gag aag tat gta ttc tca aag acc tct aag acc aat     320
Lys Leu Ser Phe Glu Lys Tyr Val Phe Ser Lys Thr Ser Lys Thr Asn
             40                  45                  50 gct cgt aca gaa gct gag atc aca ctg ttg gac agc aat att att gtc     368
Ala Arg Thr Glu Ala Glu Ile Thr Leu Leu Asp Ser Asn Ile Ile Val
         55                  60                  65 tat aag ttt gcc cag gac ctt cac ttc ttt gtt act gga ggt gaa aat     416
Tyr Lys Phe Ala Gln Asp Leu His Phe Phe Val Thr Gly Gly Glu Asn
     70                  75                  80 gaa aac gag ctc atc tta gct tct gtt ctt caa ggc ttt ttt gat gct     464
Glu Asn Glu Leu Ile Leu Ala Ser Val Leu Gln Gly Phe Phe Asp Ala
 85                  90                  95                 100 gtt gca ctt ctt ctg agg agc aat gtg gaa aag atg gaa gcc ctt gag     512
Val Ala Leu Leu Leu Arg Ser Asn Val Glu Lys Met Glu Ala Leu Glu
                105                 110                 115 aac ttg gat ctc atc ttt cta tgc ctt gat gaa atg gtc gat caa ggg     560
Asn Leu Asp Leu Ile Phe Leu Cys Leu Asp Glu Met Val Asp Gln Gly
            120                 125                 130
```

| | | | | | | | | | | | | | | | | |
|---|---|---|---|---|---|---|---|---|---|---|---|---|---|---|---|---|
| gtg | gtt | ctt | gaa | acg | gat | cca | aac | gtc | att | gcg | ggg | aaa | gta | gca | atg | 608 |
| Val | Val | Leu | Glu | Thr | Asp | Pro | Asn | Val | Ile | Ala | Gly | Lys | Val | Ala | Met | |
| | | 135 | | | | | 140 | | | | | 145 | | | | |
| cag | agc | aca | gaa | gct | agt | ggt | tca | ctc | tct | gaa | cag | aca | cta | aca | caa | 656 |
| Gln | Ser | Thr | Glu | Ala | Ser | Gly | Ser | Leu | Ser | Glu | Gln | Thr | Leu | Thr | Gln | |
| 150 | | | | | 155 | | | | | 160 | | | | | | |
| gcg | cta | gca | aca | gct | cgg | gag | cat | ctg | gca | aga | agt | ctg | ctt | aca | tga | 704 |
| Ala | Leu | Ala | Thr | Ala | Arg | Glu | His | Leu | Ala | Arg | Ser | Leu | Leu | Thr | | |
| 165 | | | | | 170 | | | | | 175 | | | | | | |

| | | |
|---|---|---|
| gttccatcat ggcgacacaa taatagaagc atggacttca atttctatgt tgagcaactt | 764 |
| tttattttg agtctttcgg tttgaaagtc tctaataatt gaattctgca aacaaactct | 824 |
| taaagtttgg tagtaaaggt ttgattatat atatagcttt gtgcaatgca tgaatgtttt | 884 |
| tggagagtgg aatttatta ctctaattga agtcta | 920 |

<210> SEQ ID NO 2
<211> LENGTH: 179
<212> TYPE: PRT
<213> ORGANISM: Arabidopsis thaliana

<400> SEQUENCE: 2

Met Ser Pro Asp Ser Cys Pro Leu Val Lys Asn Ile Leu Leu Asp
1               5                   10                  15

Ser Glu Gly Lys Arg Val Ala Val Lys Tyr Tyr Ser Asp Asp Trp Pro
            20                  25                  30

Thr Asn Ala Ala Lys Leu Ser Phe Glu Lys Tyr Val Phe Ser Lys Thr
        35                  40                  45

Ser Lys Thr Asn Ala Arg Thr Glu Ala Glu Ile Thr Leu Leu Asp Ser
    50                  55                  60

Asn Ile Ile Val Tyr Lys Phe Ala Gln Asp Leu His Phe Phe Val Thr
65                  70                  75                  80

Gly Gly Glu Asn Glu Asn Glu Leu Ile Leu Ala Ser Val Leu Gln Gly
                85                  90                  95

Phe Phe Asp Ala Val Ala Leu Leu Leu Arg Ser Asn Val Glu Lys Met
                100                 105                 110

Glu Ala Leu Glu Asn Leu Asp Leu Ile Phe Leu Cys Leu Asp Glu Met
            115                 120                 125

Val Asp Gln Gly Val Val Leu Glu Thr Asp Pro Asn Val Ile Ala Gly
        130                 135                 140

Lys Val Ala Met Gln Ser Thr Glu Ala Ser Gly Ser Leu Ser Glu Gln
145                 150                 155                 160

Thr Leu Thr Gln Ala Leu Ala Thr Ala Arg Glu His Leu Ala Arg Ser
                165                 170                 175

Leu Leu Thr

<210> SEQ ID NO 3
<211> LENGTH: 843
<212> TYPE: DNA
<213> ORGANISM: Arabidopsis thaliana
<220> FEATURE:
<221> NAME/KEY: CDS
<222> LOCATION: (63)..(608)

<400> SEQUENCE: 3

| | |
|---|---|
| gcaagctctc atcttcttca gctcaaaaag ccatctcaaa ggtatatttt gaatcaaaaa | 60 |

| | | | | | | | | | | | | | | | |
|---|---|---|---|---|---|---|---|---|---|---|---|---|---|---|---|
| ca | atg | gca | ggg | act | aat | gat | tct | tgt | cct | ttg | gta | aag | aac | att | ctt | 107 |
| | Met | Ala | Gly | Thr | Asn | Asp | Ser | Cys | Pro | Leu | Val | Lys | Asn | Ile | Leu | |
| | 1 | | | | 5 | | | | | 10 | | | | | 15 | |

```
ctt cta gac tct gaa gga aag cgt gtg gct gtc aag tat tac tcc gat       155
Leu Leu Asp Ser Glu Gly Lys Arg Val Ala Val Lys Tyr Tyr Ser Asp
             20                  25                  30 gat tgg gca act aat gct tcc aag tta gct ttt gaa aaa tat gtc ttc       203
Asp Trp Ala Thr Asn Ala Ser Lys Leu Ala Phe Glu Lys Tyr Val Phe
         35                  40                  45 tcg aaa acc tcc aag acc aat gct cgc aca gaa gct gag atc aca ctg       251
Ser Lys Thr Ser Lys Thr Asn Ala Arg Thr Glu Ala Glu Ile Thr Leu
     50                  55                  60 ttg gag agt aat att gtt gtc tat aag ttt gcc cag gac ctg cat ttc       299
Leu Glu Ser Asn Ile Val Val Tyr Lys Phe Ala Gln Asp Leu His Phe
 65                  70                  75 ttt gtt act gga ggt gaa aat gaa aac gag ctc gtc tta tca tct gtt       347
Phe Val Thr Gly Gly Glu Asn Glu Asn Glu Leu Val Leu Ser Ser Val
 80                  85                  90                  95 ctt caa ggc ttt ttt gat gct gtt gcg tta ctt ctg agg aac aat gtt       395
Leu Gln Gly Phe Phe Asp Ala Val Ala Leu Leu Leu Arg Asn Asn Val
                100                 105                 110 gaa aag atg gaa gcc ctt gaa aac ttg gat ctc atc ttt ttg tgc ctt       443
Glu Lys Met Glu Ala Leu Glu Asn Leu Asp Leu Ile Phe Leu Cys Leu
            115                 120                 125 gat gag atg gtt gat caa ggg atg gta ctt gaa aca gac gcg aat gtt       491
Asp Glu Met Val Asp Gln Gly Met Val Leu Glu Thr Asp Ala Asn Val
        130                 135                 140 att gcg ggg aaa gta gca atg caa agc gca gaa gca agt ggt tca ctc       539
Ile Ala Gly Lys Val Ala Met Gln Ser Ala Glu Ala Ser Gly Ser Leu
    145                 150                 155 tct gaa cag aca tta act caa gca ttg gca aca gct cgg gag cac ctt       587
Ser Glu Gln Thr Leu Thr Gln Ala Leu Ala Thr Ala Arg Glu His Leu
160                 165                 170                 175 gcg aga agt ctt ctt aca taa attttcatcg tgggagcgaa atgatatatt          638
Ala Arg Ser Leu Leu Thr
                180 cataagccct tgtaaccaac catatctgaa atggttaccc gttcactaga aatcaacccc    698 tattgactta actatctcat gactttgttt tcttatggtt ttttggtgga acttagatct    758 tttattcgcc tgttcttgcg gaaccatctt tttaaatgtg aggatcaaca ttgcactagt    818 gattgattgc tttacatatc taaga                                          843

<210> SEQ ID NO 4
<211> LENGTH: 181
<212> TYPE: PRT
<213> ORGANISM: Arabidopsis thaliana

<400> SEQUENCE: 4

Met Ala Gly Thr Asn Asp Ser Cys Pro Leu Val Lys Asn Ile Leu Leu
 1               5                  10                  15

Leu Asp Ser Glu Gly Lys Arg Val Ala Val Lys Tyr Tyr Ser Asp Asp
             20                  25                  30

Trp Ala Thr Asn Ala Ser Lys Leu Ala Phe Glu Lys Tyr Val Phe Ser
         35                  40                  45

Lys Thr Ser Lys Thr Asn Ala Arg Thr Glu Ala Glu Ile Thr Leu Leu
     50                  55                  60

Glu Ser Asn Ile Val Val Tyr Lys Phe Ala Gln Asp Leu His Phe Phe
 65                  70                  75                  80

Val Thr Gly Gly Glu Asn Glu Asn Glu Leu Val Leu Ser Ser Val Leu
                 85                  90                  95
```

```
Gln Gly Phe Phe Asp Ala Val Ala Leu Leu Arg Asn Asn Val Glu
                100                 105                 110
Lys Met Glu Ala Leu Glu Asn Leu Asp Leu Ile Phe Leu Cys Leu Asp
        115                 120                 125
Glu Met Val Asp Gln Gly Met Val Leu Glu Thr Asp Ala Asn Val Ile
130                 135                 140
Ala Gly Lys Val Ala Met Gln Ser Ala Glu Ala Ser Gly Ser Leu Ser
145                 150                 155                 160
Glu Gln Thr Leu Thr Gln Ala Leu Ala Thr Ala Arg Glu His Leu Ala
                165                 170                 175
Arg Ser Leu Leu Thr
            180

<210> SEQ ID NO 5
<211> LENGTH: 833
<212> TYPE: DNA
<213> ORGANISM: Arabidopsis thaliana
<220> FEATURE:
<221> NAME/KEY: CDS
<222> LOCATION: (140)..(673)

<400> SEQUENCE: 5
tagtaaaaga aaattaatat tcctgaaaat atgaatttgc caatttgtaa cgttttctga      60
aaatttcctc tgccaaagtc caaggagag ttttttcttta ttactagggc attctctgca    120
gatttcttct ccttaagcc atg gaa ttg ccc cca aaa gtg aaa aac atc ttg     172
              Met Glu Leu Pro Pro Lys Val Lys Asn Ile Leu
                1               5                  10 ctt ttg gat tct gaa gga aag cgt gta gcg gtt aag tat tac tca gat     220
Leu Leu Asp Ser Glu Gly Lys Arg Val Ala Val Lys Tyr Tyr Ser Asp
        15                  20                  25 gac tgg cca aca aat tca gct cag gaa gcg ttc gaa aaa tcc gtg ttt     268
Asp Trp Pro Thr Asn Ser Ala Gln Glu Ala Phe Glu Lys Ser Val Phe
        30                  35                  40 aca aag act cag aaa aca aat gct agg acc gaa gtg gaa gtg aca gca     316
Thr Lys Thr Gln Lys Thr Asn Ala Arg Thr Glu Val Glu Val Thr Ala
    45                  50                  55 ctg gag aac aac att gtt gtg tac aaa ttt gtg caa gat ctc cat ttc     364
Leu Glu Asn Asn Ile Val Val Tyr Lys Phe Val Gln Asp Leu His Phe
60                  65                  70                  75 ttt gtt acg ggc ggt gaa gag gaa aac gag ctt atc tta gcc agt gtg     412
Phe Val Thr Gly Gly Glu Glu Glu Asn Glu Leu Ile Leu Ala Ser Val
                80                  85                  90 ctt gag gga ctc ttt gat gca gtg acc ctt ctc ctt aga agc aat gtt     460
Leu Glu Gly Leu Phe Asp Ala Val Thr Leu Leu Leu Arg Ser Asn Val
            95                  100                 105 gat aag aga gag gca cta gac aac ctt gat ctc atc ttt cta agc ttt     508
Asp Lys Arg Glu Ala Leu Asp Asn Leu Asp Leu Ile Phe Leu Ser Phe
        110                 115                 120 gat gaa att atc gat ggc ggt att gtt ctg gag acg gat gca aat gta     556
Asp Glu Ile Ile Asp Gly Gly Ile Val Leu Glu Thr Asp Ala Asn Val
    125                 130                 135 ata gca ggt aaa gca ggg atc aat agc act gac cct aac gct cct cta     604
Ile Ala Gly Lys Ala Gly Ile Asn Ser Thr Asp Pro Asn Ala Pro Leu
140                 145                 150                 155 tcc gag cag acg ata agt caa gca ctc gcg act gca aga gaa cat ttg     652
Ser Glu Gln Thr Ile Ser Gln Ala Leu Ala Thr Ala Arg Glu His Leu
                160                 165                 170 aca agg tca ctt atg aaa tga tgtgtgtttt gctcttcggt aataatggtt        703
Thr Arg Ser Leu Met Lys
```

```
                        175 gtttttgtca tggtgaatgt gtgttttgtc tcttgtagtt gagtgactat actcttaaat    763 ataaaagtta ctttgcactt gggagatagt taccgttctt aaggtcaaac aattctctgg    823 tgatttcttc                                                           833

<210> SEQ ID NO 6
<211> LENGTH: 177
<212> TYPE: PRT
<213> ORGANISM: Arabidopsis thaliana

<400> SEQUENCE: 6

Met Glu Leu Pro Pro Lys Val Lys Asn Ile Leu Leu Leu Asp Ser Glu
1               5                   10                  15

Gly Lys Arg Val Ala Val Lys Tyr Tyr Ser Asp Asp Trp Pro Thr Asn
            20                  25                  30

Ser Ala Gln Glu Ala Phe Glu Lys Ser Val Phe Thr Lys Thr Gln Lys
        35                  40                  45

Thr Asn Ala Arg Thr Glu Val Glu Val Thr Ala Leu Glu Asn Asn Ile
    50                  55                  60

Val Val Tyr Lys Phe Val Gln Asp Leu His Phe Phe Val Thr Gly Gly
65                  70                  75                  80

Glu Glu Glu Asn Glu Leu Ile Leu Ala Ser Val Leu Glu Gly Leu Phe
                85                  90                  95

Asp Ala Val Thr Leu Leu Arg Ser Asn Val Asp Lys Arg Glu Ala
            100                 105                 110

Leu Asp Asn Leu Asp Leu Ile Phe Leu Ser Phe Asp Glu Ile Ile Asp
        115                 120                 125

Gly Gly Ile Val Leu Glu Thr Asp Ala Asn Val Ile Ala Gly Lys Ala
    130                 135                 140

Gly Ile Asn Ser Thr Asp Pro Asn Ala Pro Leu Ser Glu Gln Thr Ile
145                 150                 155                 160

Ser Gln Ala Leu Ala Thr Ala Arg Glu His Leu Thr Arg Ser Leu Met
                165                 170                 175

Lys

<210> SEQ ID NO 7
<211> LENGTH: 734
<212> TYPE: DNA
<213> ORGANISM: Arabidopsis thaliana
<220> FEATURE:
<221> NAME/KEY: CDS
<222> LOCATION: (89)..(532)

<400> SEQUENCE: 7
gagaatgttt tgaggtagag aggagaagta gaaatcgata aaggcgaaga aggaatcgca    60
aggaaggaag aaacttgaga ggaagatc atg atc cta gct gtg ttg ttc gcc    112
                                Met Ile Leu Ala Val Leu Phe Ala
                                1               5 aat tcc gtt ggg aat gtt tta atc gaa agg ttc aat gga gta cca gct    160
Asn Ser Val Gly Asn Val Leu Ile Glu Arg Phe Asn Gly Val Pro Ala
    10              15                  20 gag gaa cgg ctc cac tgg cga tct ttc ttg gtt aag ttg gga gca gat    208
Glu Glu Arg Leu His Trp Arg Ser Phe Leu Val Lys Leu Gly Ala Asp
25              30                  35                  40 aat ctc aaa ggc gtt aaa aat gag gag ctt ctc gtt gct tgc cac aag    256
Asn Leu Lys Gly Val Lys Asn Glu Glu Leu Leu Val Ala Cys His Lys
                45                  50                  55
```

-continued

| | | | | | | | | | | | | | | | | |
|---|---|---|---|---|---|---|---|---|---|---|---|---|---|---|---|---|
| tcg | gtt | tat | atc | gtg | tac | aca | atg | cta | ggg | gat | gtt | agc | atc | ttc | ctt | 304 |
| Ser | Val | Tyr | Ile | Val | Tyr | Thr | Met | Leu | Gly | Asp | Val | Ser | Ile | Phe | Leu | |
| | | | 60 | | | | | 65 | | | | | 70 | | | |
| gtt | ggc | aaa | gac | gag | tat | gat | gaa | ctt | gct | ttg | gca | gaa | acc | atc | tat | 352 |
| Val | Gly | Lys | Asp | Glu | Tyr | Asp | Glu | Leu | Ala | Leu | Ala | Glu | Thr | Ile | Tyr | |
| | | 75 | | | | | 80 | | | | | 85 | | | | |
| atc | ata | aca | gcg | gct | gtg | aaa | gac | gta | tgt | gga | aag | ccg | cct | aca | gag | 400 |
| Ile | Ile | Thr | Ala | Ala | Val | Lys | Asp | Val | Cys | Gly | Lys | Pro | Pro | Thr | Glu | |
| | 90 | | | | | 95 | | | | | 100 | | | | | |
| cga | gtg | ttt | ttg | gat | aaa | tat | gga | agg | att | tgc | ttg | tgc | ctt | gat | gaa | 448 |
| Arg | Val | Phe | Leu | Asp | Lys | Tyr | Gly | Arg | Ile | Cys | Leu | Cys | Leu | Asp | Glu | |
| 105 | | | | | 110 | | | | | 115 | | | | | 120 | |
| atc | gtt | tgg | aac | gga | ctt | ctg | gag | aac | acc | gac | aaa | gac | agg | atc | aag | 496 |
| Ile | Val | Trp | Asn | Gly | Leu | Leu | Glu | Asn | Thr | Asp | Lys | Asp | Arg | Ile | Lys | |
| | | | 125 | | | | | 130 | | | | | 135 | | | |
| cga | ctc | atc | aga | ttg | aaa | cct | cct | tct | gaa | gtt | tga | tatgctccaa | | | | 542 |
| Arg | Leu | Ile | Arg | Leu | Lys | Pro | Pro | Ser | Glu | Val | | | | | | |
| | | | 140 | | | | | 145 | | | | | | | | | ccaaccacac attcttcttc tactcatttt aagagctttc tcattctcca ccgattgttg      602 tttgttgaat cacttctcta tatcacatat tcaactatca actactgctg ttgttcgatc      662 agtccatctt gtagtgttgt tttttaaatc ttcagttttt agtgttacat aacaaagaac      722 aaatttctat cc      734

<210> SEQ ID NO 8
<211> LENGTH: 147
<212> TYPE: PRT
<213> ORGANISM: Arabidopsis thaliana

<400> SEQUENCE: 8

Met Ile Leu Ala Val Leu Phe Ala Asn Ser Val Gly Asn Val Leu Ile
1               5                   10                  15

Glu Arg Phe Asn Gly Val Pro Ala Glu Glu Arg Leu His Trp Arg Ser
            20                  25                  30

Phe Leu Val Lys Leu Gly Ala Asp Asn Leu Lys Gly Val Lys Asn Glu
        35                  40                  45

Glu Leu Leu Val Ala Cys His Lys Ser Val Tyr Ile Val Tyr Thr Met
    50                  55                  60

Leu Gly Asp Val Ser Ile Phe Leu Val Gly Lys Asp Glu Tyr Asp Glu
65                  70                  75                  80

Leu Ala Leu Ala Glu Thr Ile Tyr Ile Ile Thr Ala Ala Val Lys Asp
            85                  90                  95

Val Cys Gly Lys Pro Pro Thr Glu Arg Val Phe Leu Asp Lys Tyr Gly
        100                 105                 110

Arg Ile Cys Leu Cys Leu Asp Glu Ile Val Trp Asn Gly Leu Leu Glu
    115                 120                 125

Asn Thr Asp Lys Asp Arg Ile Lys Arg Leu Ile Arg Leu Lys Pro Pro
130                 135                 140

Ser Glu Val
145

<210> SEQ ID NO 9
<211> LENGTH: 819
<212> TYPE: DNA
<213> ORGANISM: Arabidopsis thaliana
<220> FEATURE:
<221> NAME/KEY: CDS
<222> LOCATION: (143)..(571)

<400> SEQUENCE: 9

```
tcttttgac tggatagttt ggctgcttta cgaacctgtt ttcaacaaag gtcgtgaaaa      60
ttcaaagtga gatctgaaag aagaaaattc ctctgatcgc tcacgatttc tcctgaattc     120
tccattagat tttgcagaga aa atg atc cga ttc ata tta ttg cag aac aga     172
                          Met Ile Arg Phe Ile Leu Leu Gln Asn Arg
                            1               5                  10 caa ggt aag act cgt cta gcc aaa tac tat gtc cct ctc gaa gaa tcc     220
Gln Gly Lys Thr Arg Leu Ala Lys Tyr Tyr Val Pro Leu Glu Glu Ser
             15                  20                  25 gag aaa cac aaa gtc gaa tac gag gtt cat aga tta gtg gtg aat cgc     268
Glu Lys His Lys Val Glu Tyr Glu Val His Arg Leu Val Val Asn Arg
         30                  35                  40 gac gcc aaa ttc acc aac ttc gtt gag ttt aga aca cac aag gtg ata     316
Asp Ala Lys Phe Thr Asn Phe Val Glu Phe Arg Thr His Lys Val Ile
             45                  50                  55 tac agg cgt tat gct gga ttg ttt ttc tct gtg tgc gtg gat ata acc     364
Tyr Arg Arg Tyr Ala Gly Leu Phe Phe Ser Val Cys Val Asp Ile Thr
 60                  65                  70 gac aat gag ttg gct tac ttg gag agt atc cat ttg ttt gtg gag ata     412
Asp Asn Glu Leu Ala Tyr Leu Glu Ser Ile His Leu Phe Val Glu Ile
 75                  80                  85                  90 ttg gac cat ttc ttc agc aat gtt tgt gag cta gat ttg gtg ttt aat     460
Leu Asp His Phe Phe Ser Asn Val Cys Glu Leu Asp Leu Val Phe Asn
                     95                 100                 105 ttc cac aag gtg tac ttg ata ctc gat gag ttc att ctt gct ggg gag     508
Phe His Lys Val Tyr Leu Ile Leu Asp Glu Phe Ile Leu Ala Gly Glu
                 110                 115                 120 ctc caa gaa aca agc aaa agg gca atc atc gaa agg atg tca gaa ctc     556
Leu Gln Glu Thr Ser Lys Arg Ala Ile Ile Glu Arg Met Ser Glu Leu
             125                 130                 135 gag aag cta cag tga tgacggttaa gaatcacatt ctacttggtt aactgcgtac     611
Glu Lys Leu Gln
     140 ctgccagatg tttcttggca tgttcagaga tttgctatac tttgttgagt tgttagacaa     671 tggtgtagcg tttacattgt gaatgaagaa tttagagtga ttctgctaaa gatctctcat     731 ccaacatttt gtttacctgt gagatttttca tttcaactag tgatgtacta tttgtttcgt     791 agaactatga taccacacat gctttgag                                        819
```

<210> SEQ ID NO 10
<211> LENGTH: 142
<212> TYPE: PRT
<213> ORGANISM: Arabidopsis thaliana

<400> SEQUENCE: 10

```
Met Ile Arg Phe Ile Leu Leu Gln Asn Arg Gln Gly Lys Thr Arg Leu
 1               5                  10                  15

Ala Lys Tyr Tyr Val Pro Leu Glu Glu Ser Glu Lys His Lys Val Glu
             20                  25                  30

Tyr Glu Val His Arg Leu Val Val Asn Arg Asp Ala Lys Phe Thr Asn
         35                  40                  45

Phe Val Glu Phe Arg Thr His Lys Val Ile Tyr Arg Arg Tyr Ala Gly
     50                  55                  60

Leu Phe Phe Ser Val Cys Val Asp Ile Thr Asp Asn Glu Leu Ala Tyr
 65                  70                  75                  80

Leu Glu Ser Ile His Leu Phe Val Glu Ile Leu Asp His Phe Phe Ser
```

```
                    85                  90                  95
Asn Val Cys Glu Leu Asp Leu Val Phe Asn Phe His Lys Val Tyr Leu
                100                 105                 110

Ile Leu Asp Glu Phe Ile Leu Ala Gly Glu Leu Gln Glu Thr Ser Lys
            115                 120                 125

Arg Ala Ile Ile Glu Arg Met Ser Glu Leu Glu Lys Leu Gln
        130                 135                 140

<210> SEQ ID NO 11
<211> LENGTH: 764
<212> TYPE: DNA
<213> ORGANISM: Arabidopsis thaliana
<220> FEATURE:
<221> NAME/KEY: CDS
<222> LOCATION: (121)..(606)

<400> SEQUENCE: 11
atccaacaaa cttatatgtg tatcggacac agaagaatac tttccacgat catcagcttc      60
tggagatctc ttctgggaat cgagcttcac tgttaaagat tttccttcaa tcggctaaaa     120 atg ata cat ttc gtg tta cta gtc agt cga caa ggg aaa gta agg ctc       168
Met Ile His Phe Val Leu Leu Val Ser Arg Gln Gly Lys Val Arg Leu
1               5                   10                  15 acc aag tgg tat tcg ccg tat acg cag aag gaa aga tct aag gtc ata       216
Thr Lys Trp Tyr Ser Pro Tyr Thr Gln Lys Glu Arg Ser Lys Val Ile
            20                  25                  30 cgt gaa ctc agt gga gtg att ctg aac cga ggt ccc aag ctc tgc aat       264
Arg Glu Leu Ser Gly Val Ile Leu Asn Arg Gly Pro Lys Leu Cys Asn
        35                  40                  45 ttt att gaa tgg aga gga tac aag gtt gtc tac aaa aga tat gca agc       312
Phe Ile Glu Trp Arg Gly Tyr Lys Val Val Tyr Lys Arg Tyr Ala Ser
    50                  55                  60 ttg tac ttc tgc atg tgc att gat gag gcg gat aac gag tta gag gta       360
Leu Tyr Phe Cys Met Cys Ile Asp Glu Ala Asp Asn Glu Leu Glu Val
65                  70                  75                  80 ctg gag ata att cat cac tac gtc gag att ctt gac cgc tac ttt ggc       408
Leu Glu Ile Ile His His Tyr Val Glu Ile Leu Asp Arg Tyr Phe Gly
                85                  90                  95 agt gtg tgt gaa ctc gat ttg att ttt aac ttc cac aag gcg tat tat       456
Ser Val Cys Glu Leu Asp Leu Ile Phe Asn Phe His Lys Ala Tyr Tyr
                100                 105                 110 ata ctc gat gag ctg ttg atc gcc gga gaa ctt caa gag tca agc aag       504
Ile Leu Asp Glu Leu Leu Ile Ala Gly Glu Leu Gln Glu Ser Ser Lys
            115                 120                 125 aaa aca gtt gca agg ata ata tca gcc cag gat caa ttg gtg gaa gtt       552
Lys Thr Val Ala Arg Ile Ile Ser Ala Gln Asp Gln Leu Val Glu Val
        130                 135                 140 gcg aaa gag gag gcg agt tcc ata agt aat ata att gct cag gct acc       600
Ala Lys Glu Glu Ala Ser Ser Ile Ser Asn Ile Ile Ala Gln Ala Thr
145                 150                 155                 160 aag tag tcctttctg aacttttctt atgcagctga acaatcgta aatgagttaa         656
Lys tattttcctt aaactctgag atattctctt ctgaatcaca cttttgtttg tcatgtcatg     716
tgattgtttg attgattaga agaaagaagc attcatcgtt ttgggttt                  764

<210> SEQ ID NO 12
<211> LENGTH: 161
<212> TYPE: PRT
<213> ORGANISM: Arabidopsis thaliana
```

<400> SEQUENCE: 12

```
Met Ile His Phe Val Leu Leu Val Ser Arg Gln Gly Lys Val Arg Leu
1               5                   10                  15

Thr Lys Trp Tyr Ser Pro Tyr Thr Gln Lys Glu Arg Ser Lys Val Ile
            20                  25                  30

Arg Glu Leu Ser Gly Val Ile Leu Asn Arg Gly Pro Lys Leu Cys Asn
        35                  40                  45

Phe Ile Glu Trp Arg Gly Tyr Lys Val Val Tyr Lys Arg Tyr Ala Ser
    50                  55                  60

Leu Tyr Phe Cys Met Cys Ile Asp Glu Ala Asp Asn Glu Leu Glu Val
65                  70                  75                  80

Leu Glu Ile Ile His His Tyr Val Glu Ile Leu Asp Arg Tyr Phe Gly
                85                  90                  95

Ser Val Cys Glu Leu Asp Leu Ile Phe Asn Phe His Lys Ala Tyr Tyr
            100                 105                 110

Ile Leu Asp Glu Leu Leu Ile Ala Gly Glu Leu Gln Glu Ser Ser Lys
        115                 120                 125

Lys Thr Val Ala Arg Ile Ile Ser Ala Gln Asp Gln Leu Val Glu Val
    130                 135                 140

Ala Lys Glu Glu Ala Ser Ser Ile Ser Asn Ile Ile Ala Gln Ala Thr
145                 150                 155                 160

Lys
```

<210> SEQ ID NO 13
<211> LENGTH: 641
<212> TYPE: DNA
<213> ORGANISM: Arabidopsis thaliana
<220> FEATURE:
<221> NAME/KEY: CDS
<222> LOCATION: (72)..(503)

<400> SEQUENCE: 13

```
aaaaagatct gaaagaaata aaaacgaat cggaagagag agagagagag agagattgga      60
gctagttgga g atg gga ata agg ttc ata ttg atg gtg aac aag caa ggc     110
            Met Gly Ile Arg Phe Ile Leu Met Val Asn Lys Gln Gly
              1               5                   10 cag act cgt ctt gct cag tac tac gaa tgg ctc act ctc gag gaa cgt     158
Gln Thr Arg Leu Ala Gln Tyr Tyr Glu Trp Leu Thr Leu Glu Glu Arg
         15                  20                  25 cgc gct ctc gaa ggc gaa atc gtc cgt aaa tgc ctc gct cgc aac gac     206
Arg Ala Leu Glu Gly Glu Ile Val Arg Lys Cys Leu Ala Arg Asn Asp
 30                  35                  40                  45 caa cag tgt tcg ttt gtc gag cat cgc aac tac aag ata gtc tac agg     254
Gln Gln Cys Ser Phe Val Glu His Arg Asn Tyr Lys Ile Val Tyr Arg
                 50                  55                  60 cgt tac gca tct ctc ttc ttc atg gtt ggg gtt gat gac gat gaa aac     302
Arg Tyr Ala Ser Leu Phe Phe Met Val Gly Val Asp Asp Asp Glu Asn
             65                  70                  75 gag ctg gcg att cta gag ttc ata cat ctt ttg gtc gag aca atg gac     350
Glu Leu Ala Ile Leu Glu Phe Ile His Leu Leu Val Glu Thr Met Asp
         80                  85                  90 aag cat ttt gga aat gtg tgt gag cta gac ata atg ttc cat ctg gag     398
Lys His Phe Gly Asn Val Cys Glu Leu Asp Ile Met Phe His Leu Glu
     95                 100                 105 aaa gct cat ttc atg ctg gaa gaa atg gtg atg aat ggt tgc att gtg     446
Lys Ala His Phe Met Leu Glu Glu Met Val Met Asn Gly Cys Ile Val
110                 115                 120                 125
```

| | | |
|---|---|---|
| gag aca agc aaa gcc aac ata ctt tca cct ata caa ctt atg gac aaa<br>Glu Thr Ser Lys Ala Asn Ile Leu Ser Pro Ile Gln Leu Met Asp Lys<br>         130                   135                 140 | | 494 |
| gcc cat taa tgctaaacac cctgtttcta tttctgttaa tccgtttcat<br>Ala His | | 543 |
| cactttgtta cacacttctt cttgtattat tattaacgat gcttcaaaga gaggataata | | 603 |
| caaaagaagc aggaaatcga aaagtaccaa ttgggagt | | 641 |

<210> SEQ ID NO 14
<211> LENGTH: 143
<212> TYPE: PRT
<213> ORGANISM: Arabidopsis thaliana

<400> SEQUENCE: 14

Met Gly Ile Arg Phe Ile Leu Met Val Asn Lys Gln Gly Gln Thr Arg
1               5                   10                  15

Leu Ala Gln Tyr Tyr Glu Trp Leu Thr Leu Glu Glu Arg Arg Ala Leu
            20                  25                  30

Glu Gly Glu Ile Val Arg Lys Cys Leu Ala Arg Asn Asp Gln Gln Cys
        35                  40                  45

Ser Phe Val Glu His Arg Asn Tyr Lys Ile Val Tyr Arg Arg Tyr Ala
    50                  55                  60

Ser Leu Phe Phe Met Val Gly Val Asp Asp Glu Asn Glu Leu Ala
65                  70                  75                  80

Ile Leu Glu Phe Ile His Leu Leu Val Glu Thr Met Asp Lys His Phe
                85                  90                  95

Gly Asn Val Cys Glu Leu Asp Ile Met Phe His Leu Glu Lys Ala His
            100                 105                 110

Phe Met Leu Glu Glu Met Val Met Asn Gly Cys Ile Val Glu Thr Ser
        115                 120                 125

Lys Ala Asn Ile Leu Ser Pro Ile Gln Leu Met Asp Lys Ala His
    130                 135                 140

<210> SEQ ID NO 15
<211> LENGTH: 1088
<212> TYPE: DNA
<213> ORGANISM: Arabidopsis thaliana
<220> FEATURE:
<221> NAME/KEY: CDS
<222> LOCATION: (350)..(850)

<400> SEQUENCE: 15

| | |
|---|---|
| agagcttgaa ggcaatgcct tgtgtcggta actgacgaat cacaaccgtt gattcgatcg | 60 |
| aattgatccg gtacttctga agctccgatt ctacgtcgac tactttttct ccgatgttaa | 120 |
| catcgtcgtc gtcttctcgg agagccattg attgtgacca atcctcacga cggccccgct | 180 |
| actatttatt agggcactca aatttggtta cacgtggagg gttgttattg gtgatgacgt | 240 |
| catcaaatgt aattgaagaa gcctctaaga tagagagagg gtttgaaaat gtgagattca | 300 |
| gagtttgtca gcgagagaga cgaagaaaga aagagaggag aggtggaag atg att aag<br>                                                                                       Met Ile Lys<br>                                                                                         1 | 358 |
| gca gtg atg atg atg aac aca caa ggc aaa cca cgt cta gct aaa ttc<br>Ala Val Met Met Met Asn Thr Gln Gly Lys Pro Arg Leu Ala Lys Phe<br>     5                   10                   15 | 406 |
| tac gat tac ttg cct gtg gag aag cag cag gag ctt att cgc ggc gtg<br>Tyr Asp Tyr Leu Pro Val Glu Lys Gln Gln Glu Leu Ile Arg Gly Val<br>20                   25                   30                   35 | 454 |

```
ttt tca gta ttg tgc agt aga cct gag aac gta agc aat ttt ctg gag      502
Phe Ser Val Leu Cys Ser Arg Pro Glu Asn Val Ser Asn Phe Leu Glu
            40                  45                  50 atc gaa tca ttg ttt gga ccg gac tcg cgg ctt gta tac aag cat tat      550
Ile Glu Ser Leu Phe Gly Pro Asp Ser Arg Leu Val Tyr Lys His Tyr
        55                  60                  65 gct aca ctc tat ttt gtt ctt gta ttt gat ggt tca gaa aat gag ctt      598
Ala Thr Leu Tyr Phe Val Leu Val Phe Asp Gly Ser Glu Asn Glu Leu
    70                  75                  80 gct atg ctt gat ctc att caa gtt ctt gtt gaa aca ctg gac aaa tgc      646
Ala Met Leu Asp Leu Ile Gln Val Leu Val Glu Thr Leu Asp Lys Cys
85                  90                  95 ttc agc aat gtc tgc gaa ctc gac att gtg ttc aac tac agc aag atg      694
Phe Ser Asn Val Cys Glu Leu Asp Ile Val Phe Asn Tyr Ser Lys Met
100                 105                 110                 115 cac gcg gtg tta gat gag att gta ttt gga gga caa gta ctg gaa act      742
His Ala Val Leu Asp Glu Ile Val Phe Gly Gly Gln Val Leu Glu Thr
                120                 125                 130 agt tct gct gaa gtc atg aag gct gtt gaa gaa ata tca aaa tta gaa      790
Ser Ser Ala Glu Val Met Lys Ala Val Glu Glu Ile Ser Lys Leu Glu
            135                 140                 145 gct gcc tca aat tcg att tca ctt gtc ccc aag tct gtt tcc ggg tgg      838
Ala Ala Ser Asn Ser Ile Ser Leu Val Pro Lys Ser Val Ser Gly Trp
        150                 155                 160 cgt ggc cgt tag cttcgaaaaa acttgcctga ataagtcaga gaacatgtaa           890
Arg Gly Arg
    165 caaaagctta tccaagtctt gatccaaaca tgtttgttta atgagcgtgg aatgttgcgt    950 ggatgggctc agtagtctaa cgtgggcctg tgaattgtaa ttgggtaacg gacggaactg    1010 cttgctattt ttgagaatgt aacaaaaacg acgagaagtt aagatctata aatgataaat    1070 gatgtccaaa ttcagatt                                                  1088

<210> SEQ ID NO 16
<211> LENGTH: 166
<212> TYPE: PRT
<213> ORGANISM: Arabidopsis thaliana

<400> SEQUENCE: 16

Met Ile Lys Ala Val Met Met Asn Thr Gln Gly Lys Pro Arg Leu
1               5                   10                  15

Ala Lys Phe Tyr Asp Tyr Leu Pro Val Glu Lys Gln Gln Glu Leu Ile
            20                  25                  30

Arg Gly Val Phe Ser Val Leu Cys Ser Arg Pro Glu Asn Val Ser Asn
        35                  40                  45

Phe Leu Glu Ile Glu Ser Leu Phe Gly Pro Asp Ser Arg Leu Val Tyr
    50                  55                  60

Lys His Tyr Ala Thr Leu Tyr Phe Val Leu Val Phe Asp Gly Ser Glu
65                  70                  75                  80

Asn Glu Leu Ala Met Leu Asp Leu Ile Gln Val Leu Val Glu Thr Leu
                85                  90                  95

Asp Lys Cys Phe Ser Asn Val Cys Glu Leu Asp Ile Val Phe Asn Tyr
            100                 105                 110

Ser Lys Met His Ala Val Leu Asp Glu Ile Val Phe Gly Gly Gln Val
        115                 120                 125

Leu Glu Thr Ser Ser Ala Glu Val Met Lys Ala Val Glu Glu Ile Ser
    130                 135                 140
```

```
Lys Leu Glu Ala Ala Ser Asn Ser Ile Ser Leu Val Pro Lys Ser Val
145                 150                 155                 160

Ser Gly Trp Arg Gly Arg
            165

<210> SEQ ID NO 17
<211> LENGTH: 786
<212> TYPE: DNA
<213> ORGANISM: Arabidopsis thaliana
<220> FEATURE:
<221> NAME/KEY: CDS
<222> LOCATION: (92)..(580)

<400> SEQUENCE: 17
gcaaagagaa ttttttttctt gttgaggatc atcgattatc agtttctgga tttcgctact    60
acagatttgt cccgtcttga gttacgaaat c atg ata cat ttt gtg ctt cta       112
                                   Met Ile His Phe Val Leu Leu
                                     1               5 gtt agc cgg caa gga aag gta agg ctc acc aaa tgg tat tct cct tat      160
Val Ser Arg Gln Gly Lys Val Arg Leu Thr Lys Trp Tyr Ser Pro Tyr
         10                  15                  20 gca cag aag gaa aga tct aag gtt ata cgt gaa ctc agt gga gtg att      208
Ala Gln Lys Glu Arg Ser Lys Val Ile Arg Glu Leu Ser Gly Val Ile
     25                  30                  35 ctg aat cga ggt cca aag ctc tgc aat ttt gtt gaa tgg aga gga tac      256
Leu Asn Arg Gly Pro Lys Leu Cys Asn Phe Val Glu Trp Arg Gly Tyr
 40                  45                  50                  55 aaa gtt gtt tac aaa aga tat gca agt ctc tac ttc tgc atg tgc att      304
Lys Val Val Tyr Lys Arg Tyr Ala Ser Leu Tyr Phe Cys Met Cys Ile
                 60                  65                  70 gat cag gag gat aac gag tta gag gtc ctt gag atc att cat cac tat      352
Asp Gln Glu Asp Asn Glu Leu Glu Val Leu Glu Ile Ile His His Tyr
             75                  80                  85 gtt gag att ctc gat cgc tat ttt gga agt gtg tgt gaa ctc gat ttg      400
Val Glu Ile Leu Asp Arg Tyr Phe Gly Ser Val Cys Glu Leu Asp Leu
         90                  95                 100 att ttt aac ttc cac aag gca tat tac ata ttg gat gag ctc ttg att      448
Ile Phe Asn Phe His Lys Ala Tyr Tyr Ile Leu Asp Glu Leu Leu Ile
    105                 110                 115 gct ggg gag ctt caa gag tca agc aag aaa aca gta gcc agg att ata      496
Ala Gly Glu Leu Gln Glu Ser Ser Lys Lys Thr Val Ala Arg Ile Ile
120                 125                 130                 135 tcc gct cag gat caa ctg gtg gag gtt gca aaa gag gag gcc agt tcg      544
Ser Ala Gln Asp Gln Leu Val Glu Val Ala Lys Glu Glu Ala Ser Ser
                140                 145                 150 ata agt aat ata atc gct cag gct act aat cga taa gtagtcttat           590
Ile Ser Asn Ile Ile Ala Gln Ala Thr Asn Arg
            155                 160 tcatcatcta tgcattctta tgcagttaaa gtatgttccc tgtctctggc tacagtaatt    650
gttttgagaa atctttatcc atttgatttt tcttgcggag ggattttcgt cttaaagcgt    710
aacttggaga gaagaaatat gttatgattt ggttcataaa caagtaaaga ttatatcgtt    770
tgtaatcttt gatttc                                                    786

<210> SEQ ID NO 18
<211> LENGTH: 162
<212> TYPE: PRT
<213> ORGANISM: Arabidopsis thaliana

<400> SEQUENCE: 18
```

```
Met Ile His Phe Val Leu Leu Val Ser Arg Gln Gly Lys Val Arg Leu
1               5                   10                  15

Thr Lys Trp Tyr Ser Pro Tyr Ala Gln Lys Glu Arg Ser Lys Val Ile
            20                  25                  30

Arg Glu Leu Ser Gly Val Ile Leu Asn Arg Gly Pro Lys Leu Cys Asn
                35                  40                  45

Phe Val Glu Trp Arg Gly Tyr Lys Val Val Tyr Lys Arg Tyr Ala Ser
50                  55                  60

Leu Tyr Phe Cys Met Cys Ile Asp Gln Glu Asp Asn Glu Leu Glu Val
65                  70                  75                  80

Leu Glu Ile Ile His His Tyr Val Glu Ile Leu Asp Arg Tyr Phe Gly
                85                  90                  95

Ser Val Cys Glu Leu Asp Leu Ile Phe Asn Phe His Lys Ala Tyr Tyr
                100                 105                 110

Ile Leu Asp Glu Leu Leu Ile Ala Gly Glu Leu Gln Glu Ser Ser Lys
                115                 120                 125

Lys Thr Val Ala Arg Ile Ile Ser Ala Gln Asp Gln Leu Val Glu Val
130                 135                 140

Ala Lys Glu Glu Ala Ser Ser Ile Ser Asn Ile Ile Ala Gln Ala Thr
145                 150                 155                 160

Asn Arg

<210> SEQ ID NO 19
<211> LENGTH: 969
<212> TYPE: DNA
<213> ORGANISM: Populus trichocarpa
<220> FEATURE:
<221> NAME/KEY: CDS
<222> LOCATION: (40)..(573)

<400> SEQUENCE: 19
gagagtcacc tgaatctcca cctctcccga tctgcaaat atg gat tcc tgc ccc      54
                                          Met Asp Ser Cys Pro
                                          1               5 gtg gtg aaa aac att ctt ctg cta gac tct gaa ggg aag cga gtt gcg   102
Val Val Lys Asn Ile Leu Leu Leu Asp Ser Glu Gly Lys Arg Val Ala
            10                  15                  20 gtc aaa tac tat tca gat gac tgg ccg acc aat aat gca aag tta gct   150
Val Lys Tyr Tyr Ser Asp Asp Trp Pro Thr Asn Asn Ala Lys Leu Ala
        25                  30                  35 ttt gaa aaa ttg ctt ttt gca aag act atg aaa tca aat gcc cgc aca   198
Phe Glu Lys Leu Leu Phe Ala Lys Thr Met Lys Ser Asn Ala Arg Thr
    40                  45                  50 gaa gcg gag att aca atg ttt gac agt aac att gtc atc tac aaa tgt   246
Glu Ala Glu Ile Thr Met Phe Asp Ser Asn Ile Val Ile Tyr Lys Cys
55                  60                  65 gtc cag gac ctc cat ttt tat gtg act gga ggt gag gat gaa aat gaa   294
Val Gln Asp Leu His Phe Tyr Val Thr Gly Gly Glu Asp Glu Asn Glu
70                  75                  80                  85 ctc att tta gct gct gtt ctt cag ggt ttc ttt gat tca gtc tct ctt   342
Leu Ile Leu Ala Ala Val Leu Gln Gly Phe Phe Asp Ser Val Ser Leu
                90                  95                  100 ctc ttg agg agc aat gtc gac aaa agg gag gca ctt gaa aac tta gat   390
Leu Leu Arg Ser Asn Val Asp Lys Arg Glu Ala Leu Glu Asn Leu Asp
                105                 110                 115 ctc att ttc tta tgc ctt gat gag att gtt gaa aga ggc atg atc ctc   438
Leu Ile Phe Leu Cys Leu Asp Glu Ile Val Glu Arg Gly Met Ile Leu
            120                 125                 130
```

| | | | | | | | | | | | | | | | | |
|---|---|---|---|---|---|---|---|---|---|---|---|---|---|---|---|---|
| gaa | aca | gat | gcc | aat | gtt | att | gct | gga | aag | gtg | gct | gta | aat | agc | atg | 486 |
| Glu | Thr | Asp | Ala | Asn | Val | Ile | Ala | Gly | Lys | Val | Ala | Val | Asn | Ser | Met | |
| | 135 | | | | 140 | | | | | 145 | | | | | | |
| gat | cct | agt | gca | cct | cta | tcc | gag | cag | aca | ata | ggt | caa | gca | ttg | gcc | 534 |
| Asp | Pro | Ser | Ala | Pro | Leu | Ser | Glu | Gln | Thr | Ile | Gly | Gln | Ala | Leu | Ala | |
| 150 | | | | | 155 | | | | | 160 | | | | | 165 | |
| aca | gct | cgt | gaa | cac | ttg | acg | aga | acc | ctt | ttt | cag | tag | gtttttcatg | | | 583 |
| Thr | Ala | Arg | Glu | His | Leu | Thr | Arg | Thr | Leu | Phe | Gln | | | | | |
| | | | 170 | | | | | 175 | | | | | | | | |

| | |
|---|---|
| cacactcaga ggtgccttgg ctttattctc ttggttaagt attttccat ttattggcct | 643 |
| ttaagcagtt tgttccatgt attttgtct gagtttattg aacaacgagg attgttttag | 703 |
| gcttgtaatg gagcaactcc tatccagcca ataatgtctc tttagcttc attgtgatcc | 763 |
| ttggtgttta tgggccgtgg catgactgtg acctaattaa tacagttgat gcttgcagct | 823 |
| atatctatgc acaacttatt agatttgggt ctcttaggca taatgtaaac atgcagtgtc | 883 |
| ttgtacttca tttgaaaaaa ttacaccgta tgtgcactgg gaacaaatgc gtgaaattgg | 943 |
| tattttcgc aaaaaaaaaa aaaaaa | 969 |

<210> SEQ ID NO 20
<211> LENGTH: 177
<212> TYPE: PRT
<213> ORGANISM: Populus trichocarpa

<400> SEQUENCE: 20

Met Asp Ser Cys Pro Val Val Lys Asn Ile Leu Leu Asp Ser Glu
1               5                   10                  15

Gly Lys Arg Val Ala Val Lys Tyr Tyr Ser Asp Asp Trp Pro Thr Asn
                20                  25                  30

Asn Ala Lys Leu Ala Phe Glu Lys Leu Leu Phe Ala Lys Thr Met Lys
            35                  40                  45

Ser Asn Ala Arg Thr Glu Ala Glu Ile Thr Met Phe Asp Ser Asn Ile
        50                  55                  60

Val Ile Tyr Lys Cys Val Gln Asp Leu His Phe Tyr Val Thr Gly Gly
65                  70                  75                  80

Glu Asp Glu Asn Glu Leu Ile Leu Ala Ala Val Leu Gln Gly Phe Phe
                85                  90                  95

Asp Ser Val Ser Leu Leu Leu Arg Ser Asn Val Asp Lys Arg Glu Ala
            100                 105                 110

Leu Glu Asn Leu Asp Leu Ile Phe Leu Cys Leu Asp Glu Ile Val Glu
        115                 120                 125

Arg Gly Met Ile Leu Glu Thr Asp Ala Asn Val Ile Ala Gly Lys Val
    130                 135                 140

Ala Val Asn Ser Met Asp Pro Ser Ala Pro Leu Ser Glu Gln Thr Ile
145                 150                 155                 160

Gly Gln Ala Leu Ala Thr Ala Arg Glu His Leu Thr Arg Thr Leu Phe
                165                 170                 175

Gln

<210> SEQ ID NO 21
<211> LENGTH: 802
<212> TYPE: DNA
<213> ORGANISM: Picea sitchensis
<220> FEATURE:
<221> NAME/KEY: CDS
<222> LOCATION: (87)..(620)

<400> SEQUENCE: 21

-continued

```
gggtgtgttg atgtgttgcg gtggagaaag tggctgagaa ttacctgcac tcataaaaca         60
aaacatcgac gttgtttgat ctctcg atg gaa tct tgt cct ctg atc aaa aac        113
                             Met Glu Ser Cys Pro Leu Ile Lys Asn
                               1               5 att ttg ctt cta gat tca gag gga aaa cgg gtt gca gtt aag tac tat         161
Ile Leu Leu Leu Asp Ser Glu Gly Lys Arg Val Ala Val Lys Tyr Tyr
 10              15                  20                  25 tcc gat gac tgg cca acc ctt gct tca aag cta gct ttt gaa aaa tct         209
Ser Asp Asp Trp Pro Thr Leu Ala Ser Lys Leu Ala Phe Glu Lys Ser
                 30                  35                  40 gtt ttt acc aaa act caa aag aca aat gcc cgt gca gaa gct gaa att         257
Val Phe Thr Lys Thr Gln Lys Thr Asn Ala Arg Ala Glu Ala Glu Ile
             45                  50                  55 ggc atg ttc gat agc ttt att gtt ctg tat aag ttc atc tct gat cta         305
Gly Met Phe Asp Ser Phe Ile Val Leu Tyr Lys Phe Ile Ser Asp Leu
         60                  65                  70 cat ttt tac gtc acc ggt ggt gat gat gag aat gag ctt gtt ttg gct         353
His Phe Tyr Val Thr Gly Gly Asp Asp Glu Asn Glu Leu Val Leu Ala
 75                  80                  85 aca gtt ctt caa ggc ttc ttt gat gca gtt gca ctt ctt ctc agg aac         401
Thr Val Leu Gln Gly Phe Phe Asp Ala Val Ala Leu Leu Leu Arg Asn
 90                  95                 100                 105 aac gtg gag aaa aga aca gct ctt gag aat tta gat ctc atc ttt ctt         449
Asn Val Glu Lys Arg Thr Ala Leu Glu Asn Leu Asp Leu Ile Phe Leu
                110                 115                 120 tgt ctt gat gag att gtt gat gga gga atc att tta gag act gaa gca         497
Cys Leu Asp Glu Ile Val Asp Gly Gly Ile Ile Leu Glu Thr Glu Ala
             125                 130                 135 agt tta att gct gga agg atg gtg acc cat ggt gct gat gga gga gca         545
Ser Leu Ile Ala Gly Arg Met Val Thr His Gly Ala Asp Gly Gly Ala
         140                 145                 150 ccc ctt tcc gag cag act ata tct caa gcg ctt gca tct gca agg gaa         593
Pro Leu Ser Glu Gln Thr Ile Ser Gln Ala Leu Ala Ser Ala Arg Glu
 155                 160                 165 cat cta gca aga tca ctt cta aaa taa tcatttgttt aattcttccc               640
His Leu Ala Arg Ser Leu Leu Lys
170                 175 ggcatttgaa ctctgccacc ttactgctga tgctcagcgg tcgtggatat tacttgaagc       700
ttatgctcat cactttttcta aattgtaaat tttcattgga atcacatgcc attctgtctt      760
accgtttcaa gctaatccaa attcacaaaa aaaaaaaaaa aa                          802
```

<210> SEQ ID NO 22
<211> LENGTH: 177
<212> TYPE: PRT
<213> ORGANISM: Picea sitchensis

<400> SEQUENCE: 22

```
Met Glu Ser Cys Pro Leu Ile Lys Asn Ile Leu Leu Asp Ser Glu
 1               5                  10                  15

Gly Lys Arg Val Ala Val Lys Tyr Tyr Ser Asp Asp Trp Pro Thr Leu
             20                  25                  30

Ala Ser Lys Leu Ala Phe Glu Lys Ser Val Phe Thr Lys Thr Gln Lys
         35                  40                  45

Thr Asn Ala Arg Ala Glu Ala Glu Ile Gly Met Phe Asp Ser Phe Ile
     50                  55                  60

Val Leu Tyr Lys Phe Ile Ser Asp Leu His Phe Tyr Val Thr Gly Gly
 65                  70                  75                  80
```

```
Asp Asp Glu Asn Glu Leu Val Leu Ala Thr Val Leu Gln Gly Phe Phe
            85                  90                  95

Asp Ala Val Ala Leu Leu Leu Arg Asn Val Glu Lys Arg Thr Ala
            100                 105                 110

Leu Glu Asn Leu Asp Leu Ile Phe Leu Cys Leu Asp Glu Ile Val Asp
            115                 120                 125

Gly Gly Ile Ile Leu Glu Thr Glu Ala Ser Leu Ile Ala Gly Arg Met
        130                 135                 140

Val Thr His Gly Ala Asp Gly Gly Ala Pro Leu Ser Glu Gln Thr Ile
145                 150                 155                 160

Ser Gln Ala Leu Ala Ser Ala Arg Glu His Leu Ala Arg Ser Leu Leu
                165                 170                 175

Lys
```

<210> SEQ ID NO 23
<211> LENGTH: 1018
<212> TYPE: DNA
<213> ORGANISM: Zea mays
<220> FEATURE:
<221> NAME/KEY: CDS
<222> LOCATION: (169)..(717)

<400> SEQUENCE: 23

```
cttgattagc aatcactgct gcgcccgata ggtggcagcg agccagcgag ccagcgaccc      60
acccgactct gttccaacga gccttccctc ccaaacttgc acgctgcccc cgcgctcgcc     120 tccgccccg atccagatcc agggtggaat agggaacggc catacacc atg gcg gat     177
                                                     Met Ala Asp
                                                       1 ttc tcc aag gaa tct tgc cct tct gtg aag aac att tta ctt ctg gat      225
Phe Ser Lys Glu Ser Cys Pro Ser Val Lys Asn Ile Leu Leu Leu Asp
      5                  10                  15 tct gaa gga aag cgt gtt gct gta aag tat ttc tca gat gat tgg ccg      273
Ser Glu Gly Lys Arg Val Ala Val Lys Tyr Phe Ser Asp Asp Trp Pro
 20                  25                  30                  35 act aat gca tca aag tta gcc tac gaa aag tct gtt ttt act aaa act      321
Thr Asn Ala Ser Lys Leu Ala Tyr Glu Lys Ser Val Phe Thr Lys Thr
             40                  45                  50 cta aag aca aat gca cgg aca gaa gct gag ata aca ttg ttt gat ggt      369
Leu Lys Thr Asn Ala Arg Thr Glu Ala Glu Ile Thr Leu Phe Asp Gly
         55                  60                  65 tat att gtc gtt tac aag ttt gta cat gac ctt cac ttt ttt gtc acc      417
Tyr Ile Val Val Tyr Lys Phe Val His Asp Leu His Phe Phe Val Thr
     70                  75                  80 gct gga gat gat gag aat gag ctc atc tta gca agt gta cta cat ggt      465
Ala Gly Asp Asp Glu Asn Glu Leu Ile Leu Ala Ser Val Leu His Gly
 85                  90                  95 ttt tct gat tct gtt ggt ctt cta ctc agg agt gat gtt gag aag cgg      513
Phe Ser Asp Ser Val Gly Leu Leu Leu Arg Ser Asp Val Glu Lys Arg
100                 105                 110                 115 act gcg ctt gag aac ttg gat ttg ata ctt ctc tgc att gat gaa att      561
Thr Ala Leu Glu Asn Leu Asp Leu Ile Leu Leu Cys Ile Asp Glu Ile
             120                 125                 130 gta gat ggg gga atc atc ctg gaa aca gat gca aac acc att gct ggt      609
Val Asp Gly Gly Ile Ile Leu Glu Thr Asp Ala Asn Thr Ile Ala Gly
         135                 140                 145 aag gtt gca acc aat gct gtt gat ggt tct gtg ccc ttt tct gag cag      657
Lys Val Ala Thr Asn Ala Val Asp Gly Ser Val Pro Phe Ser Glu Gln
     150                 155                 160
```

```
acg ata tct cag gca cta gcc aca gct agg gag cac ctt gca aga tct    705
Thr Ile Ser Gln Ala Leu Ala Thr Ala Arg Glu His Leu Ala Arg Ser
    165                 170                 175 cta ctg aaa tga acaaccagca atatgtatga catatatgtg tgttaaaggt        757
Leu Leu Lys
180 tgggctactg aatgttaagg gtctttgtag tcgttattca tcccaaagtg ctgctgtgac  817 agagcctagt tgaatatccg agggattggt cacatgctcg ttatttttt tgaaccagtg   877 agtttgtagc tgccatattt caggtaaaac ataaataaa gagttgtaat tgggtgtaat   937 ataattttca ccatacaaaa aaatcatctc aactatcaaa ccatggtaaa aggttcaaaa  997 ttatcaaaaa aaaaaaaaaa a                                           1018

<210> SEQ ID NO 24
<211> LENGTH: 182
<212> TYPE: PRT
<213> ORGANISM: Zea mays

<400> SEQUENCE: 24

Met Ala Asp Phe Ser Lys Glu Ser Cys Pro Ser Val Lys Asn Ile Leu
1               5                   10                  15

Leu Leu Asp Ser Glu Gly Lys Arg Val Ala Val Lys Tyr Phe Ser Asp
            20                  25                  30

Asp Trp Pro Thr Asn Ala Ser Lys Leu Ala Tyr Glu Lys Ser Val Phe
        35                  40                  45

Thr Lys Thr Leu Lys Thr Asn Ala Arg Thr Glu Ala Glu Ile Thr Leu
    50                  55                  60

Phe Asp Gly Tyr Ile Val Val Tyr Lys Phe Val His Asp Leu His Phe
65                  70                  75                  80

Phe Val Thr Ala Gly Asp Asp Glu Asn Glu Leu Ile Leu Ala Ser Val
                85                  90                  95

Leu His Gly Phe Ser Asp Ser Val Gly Leu Leu Leu Arg Ser Asp Val
            100                 105                 110

Glu Lys Arg Thr Ala Leu Glu Asn Leu Asp Leu Ile Leu Leu Cys Ile
        115                 120                 125

Asp Glu Ile Val Asp Gly Gly Ile Ile Leu Glu Thr Asp Ala Asn Thr
    130                 135                 140

Ile Ala Gly Lys Val Ala Thr Asn Ala Val Asp Gly Ser Val Pro Phe
145                 150                 155                 160

Ser Glu Gln Thr Ile Ser Gln Ala Leu Ala Thr Ala Arg Glu His Leu
                165                 170                 175

Ala Arg Ser Leu Leu Lys
            180

<210> SEQ ID NO 25
<211> LENGTH: 1284
<212> TYPE: DNA
<213> ORGANISM: Zea mays
<220> FEATURE:
<221> NAME/KEY: CDS
<222> LOCATION: (138)..(683)

<400> SEQUENCE: 25
gcgacccacc cgactctgtt ccaacgagcc ttccctccca aacttgcacg ctgccccgc    60 gctcgcctcc gccccgatc cagatccagg gtggaatagg gaacggccat acaccatggc   120
ggatttctcc aagtgat atg tct gtt tca cag gaa tct tgc cct tct gtg     170
```

```
            Met Ser Val Ser Gln Glu Ser Cys Pro Ser Val
            1               5                   10 aag aac att tta ctt ctg gat tct gaa gga aag cgt gtt gct gta aag       218
Lys Asn Ile Leu Leu Leu Asp Ser Glu Gly Lys Arg Val Ala Val Lys
            15                  20                  25 tat ttc tca gat gat tgg ccg act aat gca tca aag tta gcc tac gaa       266
Tyr Phe Ser Asp Asp Trp Pro Thr Asn Ala Ser Lys Leu Ala Tyr Glu
            30                  35                  40 aag tct gtt ttt act aaa act cta aag aca aat gca cgg aca gaa gct       314
Lys Ser Val Phe Thr Lys Thr Leu Lys Thr Asn Ala Arg Thr Glu Ala
            45                  50                  55 gag ata aca ttg ttt gat ggt tat att gtc gtt tac aag ttt gta cat       362
Glu Ile Thr Leu Phe Asp Gly Tyr Ile Val Val Tyr Lys Phe Val His
60                  65                  70                  75 gac ctt cac ttt ttt gtc acc gct gga gat gat gag aat gag ctc atc       410
Asp Leu His Phe Phe Val Thr Ala Gly Asp Asp Glu Asn Glu Leu Ile
                80                  85                  90 tta gca agt gta cta cat ggt ttt tct gat tct gtt ggt ctt cta ctc       458
Leu Ala Ser Val Leu His Gly Phe Ser Asp Ser Val Gly Leu Leu Leu
            95                  100                 105 agg ggt gat gtt gag aag cgg act gcg ctt gag aac ttg gat ttg ata       506
Arg Gly Asp Val Glu Lys Arg Thr Ala Leu Glu Asn Leu Asp Leu Ile
            110                 115                 120 ctt ctc tgc att gat gaa att gtg gat ggg gga atc atc ctg gaa aca       554
Leu Leu Cys Ile Asp Glu Ile Val Asp Gly Gly Ile Ile Leu Glu Thr
125                 130                 135 gat gca aac acc att gct ggt aag gtt gca acc aat gct gtt gat ggt       602
Asp Ala Asn Thr Ile Ala Gly Lys Val Ala Thr Asn Ala Val Asp Gly
140                 145                 150                 155 tct gtg ccc ttt tct gag cag acg ata tct cag gca cta gcc aca gct       650
Ser Val Pro Phe Ser Glu Gln Thr Ile Ser Gln Ala Leu Ala Thr Ala
                160                 165                 170 agg gag cac ctt gca aga tct cta ctg aaa tga acaaccagca atatgtatga    703
Arg Glu His Leu Ala Arg Ser Leu Leu Lys
            175                 180 catatatgtg tgttaaaggt tgggctactg aatgttaagg gtctttgtag tcgttattca    763
tcccaaagtg ctgctgtgac agagcctagt tgaatatccg agggattggt cacatgctcg    823 ttatttttt tgaaccagtg agtttgtagc tgccatattt caggtaaaac ataaataaa      883 gagttgtaat tgggtgtaat ataattttca ccatacaaaa aaaatcatct caactatcaa    943
accatggtaa aaggttcaaa attatctatc aaatgattat ccctccaggt cggaggaaga   1003
atggatcctc cgtcattgaa aaggtatgga ggctttactc ttgctcataa tcggatcaaa   1063
agaatcctta tttgtattag ttttcttcta ggtttagtcc tacatcaagt cagttgcccg   1123
aggcatctga ttgaaaatgt actttatagg ccatatttga ttttgctttc cccgcaccac   1183
gcttagattc tacaactcgt gattattcga ttcttgctta tagttcaact ggtgaattat   1243
cgtttgggta agatgctaaa ataatctaga tgtttgatgg c                       1284
```

<210> SEQ ID NO 26
<211> LENGTH: 181
<212> TYPE: PRT
<213> ORGANISM: Zea mays

<400> SEQUENCE: 26

Met Ser Val Ser Gln Glu Ser Cys Pro Ser Val Lys Asn Ile Leu Leu
1               5                   10                  15

Leu Asp Ser Glu Gly Lys Arg Val Ala Val Lys Tyr Phe Ser Asp Asp

```
              20                  25                  30
Trp Pro Thr Asn Ala Ser Lys Leu Ala Tyr Glu Lys Ser Val Phe Thr
         35                  40                  45

Lys Thr Leu Lys Thr Asn Ala Arg Thr Glu Ala Glu Ile Thr Leu Phe
 50                  55                  60

Asp Gly Tyr Ile Val Val Tyr Lys Phe Val His Asp Leu His Phe Phe
 65                  70                  75                  80

Val Thr Ala Gly Asp Asp Glu Asn Glu Leu Ile Leu Ala Ser Val Leu
             85                  90                  95

His Gly Phe Ser Asp Ser Val Gly Leu Leu Arg Gly Asp Val Glu
             100                 105                 110

Lys Arg Thr Ala Leu Glu Asn Leu Asp Leu Ile Leu Leu Cys Ile Asp
             115                 120                 125

Glu Ile Val Asp Gly Gly Ile Ile Leu Glu Thr Asp Ala Asn Thr Ile
             130                 135                 140

Ala Gly Lys Val Ala Thr Asn Ala Val Asp Gly Ser Val Pro Phe Ser
145                 150                 155                 160

Glu Gln Thr Ile Ser Gln Ala Leu Ala Thr Ala Arg Glu His Leu Ala
                 165                 170                 175

Arg Ser Leu Leu Lys
             180

<210> SEQ ID NO 27
<211> LENGTH: 808
<212> TYPE: DNA
<213> ORGANISM: Lotus japonicus
<220> FEATURE:
<221> NAME/KEY: CDS
<222> LOCATION: (93)..(641)

<400> SEQUENCE: 27
ggaaagaaga ctcatttgac actggttgaa gaaaaacatt cactgagtct cagaagcttc    60
tccttctttc ctccgtcgac ggtttctcca cc atg tct cct cct ccc aat gag    113
                                   Met Ser Pro Pro Pro Asn Glu
                                    1               5 tta tgc cct tct gtg aag aat atc ctt ttg ctt gat tct gac ggg aaa    161
Leu Cys Pro Ser Val Lys Asn Ile Leu Leu Leu Asp Ser Asp Gly Lys
         10                  15                  20 cgt gtg gcg gtc aag tat ttc tct gat gac tgg cca acc aat agt gca    209
Arg Val Ala Val Lys Tyr Phe Ser Asp Asp Trp Pro Thr Asn Ser Ala
 25                  30                  35 cag gag gct ttt gag aag ctt gtg ttc acc aag act cag aag acc aat    257
Gln Glu Ala Phe Glu Lys Leu Val Phe Thr Lys Thr Gln Lys Thr Asn
 40                  45                  50                  55 gcc cgc acg gaa gcg gag ata aca atg ctt gag aat tac att gtt gtt    305
Ala Arg Thr Glu Ala Glu Ile Thr Met Leu Glu Asn Tyr Ile Val Val
             60                  65                  70 tac aag ttt gtc caa gat ctt cac ttc ttt gtt acc ggg ggt gac gaa    353
Tyr Lys Phe Val Gln Asp Leu His Phe Phe Val Thr Gly Gly Asp Glu
             75                  80                  85 gaa aat gag ctt atc tta gcc aca gtt ctg cag gca ttt ttc gat tct    401
Glu Asn Glu Leu Ile Leu Ala Thr Val Leu Gln Ala Phe Phe Asp Ser
         90                  95                 100 gtt ggc ctc ctg ctc aga ggc aat gtg gac aag aag gaa gca ctt gag    449
Val Gly Leu Leu Leu Arg Gly Asn Val Asp Lys Lys Glu Ala Leu Glu
     105                 110                 115 aac ttg gat ctg att ctt ctt tgc att gat gaa att att gat ggc ggt    497
Asn Leu Asp Leu Ile Leu Leu Cys Ile Asp Glu Ile Ile Asp Gly Gly
```

```
atc att ctt gaa act gat cca aat gtg ata gct ggg aaa gtg gca agt    545
Ile Ile Leu Glu Thr Asp Pro Asn Val Ile Ala Gly Lys Val Ala Ser
            140                 145                 150 aat agt ata gat tct gga gct cct tta tct gaa cag aca tta act caa    593
Asn Ser Ile Asp Ser Gly Ala Pro Leu Ser Glu Gln Thr Leu Thr Gln
        155                 160                 165 gca ttg gcc aca gcc agg gaa cat ttt gca aga tcc ctt ctt aaa tga    641
Ala Leu Ala Thr Ala Arg Glu His Phe Ala Arg Ser Leu Leu Lys
170                 175                 180 accacatatg agatttggca atggatgaaa cttatcttct ggctttccta gaaacgctta   701
taaagatatc aatttacatt gcattcttgg atgatgatat ttacttgggt tgtggaaatt   761
attttgacat gcgatatagc ttttggcact cttttctgca cattttg                 808
```

<210> SEQ ID NO 28
<211> LENGTH: 182
<212> TYPE: PRT
<213> ORGANISM: Lotus japonicus

<400> SEQUENCE: 28

```
Met Ser Pro Pro Pro Asn Glu Leu Cys Pro Ser Val Lys Asn Ile Leu
1               5                   10                  15

Leu Leu Asp Ser Asp Gly Lys Arg Val Ala Val Lys Tyr Phe Ser Asp
                20                  25                  30

Asp Trp Pro Thr Asn Ser Ala Gln Glu Ala Phe Glu Lys Leu Val Phe
            35                  40                  45

Thr Lys Thr Gln Lys Thr Asn Ala Arg Thr Glu Ala Glu Ile Thr Met
        50                  55                  60

Leu Glu Asn Tyr Ile Val Val Tyr Lys Phe Val Gln Asp Leu His Phe
65                  70                  75                  80

Phe Val Thr Gly Gly Asp Glu Glu Asn Glu Leu Ile Leu Ala Thr Val
                85                  90                  95

Leu Gln Ala Phe Phe Asp Ser Val Gly Leu Leu Leu Arg Gly Asn Val
            100                 105                 110

Asp Lys Lys Glu Ala Leu Glu Asn Leu Asp Leu Ile Leu Leu Cys Ile
        115                 120                 125

Asp Glu Ile Ile Asp Gly Gly Ile Ile Leu Glu Thr Asp Pro Asn Val
130                 135                 140

Ile Ala Gly Lys Val Ala Ser Asn Ser Ile Asp Ser Gly Ala Pro Leu
145                 150                 155                 160

Ser Glu Gln Thr Leu Thr Gln Ala Leu Ala Thr Ala Arg Glu His Phe
                165                 170                 175

Ala Arg Ser Leu Leu Lys
            180
```

<210> SEQ ID NO 29
<211> LENGTH: 751
<212> TYPE: DNA
<213> ORGANISM: Brassica rapa
<220> FEATURE:
<221> NAME/KEY: CDS
<222> LOCATION: (35)..(589)

<400> SEQUENCE: 29

```
tggatctcaa gcttcaagtg acgataactc aaca atg tca ggc ttt cac ggg act    55
                                   Met Ser Gly Phe His Gly Thr
                                   1               5
```

| | | |
|---|---|---|
| cat gat tca tgt cct ttg gtg aag aac att ctt ctt cta gac tct gaa<br>His Asp Ser Cys Pro Leu Val Lys Asn Ile Leu Leu Leu Asp Ser Glu<br>10 15 20 | 103 | |
| ggg aag cgt gtg gct gtc aag tac tac tcc gat gac tgg cca act cat<br>Gly Lys Arg Val Ala Val Lys Tyr Tyr Ser Asp Asp Trp Pro Thr His<br>25 30 35 | 151 | |
| gct gcc aag ttg act ttt gag aag tat gtc ttc tcc aag acc tct aag<br>Ala Ala Lys Leu Thr Phe Glu Lys Tyr Val Phe Ser Lys Thr Ser Lys<br>40 45 50 55 | 199 | |
| acc aat gct cgc act gaa gct gag atc aca ctc ttg gac agt aac atc<br>Thr Asn Ala Arg Thr Glu Ala Glu Ile Thr Leu Leu Asp Ser Asn Ile<br>60 65 70 | 247 | |
| att gtc tat aag ttc gcc cag gac ctt cac ttc ttt gtt act gga ggc<br>Ile Val Tyr Lys Phe Ala Gln Asp Leu His Phe Phe Val Thr Gly Gly<br>75 80 85 | 295 | |
| gaa aat gaa aac gag ctc gtc ttg tct tcg gtt ctt caa ggc ttt ttc<br>Glu Asn Glu Asn Glu Leu Val Leu Ser Ser Val Leu Gln Gly Phe Phe<br>90 95 100 | 343 | |
| gat gct gtt gct ctt ctt ctg agg aac aat gtt gaa aag atg gaa gct<br>Asp Ala Val Ala Leu Leu Leu Arg Asn Asn Val Glu Lys Met Glu Ala<br>105 110 115 | 391 | |
| ctc gag aac ttg gat ctc atc ttt ctg tgc ctg gat gaa atg gtc gat<br>Leu Glu Asn Leu Asp Leu Ile Phe Leu Cys Leu Asp Glu Met Val Asp<br>120 125 130 135 | 439 | |
| cag ggg gtg gtt ctt gaa aca gac cct aac gtc att gcg ggg aaa gta<br>Gln Gly Val Val Leu Glu Thr Asp Pro Asn Val Ile Ala Gly Lys Val<br>140 145 150 | 487 | |
| gca atg cag agc aca gaa gct agt ggt tca ctc tct gaa cag aca tta<br>Ala Met Gln Ser Thr Glu Ala Ser Gly Ser Leu Ser Glu Gln Thr Leu<br>155 160 165 | 535 | |
| act caa gca ctg gca aca gct cgg gaa cat ctg gca aga agt ctg ctt<br>Thr Gln Ala Leu Ala Thr Ala Arg Glu His Leu Ala Arg Ser Leu Leu<br>170 175 180 | 583 | |
| aca tga gtttcctcgt atccattgca tgcccacaca taatagaatg gacttccaac<br>Thr | 639 | |
| ttctgtgaaa gtcttgtaat aattcaaaca ctctgcttac tttaatgttt ggggtattgt | 699 | |
| atatcagtgt gtgcaatgct ggaatatatt ttttttttga ctaaaaaaaa aa | 751 | |

<210> SEQ ID NO 30
<211> LENGTH: 184
<212> TYPE: PRT
<213> ORGANISM: Brassica rapa

<400> SEQUENCE: 30

Met Ser Gly Phe His Gly Thr His Asp Ser Cys Pro Leu Val Lys Asn
1               5                   10                  15

Ile Leu Leu Leu Asp Ser Glu Gly Lys Arg Val Ala Val Lys Tyr Tyr
                20                  25                  30

Ser Asp Asp Trp Pro Thr His Ala Ala Lys Leu Thr Phe Glu Lys Tyr
            35                  40                  45

Val Phe Ser Lys Thr Ser Lys Thr Asn Ala Arg Thr Glu Ala Glu Ile
        50                  55                  60

Thr Leu Leu Asp Ser Asn Ile Ile Val Tyr Lys Phe Ala Gln Asp Leu
65                  70                  75                  80

His Phe Phe Val Thr Gly Gly Glu Asn Glu Asn Glu Leu Val Leu Ser
                85                  90                  95

Ser Val Leu Gln Gly Phe Phe Asp Ala Val Ala Leu Leu Leu Arg Asn
                100                 105                 110

```
Asn Val Glu Lys Met Glu Ala Leu Glu Asn Leu Asp Leu Ile Phe Leu
        115                 120                 125

Cys Leu Asp Glu Met Val Asp Gln Gly Val Val Leu Glu Thr Asp Pro
    130                 135                 140

Asn Val Ile Ala Gly Lys Val Ala Met Gln Ser Thr Glu Ala Ser Gly
145                 150                 155                 160

Ser Leu Ser Glu Gln Thr Leu Thr Gln Ala Leu Ala Thr Ala Arg Glu
            165                 170                 175

His Leu Ala Arg Ser Leu Leu Thr
        180

<210> SEQ ID NO 31
<211> LENGTH: 977
<212> TYPE: DNA
<213> ORGANISM: Hordeum Vulgare
<220> FEATURE:
<221> NAME/KEY: CDS
<222> LOCATION: (140)..(673)

<400> SEQUENCE: 31
tggttgtcat tattgatctt cgtcctggtc gccgccctcc cttggcctgc gctcgcacag      60
cagcagccgg ccaatccctc cggcacgccg tcgctcgtcc cgcccccggc gcccgcgaat     120
ccgtcctccc ccctcgac atg gcg ccc tgc cct tcc gtc aag aac atc ctc      172
                    Met Ala Pro Cys Pro Ser Val Lys Asn Ile Leu
                     1               5                      10 gtg ctg gac gcg gag ggg aag cgc gtg gcc gtg aag tac tac gcc gac      220
Val Leu Asp Ala Glu Gly Lys Arg Val Ala Val Lys Tyr Tyr Ala Asp
            15                  20                  25 gac tgg ccc tcc gct tcc tcc aag atg gct ttc gag aag tcg ctc ttc      268
Asp Trp Pro Ser Ala Ser Ser Lys Met Ala Phe Glu Lys Ser Leu Phe
        30                  35                  40 gtg aag acc cag aaa acc agc gcc aga gca gag gct gat gtg gta atg      316
Val Lys Thr Gln Lys Thr Ser Ala Arg Ala Glu Ala Asp Val Val Met
 45                 50                  55 ttt gat ggc tac att gtt gtt tac aag ttc atc caa gat ctc cat ttt      364
Phe Asp Gly Tyr Ile Val Val Tyr Lys Phe Ile Gln Asp Leu His Phe
 60                 65                  70                  75 ttt gta act gga ggg gat gag gag aat gag ctt att tta gcg tca gtt      412
Phe Val Thr Gly Gly Asp Glu Glu Asn Glu Leu Ile Leu Ala Ser Val
            80                  85                  90 ctt caa ggg ttt tct gat gct gtt ggc gtt ctt ctc aga aac aat gta      460
Leu Gln Gly Phe Ser Asp Ala Val Gly Val Leu Leu Arg Asn Asn Val
        95                  100                 105 gac aaa agg aca gct ctt gaa aat ctg gat ctc atc ttt ttg tgc ctc      508
Asp Lys Arg Thr Ala Leu Glu Asn Leu Asp Leu Ile Phe Leu Cys Leu
    110                 115                 120 gac gaa gtt gtt gat gga ggg att gtt ctg gaa aca gat gga aat gcg      556
Asp Glu Val Val Asp Gly Gly Ile Val Leu Glu Thr Asp Gly Asn Ala
125                 130                 135 ata gcc gag aag gtg tca ggc cat gga ttg gaa gga gct gga tcg ttc      604
Ile Ala Glu Lys Val Ser Gly His Gly Leu Glu Gly Ala Gly Ser Phe
140                 145                 150                 155 acc gag cag acg ata agc caa gcc cta gca aca gca aga gag cac ttc      652
Thr Glu Gln Thr Ile Ser Gln Ala Leu Ala Thr Ala Arg Glu His Phe
            160                 165                 170 gcg agg tct ctt ctg aag tag tgtgtacatg catctttcct gttggcgatg         703
Ala Arg Ser Leu Leu Lys
        175
```

```
cacccaccat tgaactcctg tgtttcctct tgtagcacag tgcacctagt ttgttaagaa    763
agaaagaacg agaaaatgac ttgaatcttt gcgtgtgact tcgttcacct attgttgtgg    823
tgtgagtcga cattttgtcg cagagatgta tgtgcggcct aagcgcctag tcctggttac    883
aggttaccag attccttta aggtctgtaa aagaaacttg tgatgcatgc aatcgttggt     943
gcataacaat ccagtaacat cacatgatgc tacc                                977
```

<210> SEQ ID NO 32
<211> LENGTH: 177
<212> TYPE: PRT
<213> ORGANISM: Hordeum Vulgare

<400> SEQUENCE: 32

```
Met Ala Pro Cys Pro Ser Val Lys Asn Ile Leu Val Leu Asp Ala Glu
1               5                   10                  15

Gly Lys Arg Val Ala Val Lys Tyr Tyr Ala Asp Asp Trp Pro Ser Ala
            20                  25                  30

Ser Ser Lys Met Ala Phe Glu Lys Ser Leu Phe Val Lys Thr Gln Lys
        35                  40                  45

Thr Ser Ala Arg Ala Glu Ala Asp Val Val Met Phe Asp Gly Tyr Ile
    50                  55                  60

Val Val Tyr Lys Phe Ile Gln Asp Leu His Phe Val Thr Gly Gly
65                  70                  75                  80

Asp Glu Glu Asn Glu Leu Ile Leu Ala Ser Val Leu Gln Gly Phe Ser
                85                  90                  95

Asp Ala Val Gly Val Leu Leu Arg Asn Asn Val Asp Lys Arg Thr Ala
            100                 105                 110

Leu Glu Asn Leu Asp Leu Ile Phe Leu Cys Leu Asp Glu Val Val Asp
        115                 120                 125

Gly Gly Ile Val Leu Glu Thr Asp Gly Asn Ala Ile Ala Glu Lys Val
    130                 135                 140

Ser Gly His Gly Leu Glu Gly Ala Gly Ser Phe Thr Glu Gln Thr Ile
145                 150                 155                 160

Ser Gln Ala Leu Ala Thr Ala Arg Glu His Phe Ala Arg Ser Leu Leu
                165                 170                 175

Lys
```

<210> SEQ ID NO 33
<211> LENGTH: 543
<212> TYPE: DNA
<213> ORGANISM: Medicago truncatula
<220> FEATURE:
<221> NAME/KEY: CDS
<222> LOCATION: (1)..(543)

<400> SEQUENCE: 33

```
atg gca tcc aac ggc ttg tgt cct tca ata aaa aac att ctt ctt tta    48
Met Ala Ser Asn Gly Leu Cys Pro Ser Ile Lys Asn Ile Leu Leu Leu
1               5                   10                  15 gac tct gaa ggg aag cgt gtg gca gtc aag tat tac tca gat gac tgg    96
Asp Ser Glu Gly Lys Arg Val Ala Val Lys Tyr Tyr Ser Asp Asp Trp
            20                  25                  30 ccg aca aac agt tca aag tta gct ttt gag aag ttt gtg ttc act aag   144
Pro Thr Asn Ser Ser Lys Leu Ala Phe Glu Lys Phe Val Phe Thr Lys
        35                  40                  45 act gtt aag aca aat gcg cgg aca gaa gct gag ata aca ctg ctt gag   192
Thr Val Lys Thr Asn Ala Arg Thr Glu Ala Glu Ile Thr Leu Leu Glu
    50                  55                  60
```

| | | |
|---|---|---|
| aac aat atc gtt gtt tac aaa ttt gtg caa gac ttg cat ttc ttt gtc<br>Asn Asn Ile Val Val Tyr Lys Phe Val Gln Asp Leu His Phe Phe Val<br>65                      70                    75                    80 | 240 |
| act ggt ggt gat gat gaa aat gag ctc att ttg tca tct gtt ctt caa<br>Thr Gly Gly Asp Asp Glu Asn Glu Leu Ile Leu Ser Ser Val Leu Gln<br>                      85                    90                    95 | 288 |
| ggt ttc ttt gat gca gtc acc ctt ttg ctg agg agc aat gtt gac aaa<br>Gly Phe Phe Asp Ala Val Thr Leu Leu Leu Arg Ser Asn Val Asp Lys<br>                  100                  105                  110 | 336 |
| agt gag gca ctt gag aac ttg gat ctc att ctt tta tgc ctt gat gag<br>Ser Glu Ala Leu Glu Asn Leu Asp Leu Ile Leu Leu Cys Leu Asp Glu<br>            115                  120                  125 | 384 |
| att gtt gat gga ggg att ata ctc gaa aca aat gga cct ctt atc gcc<br>Ile Val Asp Gly Gly Ile Ile Leu Glu Thr Asn Gly Pro Leu Ile Ala<br>130                      135                    140 | 432 |
| gaa aaa gtt acc tcc cac aac atg gat gct gat gct ccc tta tca gag<br>Glu Lys Val Thr Ser His Asn Met Asp Ala Asp Ala Pro Leu Ser Glu<br>145                      150                  155                  160 | 480 |
| cag aca cta act cag gca tgg gct aca gcc aga gac act ttc aca aga<br>Gln Thr Leu Thr Gln Ala Trp Ala Thr Ala Arg Asp Thr Phe Thr Arg<br>                  165                  170                  175 | 528 |
| act ctt tta aca tga<br>Thr Leu Leu Thr<br>                  180 | 543 |

<210> SEQ ID NO 34
<211> LENGTH: 180
<212> TYPE: PRT
<213> ORGANISM: Medicago truncatula

<400> SEQUENCE: 34

Met Ala Ser Asn Gly Leu Cys Pro Ser Ile Lys Asn Ile Leu Leu Leu
1               5                   10                  15

Asp Ser Glu Gly Lys Arg Val Ala Val Lys Tyr Tyr Ser Asp Asp Trp
            20                  25                  30

Pro Thr Asn Ser Ser Lys Leu Ala Phe Glu Lys Phe Val Phe Thr Lys
        35                  40                  45

Thr Val Lys Thr Asn Ala Arg Thr Glu Ala Glu Ile Thr Leu Leu Glu
    50                  55                  60

Asn Asn Ile Val Val Tyr Lys Phe Val Gln Asp Leu His Phe Phe Val
65                  70                  75                  80

Thr Gly Gly Asp Asp Glu Asn Glu Leu Ile Leu Ser Ser Val Leu Gln
                85                  90                  95

Gly Phe Phe Asp Ala Val Thr Leu Leu Leu Arg Ser Asn Val Asp Lys
            100                 105                 110

Ser Glu Ala Leu Glu Asn Leu Asp Leu Ile Leu Leu Cys Leu Asp Glu
        115                 120                 125

Ile Val Asp Gly Gly Ile Ile Leu Glu Thr Asn Gly Pro Leu Ile Ala
    130                 135                 140

Glu Lys Val Thr Ser His Asn Met Asp Ala Asp Ala Pro Leu Ser Glu
145                 150                 155                 160

Gln Thr Leu Thr Gln Ala Trp Ala Thr Ala Arg Asp Thr Phe Thr Arg
                165                 170                 175

Thr Leu Leu Thr
            180

<210> SEQ ID NO 35

```
<211> LENGTH: 561
<212> TYPE: DNA
<213> ORGANISM: Chlorella variabilis
<220> FEATURE:
<221> NAME/KEY: CDS
<222> LOCATION: (1)..(561)

<400> SEQUENCE: 35 atg gcg gcg gaa ata gtc gac ccc act ata ccc gtt gtg aaa aac atg        48
Met Ala Ala Glu Ile Val Asp Pro Thr Ile Pro Val Val Lys Asn Met
1               5                   10                  15 ctg ctg ctg gac tcg gag ggc aag cgg att gcg gtc aag tac ttc acg        96
Leu Leu Leu Asp Ser Glu Gly Lys Arg Ile Ala Val Lys Tyr Phe Thr
            20                  25                  30 ccc gag atg tac agc gtc acg gca cag gcc aac tac gag aag tcg gtc       144
Pro Glu Met Tyr Ser Val Thr Ala Gln Ala Asn Tyr Glu Lys Ser Val
        35                  40                  45 ttt gcc aag acg tcg cgg aca aat gcg cgg gga gag gcc gag atc atc       192
Phe Ala Lys Thr Ser Arg Thr Asn Ala Arg Gly Glu Ala Glu Ile Ile
    50                  55                  60 atg ttt gac gac gtg gtg gtg gtg tac aag ttc ctg ggg gat ctc atg       240
Met Phe Asp Asp Val Val Val Val Tyr Lys Phe Leu Gly Asp Leu Met
65                  70                  75                  80 ttc tac gtg acg gga gac cag gac gag aac gag gtg gtg ctg tac agc       288
Phe Tyr Val Thr Gly Asp Gln Asp Glu Asn Glu Val Val Leu Tyr Ser
                85                  90                  95 gtg ctg caa gcc ttc tac gaa tcc atc aac atg ctg ctc agg aat gct       336
Val Leu Gln Ala Phe Tyr Glu Ser Ile Asn Met Leu Leu Arg Asn Ala
            100                 105                 110 gtg gag aag aag acg gtg ctg gag aac ctg gac ctg gtg ctg ctg gcc       384
Val Glu Lys Lys Thr Val Leu Glu Asn Leu Asp Leu Val Leu Leu Ala
        115                 120                 125 atg gac gaa atc gtg gat ggg ggc ctc atc ctg gag acc gat gcg ggg       432
Met Asp Glu Ile Val Asp Gly Gly Leu Ile Leu Glu Thr Asp Ala Gly
    130                 135                 140 gtg gtg gcc acg cgc gtg acg atg cgc cag gat ggc gag ggc agc ccc       480
Val Val Ala Thr Arg Val Thr Met Arg Gln Asp Gly Glu Gly Ser Pro
145                 150                 155                 160 atg agc aac ccc ggg ctg gtg acg ctg tcg caa gcc ttt ggg tcc atc       528
Met Ser Asn Pro Gly Leu Val Thr Leu Ser Gln Ala Phe Gly Ser Ile
                165                 170                 175 aag gag cag gtg gcg cgg agc ctg ctc aag tga                           561
Lys Glu Gln Val Ala Arg Ser Leu Leu Lys
            180                 185

<210> SEQ ID NO 36
<211> LENGTH: 186
<212> TYPE: PRT
<213> ORGANISM: Chlorella variabilis

<400> SEQUENCE: 36

Met Ala Ala Glu Ile Val Asp Pro Thr Ile Pro Val Val Lys Asn Met
1               5                   10                  15

Leu Leu Leu Asp Ser Glu Gly Lys Arg Ile Ala Val Lys Tyr Phe Thr
            20                  25                  30

Pro Glu Met Tyr Ser Val Thr Ala Gln Ala Asn Tyr Glu Lys Ser Val
        35                  40                  45

Phe Ala Lys Thr Ser Arg Thr Asn Ala Arg Gly Glu Ala Glu Ile Ile
    50                  55                  60

Met Phe Asp Asp Val Val Val Val Tyr Lys Phe Leu Gly Asp Leu Met
65                  70                  75                  80
```

```
Phe Tyr Val Thr Gly Asp Gln Asp Glu Asn Glu Val Val Leu Tyr Ser
                85                  90                  95

Val Leu Gln Ala Phe Tyr Glu Ser Ile Asn Met Leu Leu Arg Asn Ala
            100                 105                 110

Val Glu Lys Lys Thr Val Leu Glu Asn Leu Asp Leu Val Leu Leu Ala
        115                 120                 125

Met Asp Glu Ile Val Asp Gly Gly Leu Ile Leu Glu Thr Asp Ala Gly
130                 135                 140

Val Val Ala Thr Arg Val Thr Met Arg Gln Asp Gly Glu Gly Ser Pro
145                 150                 155                 160

Met Ser Asn Pro Gly Leu Val Thr Leu Ser Gln Ala Phe Gly Ser Ile
                165                 170                 175

Lys Glu Gln Val Ala Arg Ser Leu Leu Lys
            180                 185

<210> SEQ ID NO 37
<211> LENGTH: 1196
<212> TYPE: DNA
<213> ORGANISM: Coccomyxa subellipsoidea
<220> FEATURE:
<221> NAME/KEY: CDS
<222> LOCATION: (201)..(749)

<400> SEQUENCE: 37
gacaaatttg caatccagag cgtgctattt tcttgaaagt tggacacacc attccaatta      60
attccatttg ttcagggtgt tgcagactga tgaacccaat cacttgtctc cgagcgcccc    120
tggcacccct catttacct  taaaagccta atatctctga acatcggt  tttaaaagcg     180 ataagtaggc gcaaggttca atg gca gat att gtg gac cca act gtt ccg gtg   233
                        Met Ala Asp Ile Val Asp Pro Thr Val Pro Val
                          1               5                  10 gtg aaa aac atg ctt ttg ttg gat tct gag ggg aag cgt att gcc gtt    281
Val Lys Asn Met Leu Leu Leu Asp Ser Glu Gly Lys Arg Ile Ala Val
            15                  20                  25 aaa tac tat ggg agc gac tgg cct acc gtg aat gcg cag gcc acg tac    329
Lys Tyr Tyr Gly Ser Asp Trp Pro Thr Val Asn Ala Gln Ala Thr Tyr
        30                  35                  40 gag aag tct gtc ttc gca aaa aca aac aga acc ctg gcg aga ggt gaa    377
Glu Lys Ser Val Phe Ala Lys Thr Asn Arg Thr Leu Ala Arg Gly Glu
    45                  50                  55 gct gag atc acc atg ttt gac gat gtg atc gtc gtc tac aag ttc att    425
Ala Glu Ile Thr Met Phe Asp Asp Val Ile Val Val Tyr Lys Phe Ile
60                  65                  70                  75 ggg gac ctc atg ttc ttc gtc act gga tca caa gac gag aac gag ctc    473
Gly Asp Leu Met Phe Phe Val Thr Gly Ser Gln Asp Glu Asn Glu Leu
                80                  85                  90 atc ctg tgc caa gtg ctc cag gga ttt tat gag tcc ata tca ctg ctg    521
Ile Leu Cys Gln Val Leu Gln Gly Phe Tyr Glu Ser Ile Ser Leu Leu
            95                 100                 105 ctc agg agc gct gtg gag aag aag aca gtt ttg gag aac ctg gac ttg    569
Leu Arg Ser Ala Val Glu Lys Lys Thr Val Leu Glu Asn Leu Asp Leu
        110                 115                 120 gtc ctc ctg gta atg gat gag act gtg gat ggc ggg ctc atc ctg gag    617
Val Leu Leu Val Met Asp Glu Thr Val Asp Gly Gly Leu Ile Leu Glu
    125                 130                 135 act gac cct gct acc att gcc agc cga gta gca atg cgg ggt ccg gac    665
Thr Asp Pro Ala Thr Ile Ala Ser Arg Val Ala Met Arg Gly Pro Asp
140                 145                 150                 155
```

```
gac aat cta tcc ctc aca gag cag act ttc tcc agg gcc ctt gca aca    713
Asp Asn Leu Ser Leu Thr Glu Gln Thr Phe Ser Arg Ala Leu Ala Thr
        160                 165                 170 gcg aag gaa cag ctg gca cgg tcc ttg ttg aag tga ctttggctgc         759
Ala Lys Glu Gln Leu Ala Arg Ser Leu Leu Lys
    175                 180 cattcgcggg ccatgatggc atagttacag agcatgattg tgcttgcaaa gctgctcaaa  819
tggttaggct gttatggtga cgggaactca ttgcaatgtc tttaccgtac cagcaaagta  879
tatcacagat tgtgatcacc acatttcgag ctttttgtga ggctgggcag tctgcaactc  939
gccaaatttg ccatttatgg cctagttggc ccaaggggca ggaagactgt ggaaattctt  999
tttgtcgttg aaagtagtca gcagatatat gcaatgagca ctggatgcta ttactgggtt  1059
ggtgttccta atgccacatc ctctgatatt tccaggaaac agagattaat gtctctgcag  1119
tgtgaagtgt gcacacagca ggggatgctg cgcacatgcc tcttgcacat gcacatgtga  1179
cgtacgatga tttcatc                                                1196

<210> SEQ ID NO 38
<211> LENGTH: 182
<212> TYPE: PRT
<213> ORGANISM: Coccomyxa subellipsoidea

<400> SEQUENCE: 38

Met Ala Asp Ile Val Asp Pro Thr Val Pro Val Val Lys Asn Met Leu
1               5                   10                  15

Leu Leu Asp Ser Glu Gly Lys Arg Ile Ala Val Lys Tyr Tyr Gly Ser
            20                  25                  30

Asp Trp Pro Thr Val Asn Ala Gln Ala Thr Tyr Glu Lys Ser Val Phe
        35                  40                  45

Ala Lys Thr Asn Arg Thr Leu Ala Arg Gly Glu Ala Glu Ile Thr Met
    50                  55                  60

Phe Asp Asp Val Ile Val Val Tyr Lys Phe Ile Gly Asp Leu Met Phe
65                  70                  75                  80

Phe Val Thr Gly Ser Gln Asp Glu Asn Glu Leu Ile Leu Cys Gln Val
                85                  90                  95

Leu Gln Gly Phe Tyr Glu Ser Ile Ser Leu Leu Arg Ser Ala Val
            100                 105                 110

Glu Lys Lys Thr Val Leu Glu Asn Leu Asp Leu Val Leu Leu Val Met
        115                 120                 125

Asp Glu Thr Val Asp Gly Gly Leu Ile Leu Glu Thr Asp Pro Ala Thr
    130                 135                 140

Ile Ala Ser Arg Val Ala Met Arg Gly Pro Asp Asp Asn Leu Ser Leu
145                 150                 155                 160

Thr Glu Gln Thr Phe Ser Arg Ala Leu Ala Thr Ala Lys Glu Gln Leu
                165                 170                 175

Ala Arg Ser Leu Leu Lys
            180

<210> SEQ ID NO 39
<211> LENGTH: 961
<212> TYPE: DNA
<213> ORGANISM: Oryza sativa
<220> FEATURE:
<221> NAME/KEY: CDS
<222> LOCATION: (215)..(763)

<400> SEQUENCE: 39
```

```
gcgccgatct ccatctcgcg actcgcgagc agagcagggt tggtaggggc gcccatctcc      60
atccggcgag cagagcagag cggaggaggt gcgccatcgt cccgctgcat cctgttttga     120
gcctggatct tgccaaacaa gtggttgatc ttactgcttt cggtggccgt gtctcctcca     180
caggaaggaa ggcaccgggg atctagagga ggcc atg gga gaa ttc tcc aag gaa     235
                                      Met Gly Glu Phe Ser Lys Glu
                                       1               5 tct tgc cct tct gtg aag aac att ttg ctt ctg gat tct gaa ggg aaa       283
Ser Cys Pro Ser Val Lys Asn Ile Leu Leu Leu Asp Ser Glu Gly Lys
            10                  15                  20 cgt gtt gcc gtg aaa tac ttc tcg gat gat tgg tct agt aat gcg tca       331
Arg Val Ala Val Lys Tyr Phe Ser Asp Asp Trp Ser Ser Asn Ala Ser
 25                  30                  35 aag ttg gcc ttt gaa aag tct gtc ttt act aaa act ctg aag aca aat       379
Lys Leu Ala Phe Glu Lys Ser Val Phe Thr Lys Thr Leu Lys Thr Asn
 40                  45                  50                  55 gca cgc tca gaa gct gag ata aca ttg ttt gat ggc tat att gtc gtt       427
Ala Arg Ser Glu Ala Glu Ile Thr Leu Phe Asp Gly Tyr Ile Val Val
                 60                  65                  70 tat aag ttt gta caa gac ctt cat ttt ttt gtc acc gct ggt gat gat       475
Tyr Lys Phe Val Gln Asp Leu His Phe Phe Val Thr Ala Gly Asp Asp
             75                  80                  85 gag aat gag ctc att ata gca aat gta cta cag ggc ttc tct gat tct       523
Glu Asn Glu Leu Ile Ile Ala Asn Val Leu Gln Gly Phe Ser Asp Ser
         90                  95                 100 gtt ggt ctt tta ctc agg ggt gat gtt gag aag agg act gca ctc gag       571
Val Gly Leu Leu Leu Arg Gly Asp Val Glu Lys Arg Thr Ala Leu Glu
    105                 110                 115 aat ctg gac ttg ata ctt ctc tgc atc gat gaa att gta gat ggc ggc       619
Asn Leu Asp Leu Ile Leu Leu Cys Ile Asp Glu Ile Val Asp Gly Gly
120                 125                 130                 135 ata att ctg gaa aca gat gca aat acc att gcc ggg aag gtt gca acc       667
Ile Ile Leu Glu Thr Asp Ala Asn Thr Ile Ala Gly Lys Val Ala Thr
                140                 145                 150 aat gct gtt gat ggt tct gcc ccc ttc tct gag cag acg ata tct cag       715
Asn Ala Val Asp Gly Ser Ala Pro Phe Ser Glu Gln Thr Ile Ser Gln
            155                 160                 165 gct tta gcc act gct agg gag cac ctt gca aga tct ctg ctc aag taa       763
Ala Leu Ala Thr Ala Arg Glu His Leu Ala Arg Ser Leu Leu Lys
        170                 175                 180 atcatttatc ttttgactcc ttaaaacttc tctgcgttga ggattgggcg agtgtacgtt     823
gaagcatgta attgttacct tttactcata ataaagtgta attgtgacgg aaaaaatagt     883
tgaatatgat ataatacttg tactcagatt tatctcatca agtgctaatg atagtttcca     943
tgattgcttc tgcgttgc                                                    961

<210> SEQ ID NO 40
<211> LENGTH: 182
<212> TYPE: PRT
<213> ORGANISM: Oryza sativa

<400> SEQUENCE: 40

Met Gly Glu Phe Ser Lys Glu Ser Cys Pro Ser Val Lys Asn Ile Leu
  1               5                  10                  15

Leu Leu Asp Ser Glu Gly Lys Arg Val Ala Val Lys Tyr Phe Ser Asp
             20                  25                  30

Asp Trp Ser Ser Asn Ala Ser Lys Leu Ala Phe Glu Lys Ser Val Phe
         35                  40                  45
```

```
Thr Lys Thr Leu Lys Thr Asn Ala Arg Ser Glu Ala Glu Ile Thr Leu
    50                  55                  60
Phe Asp Gly Tyr Ile Val Val Tyr Lys Phe Val Gln Asp Leu His Phe
 65                  70                  75                  80
Phe Val Thr Ala Gly Asp Asp Glu Asn Glu Leu Ile Ile Ala Asn Val
                 85                  90                  95
Leu Gln Gly Phe Ser Asp Ser Val Gly Leu Leu Arg Gly Asp Val
            100                 105                 110
Glu Lys Arg Thr Ala Leu Glu Asn Leu Asp Leu Ile Leu Leu Cys Ile
            115                 120                 125
Asp Glu Ile Val Asp Gly Gly Ile Ile Leu Glu Thr Asp Ala Asn Thr
    130                 135                 140
Ile Ala Gly Lys Val Ala Thr Asn Ala Val Asp Gly Ser Ala Pro Phe
145                 150                 155                 160
Ser Glu Gln Thr Ile Ser Gln Ala Leu Ala Thr Ala Arg Glu His Leu
                165                 170                 175
Ala Arg Ser Leu Leu Lys
            180

<210> SEQ ID NO 41
<211> LENGTH: 797
<212> TYPE: DNA
<213> ORGANISM: Solanum lycopersicum
<220> FEATURE:
<221> NAME/KEY: CDS
<222> LOCATION: (51)..(605)

<400> SEQUENCE: 41
ctgcaaatca acaaaaagaa aaattccggc ggtgaatcgc tatttcatca atg gcg      56
                                                         Met Ala
                                                           1 ggt ttc ctt cta aat tat gat tct tgt cct gtg gtg aag aac ata ctt   104
Gly Phe Leu Leu Asn Tyr Asp Ser Cys Pro Val Val Lys Asn Ile Leu
         5                  10                  15 ctt ttg gat tcg gaa gga aag cgt gta gct gtt aaa tac tac tct gat   152
Leu Leu Asp Ser Glu Gly Lys Arg Val Ala Val Lys Tyr Tyr Ser Asp
     20                  25                  30 gac tgg ccg aca aac aac gct aag gtt gcg ttc gaa aaa tct att ttc   200
Asp Trp Pro Thr Asn Asn Ala Lys Val Ala Phe Glu Lys Ser Ile Phe
 35                  40                  45                  50 acc aag act caa aag aca aat gct cgg act gaa gct gaa ata aca atg   248
Thr Lys Thr Gln Lys Thr Asn Ala Arg Thr Glu Ala Glu Ile Thr Met
             55                  60                  65 ttc gag aac aac att att gtc tat aag ttt gtg caa gac ctc cat ttc   296
Phe Glu Asn Asn Ile Ile Val Tyr Lys Phe Val Gln Asp Leu His Phe
         70                  75                  80 ttt gtc act ggg ggt gat gat gaa aat gaa cta gtt cta gcc act gtt   344
Phe Val Thr Gly Gly Asp Asp Glu Asn Glu Leu Val Leu Ala Thr Val
     85                  90                  95 ctt cag ggt ttc tat gat gca gtt acc ctt ctc cta agg aat aat gtt   392
Leu Gln Gly Phe Tyr Asp Ala Val Thr Leu Leu Leu Arg Asn Asn Val
            100                 105                 110 gac cag aga gag gca ctt gag aat tta gat ctc att ctt cta tgc ctt   440
Asp Gln Arg Glu Ala Leu Glu Asn Leu Asp Leu Ile Leu Leu Cys Leu
115                 120                 125                 130 gat gag att gtg gat ggc ggg atg gta ctt gaa act gat ggt aat act   488
Asp Glu Ile Val Asp Gly Gly Met Val Leu Glu Thr Asp Gly Asn Thr
                135                 140                 145 att gct gga aaa gtt tcg agt cat aac atg gat gat gga gca ccc ttg   536
```

```
Ile Ala Gly Lys Val Ser Ser His Asn Met Asp Asp Gly Ala Pro Leu
            150                 155                 160 tct gaa caa aca ata act caa gca ttg gca aca gcg cgc gaa cat ttg      584
Ser Glu Gln Thr Ile Thr Gln Ala Leu Ala Thr Ala Arg Glu His Leu
        165                 170                 175 aca aga tct ctt cta aga tga aaaaagtttg gagagagcaa ttatttttg          635
Thr Arg Ser Leu Leu Arg
    180 acgtaattct ttatgctcat atacctgtag ttattttat ttcagatggt gatgattgcg     695 tattcgtaga gtcagttatt ttataccatt tataatcttc tgttgcctgt actatcttgt    755 aagatgagga tatccttatt gcattttgga tcaaaaaaaa aa                       797

<210> SEQ ID NO 42
<211> LENGTH: 184
<212> TYPE: PRT
<213> ORGANISM: Solanum lycopersicum

<400> SEQUENCE: 42

Met Ala Gly Phe Leu Leu Asn Tyr Asp Ser Cys Pro Val Val Lys Asn
1               5                   10                  15

Ile Leu Leu Leu Asp Ser Glu Gly Lys Arg Val Ala Val Lys Tyr Tyr
            20                  25                  30

Ser Asp Asp Trp Pro Thr Asn Asn Ala Lys Val Ala Phe Glu Lys Ser
        35                  40                  45

Ile Phe Thr Lys Thr Gln Lys Thr Asn Ala Arg Thr Glu Ala Glu Ile
    50                  55                  60

Thr Met Phe Glu Asn Asn Ile Ile Val Tyr Lys Phe Val Gln Asp Leu
65                  70                  75                  80

His Phe Phe Val Thr Gly Gly Asp Asp Glu Asn Glu Leu Val Leu Ala
                85                  90                  95

Thr Val Leu Gln Gly Phe Tyr Asp Ala Val Thr Leu Leu Leu Arg Asn
            100                 105                 110

Asn Val Asp Gln Arg Glu Ala Leu Glu Asn Leu Asp Leu Ile Leu Leu
        115                 120                 125

Cys Leu Asp Glu Ile Val Asp Gly Gly Met Val Leu Glu Thr Asp Gly
    130                 135                 140

Asn Thr Ile Ala Gly Lys Val Ser Ser His Asn Met Asp Asp Gly Ala
145                 150                 155                 160

Pro Leu Ser Glu Gln Thr Ile Thr Gln Ala Leu Ala Thr Ala Arg Glu
                165                 170                 175

His Leu Thr Arg Ser Leu Leu Arg
            180

<210> SEQ ID NO 43
<211> LENGTH: 862
<212> TYPE: DNA
<213> ORGANISM: Solanum lycopersicum
<220> FEATURE:
<221> NAME/KEY: CDS
<222> LOCATION: (58)..(609)

<400> SEQUENCE: 43
gtttgagctt ccaaatcaag aaggatcaac aatttctgta aatcccttgt tccatca       57 atg gcg ttt cct ctc cat tac ggt tct tgc cct gtg gta aag aat ata     105
Met Ala Phe Pro Leu His Tyr Gly Ser Cys Pro Val Val Lys Asn Ile
1               5                   10                  15 ctt ctt ttg gat tct gaa gga aaa cgt gta gcg gta aaa tac tac tgt     153
```

| | | | | | | | | | | | | | | |
|---|---|---|---|---|---|---|---|---|---|---|---|---|---|---|
| Leu | Leu | Leu | Asp | Ser | Glu | Gly | Lys | Arg | Val | Ala | Val | Lys | Tyr | Cys |
| | | | 20 | | | | 25 | | | | | 30 | | |

```
gat gac tgg cca aca tac agt gcc aag ctt gca ttt gag aag tca att    201
Asp Asp Trp Pro Thr Tyr Ser Ala Lys Leu Ala Phe Glu Lys Ser Ile
            35                  40                  45 ttt acc aag act cag aag aca aat gct cga act gaa gct gag ata gca    249
Phe Thr Lys Thr Gln Lys Thr Asn Ala Arg Thr Glu Ala Glu Ile Ala
 50                  55                  60 atg ttt gac agt aac att gtt gtc tat aag ttt gtg caa gac ctt cac    297
Met Phe Asp Ser Asn Ile Val Val Tyr Lys Phe Val Gln Asp Leu His
 65                  70                  75                  80 ttt ttt gtg acg gga ggt gat gat gaa aat gaa cta att cta gcc act    345
Phe Phe Val Thr Gly Gly Asp Asp Glu Asn Glu Leu Ile Leu Ala Thr
                 85                  90                  95 gtt ctc cag ggc ttc tat gat gca gtt acc ctt tta ctc agg agt aat    393
Val Leu Gln Gly Phe Tyr Asp Ala Val Thr Leu Leu Leu Arg Ser Asn
            100                 105                 110 gtt gaa cag agg gag gct ctt gag aac ttg gat ttg att ctt ctg tgc    441
Val Glu Gln Arg Glu Ala Leu Glu Asn Leu Asp Leu Ile Leu Leu Cys
        115                 120                 125 ttg gat gag att gtg gat gga ggg atg att ctt gaa aca gat ggt agt    489
Leu Asp Glu Ile Val Asp Gly Gly Met Ile Leu Glu Thr Asp Gly Ser
130                 135                 140 gtc att gcc ggc aaa gtt gcc agt cat aat atg gat gat ggg tca ccc    537
Val Ile Ala Gly Lys Val Ala Ser His Asn Met Asp Asp Gly Ser Pro
145                 150                 155                 160 att tcc gag cag aca atc agt caa gct ttg gca aca gct cgt gaa cat    585
Ile Ser Glu Gln Thr Ile Ser Gln Ala Leu Ala Thr Ala Arg Glu His
                165                 170                 175 ttg aca cga tca ctt ctc aga tga agcatctcaa tgcttgtgaa aagagatgaa   639
Leu Thr Arg Ser Leu Leu Arg
            180 tcgagcttca ttctttagaa gtatcgtccc caaatcattt tagatgtttt ttccttcagg  699 atggaaatgt tgtccaccgt tgatcaagtt tattcgcgtt ataaattcat agaatgtcct  759 ctttctgtta atttttaattc tttatgctcc aaacattgga tattaccagt atattacaca  819 ttgacattgt tatagaggtt ttgacaattc aataaaaaaa aaa                    862
```

<210> SEQ ID NO 44
<211> LENGTH: 183
<212> TYPE: PRT
<213> ORGANISM: Solanum lycopersicum

<400> SEQUENCE: 44

| | | | | | | | | | | | | | | |
|---|---|---|---|---|---|---|---|---|---|---|---|---|---|---|
| Met | Ala | Phe | Pro | Leu | His | Tyr | Gly | Ser | Cys | Pro | Val | Val | Lys | Asn | Ile |
| 1 | | | | 5 | | | | | 10 | | | | | 15 | |

| | | | | | | | | | | | | | | |
|---|---|---|---|---|---|---|---|---|---|---|---|---|---|---|
| Leu | Leu | Leu | Asp | Ser | Glu | Gly | Lys | Arg | Val | Ala | Val | Lys | Tyr | Cys |
| | | | 20 | | | | 25 | | | | | 30 | | |

| | | | | | | | | | | | | | | |
|---|---|---|---|---|---|---|---|---|---|---|---|---|---|---|
| Asp | Asp | Trp | Pro | Thr | Tyr | Ser | Ala | Lys | Leu | Ala | Phe | Glu | Lys | Ser | Ile |
| | | | 35 | | | | 40 | | | | | 45 | | | |

| | | | | | | | | | | | | | | |
|---|---|---|---|---|---|---|---|---|---|---|---|---|---|---|
| Phe | Thr | Lys | Thr | Gln | Lys | Thr | Asn | Ala | Arg | Thr | Glu | Ala | Glu | Ile | Ala |
| 50 | | | | | 55 | | | | | 60 | | | | | |

| | | | | | | | | | | | | | | |
|---|---|---|---|---|---|---|---|---|---|---|---|---|---|---|
| Met | Phe | Asp | Ser | Asn | Ile | Val | Val | Tyr | Lys | Phe | Val | Gln | Asp | Leu | His |
| 65 | | | | | 70 | | | | | 75 | | | | | 80 |

| | | | | | | | | | | | | | | |
|---|---|---|---|---|---|---|---|---|---|---|---|---|---|---|
| Phe | Phe | Val | Thr | Gly | Gly | Asp | Asp | Glu | Asn | Glu | Leu | Ile | Leu | Ala | Thr |
| | | | | 85 | | | | | 90 | | | | | 95 | |

| | | | | | | | | | | | | | | |
|---|---|---|---|---|---|---|---|---|---|---|---|---|---|---|
| Val | Leu | Gln | Gly | Phe | Tyr | Asp | Ala | Val | Thr | Leu | Leu | Leu | Arg | Ser | Asn |
| | | | 100 | | | | | 105 | | | | | 110 | | |

```
Val Glu Gln Arg Glu Ala Leu Glu Asn Leu Asp Leu Ile Leu Leu Cys
        115                 120                 125

Leu Asp Glu Ile Val Asp Gly Gly Met Ile Leu Glu Thr Asp Gly Ser
130                 135                 140

Val Ile Ala Gly Lys Val Ala Ser His Asn Met Asp Asp Gly Ser Pro
145                 150                 155                 160

Ile Ser Glu Gln Thr Ile Ser Gln Ala Leu Ala Thr Ala Arg Glu His
                165                 170                 175

Leu Thr Arg Ser Leu Leu Arg
        180
```

<210> SEQ ID NO 45
<211> LENGTH: 767
<212> TYPE: DNA
<213> ORGANISM: Glycine max
<220> FEATURE:
<221> NAME/KEY: CDS
<222> LOCATION: (56)..(598)

<400> SEQUENCE: 45

```
ggattacaga tcttccaaac ttcagagcgc aggcaaacaa cttcttctct cagac atg      58
                                                              Met
                                                              1 gca tct caa ggt ttg tgt cct tcg ata aaa aat att ctt ctt ttg gac     106
Ala Ser Gln Gly Leu Cys Pro Ser Ile Lys Asn Ile Leu Leu Leu Asp
         5                  10                  15 tct gaa ggg aag cgt gtg gca gtc aag tat tac tca gat gac tgg cca     154
Ser Glu Gly Lys Arg Val Ala Val Lys Tyr Tyr Ser Asp Asp Trp Pro
     20                  25                  30 aca aac aat gca aag tta gct ttt gag aag ttt gta ttt acc aag act     202
Thr Asn Asn Ala Lys Leu Ala Phe Glu Lys Phe Val Phe Thr Lys Thr
 35                  40                  45 gtt aag aca aat gct cgt aca gaa gct gag gta aca cta ctt gag aac     250
Val Lys Thr Asn Ala Arg Thr Glu Ala Glu Val Thr Leu Leu Glu Asn
 50                  55                  60                  65 aat atc att att tac aaa ttt gta caa gac ctg cat ttt ttt gtc act     298
Asn Ile Ile Ile Tyr Lys Phe Val Gln Asp Leu His Phe Phe Val Thr
                 70                  75                  80 ggt ggt gaa gat gaa aat gag ctc att cta gca tca gtt ctt caa ggt     346
Gly Gly Glu Asp Glu Asn Glu Leu Ile Leu Ala Ser Val Leu Gln Gly
             85                  90                  95 ttc ttt gat gca gtc act ctt ctg ttg agg agc aat gtt gac aaa aga     394
Phe Phe Asp Ala Val Thr Leu Leu Leu Arg Ser Asn Val Asp Lys Arg
         100                 105                 110 gag gca ctt gag aac ttg gat ctc att ctc ttg tgt ctt gac gag att     442
Glu Ala Leu Glu Asn Leu Asp Leu Ile Leu Leu Cys Leu Asp Glu Ile
     115                 120                 125 gtt gat gga ggg atg ata ctt gaa aca aat gga cct ctt att gct gaa     490
Val Asp Gly Gly Met Ile Leu Glu Thr Asn Gly Pro Leu Ile Ala Glu
130                 135                 140                 145 aaa gtg acc tct cat agc ttg gat gct gat gcc ccc ttg tca gag cag     538
Lys Val Thr Ser His Ser Leu Asp Ala Asp Ala Pro Leu Ser Glu Gln
                 150                 155                 160 aca tta act caa gcc tgg gct acg gcc aga gaa cat ttg aca aga acc     586
Thr Leu Thr Gln Ala Trp Ala Thr Ala Arg Glu His Leu Thr Arg Thr
             165                 170                 175 ctt tta aaa tga tgtttgcata cactgaaaat gagctactta tagtcgaata         638
Leu Leu Lys
        180
```

```
tccaattttt ttgtctgtta atgggagttg tttcatcccc cattgcgagt tattgtaatg    698
agcaccatac cattttttctg aaaagtgtgt tccgcgtgca tcttagctat tatttgtcaa    758
attcgtgga                                                             767
```

<210> SEQ ID NO 46
<211> LENGTH: 180
<212> TYPE: PRT
<213> ORGANISM: Glycine max

<400> SEQUENCE: 46

```
Met Ala Ser Gln Gly Leu Cys Pro Ser Ile Lys Asn Ile Leu Leu Leu
1               5                   10                  15

Asp Ser Glu Gly Lys Arg Val Ala Val Lys Tyr Tyr Ser Asp Asp Trp
                20                  25                  30

Pro Thr Asn Asn Ala Lys Leu Ala Phe Glu Lys Phe Val Phe Thr Lys
            35                  40                  45

Thr Val Lys Thr Asn Ala Arg Thr Glu Ala Glu Val Thr Leu Leu Glu
        50                  55                  60

Asn Asn Ile Ile Ile Tyr Lys Phe Val Gln Asp Leu His Phe Phe Val
65                  70                  75                  80

Thr Gly Gly Glu Asp Glu Asn Glu Leu Ile Leu Ala Ser Val Leu Gln
                85                  90                  95

Gly Phe Phe Asp Ala Val Thr Leu Leu Leu Arg Ser Asn Val Asp Lys
            100                 105                 110

Arg Glu Ala Leu Glu Asn Leu Asp Leu Ile Leu Leu Cys Leu Asp Glu
        115                 120                 125

Ile Val Asp Gly Gly Met Ile Leu Glu Thr Asn Gly Pro Leu Ile Ala
    130                 135                 140

Glu Lys Val Thr Ser His Ser Leu Asp Ala Asp Ala Pro Leu Ser Glu
145                 150                 155                 160

Gln Thr Leu Thr Gln Ala Trp Ala Thr Ala Arg Glu His Leu Thr Arg
                165                 170                 175

Thr Leu Leu Lys
            180
```

<210> SEQ ID NO 47
<211> LENGTH: 805
<212> TYPE: DNA
<213> ORGANISM: Chlamydomonas reinhardtii
<220> FEATURE:
<221> NAME/KEY: CDS
<222> LOCATION: (123)..(677)

<400> SEQUENCE: 47

```
aattatttcc cctgacacag tataatagag ctagaggctt ttttgtcttg tccttttccaa    60 ccgcgactga acttgtcgtc acagctgcgt taaccagccc agcgtgggct ctgacagcta   120 aa atg gca ggc atc gat ccg act ctt cca atc gtt aag aac ctg ctg      167
   Met Ala Gly Ile Asp Pro Thr Leu Pro Ile Val Lys Asn Leu Leu
   1               5                   10                  15 ctg ctt gac tcg gag ggc aag cgc atc gcc gtc aag tat tac acg cca     215
Leu Leu Asp Ser Glu Gly Lys Arg Ile Ala Val Lys Tyr Tyr Thr Pro
                20                  25                  30 gag tgg tcc acg gtc gcg agc cag gcc agc ttt gag aag gcg ctg tgg     263
Glu Trp Ser Thr Val Ala Ser Gln Ala Ser Phe Glu Lys Ala Leu Trp
            35                  40                  45 aac aag acc agc cgg acc aat gcg cgc gcg gag gct gag att atc atg     311
Asn Lys Thr Ser Arg Thr Asn Ala Arg Ala Glu Ala Glu Ile Ile Met
```

```
                    50                    55                    60
ttt gac aac gtc gtg gtc gtg tac aag tac att ggc gac ctg atg ttc      359
Phe Asp Asn Val Val Val Val Tyr Lys Tyr Ile Gly Asp Leu Met Phe
 65                  70                  75 tac gtg acg ggc agc ctg gat gag aac gag ctg att ctc tac acc gtg      407
Tyr Val Thr Gly Ser Leu Asp Glu Asn Glu Leu Ile Leu Tyr Thr Val
 80                  85                  90                  95 cta caa gcg ttc tac gag tcg gtg acc atc ctc ttg aga caa caa gtg      455
Leu Gln Ala Phe Tyr Glu Ser Val Thr Ile Leu Leu Arg Gln Gln Val
                    100                 105                 110 gag aag aag acg gtg ctt gaa aac ctg gac ctg gtg ctg ctg gcc atg      503
Glu Lys Lys Thr Val Leu Glu Asn Leu Asp Leu Val Leu Leu Ala Met
             115                 120                 125 gat gag att gtg gac ggc ggc att atc ctg gag acg gag ccg gcc atg      551
Asp Glu Ile Val Asp Gly Gly Ile Ile Leu Glu Thr Glu Pro Ala Met
         130                 135                 140 att gcc tcg cgg gta acc atg cgc ggc gcg gac ggc gag cag gcg ccc      599
Ile Ala Ser Arg Val Thr Met Arg Gly Ala Asp Gly Glu Gln Ala Pro
     145                 150                 155 gtg ccc atc acg gag cag aca ttc tcc aag gcg ctg gca tcc gca aag      647
Val Pro Ile Thr Glu Gln Thr Phe Ser Lys Ala Leu Ala Ser Ala Lys
160                 165                 170                 175 gag cac ctg gcg cgc tcg ctc ctc aag taa agcagcagcc gtagcggctg         697
Glu His Leu Ala Arg Ser Leu Leu Lys
                    180 caggagccgg cacgctgggg agtatggagg actggaagga gcggaggagg cggaggcagc      757 ggcccatgtg gcgcaaggcg attcaggtca agggagggtg gaggaagg                   805

<210> SEQ ID NO 48
<211> LENGTH: 184
<212> TYPE: PRT
<213> ORGANISM: Chlamydomonas reinhardtii

<400> SEQUENCE: 48

Met Ala Gly Ile Asp Pro Thr Leu Pro Ile Val Lys Asn Leu Leu Leu
 1               5                  10                  15

Leu Asp Ser Glu Gly Lys Arg Ile Ala Val Lys Tyr Tyr Thr Pro Glu
             20                  25                  30

Trp Ser Thr Val Ala Ser Gln Ala Ser Phe Glu Lys Ala Leu Trp Asn
         35                  40                  45

Lys Thr Ser Arg Thr Asn Ala Arg Ala Glu Ala Glu Ile Ile Met Phe
     50                  55                  60

Asp Asn Val Val Val Val Tyr Lys Tyr Ile Gly Asp Leu Met Phe Tyr
65                  70                  75                  80

Val Thr Gly Ser Leu Asp Glu Asn Glu Leu Ile Leu Tyr Thr Val Leu
                 85                  90                  95

Gln Ala Phe Tyr Glu Ser Val Thr Ile Leu Leu Arg Gln Gln Val Glu
            100                 105                 110

Lys Lys Thr Val Leu Glu Asn Leu Asp Leu Val Leu Leu Ala Met Asp
        115                 120                 125

Glu Ile Val Asp Gly Gly Ile Ile Leu Glu Thr Glu Pro Ala Met Ile
    130                 135                 140

Ala Ser Arg Val Thr Met Arg Gly Ala Asp Gly Glu Gln Ala Pro Val
145                 150                 155                 160

Pro Ile Thr Glu Gln Thr Phe Ser Lys Ala Leu Ala Ser Ala Lys Glu
                165                 170                 175
```

```
His Leu Ala Arg Ser Leu Leu Lys
            180

<210> SEQ ID NO 49
<211> LENGTH: 928
<212> TYPE: DNA
<213> ORGANISM: Physcomitrella patens
<220> FEATURE:
<221> NAME/KEY: CDS
<222> LOCATION: (240)..(776)

<400> SEQUENCE: 49
acttttgcct cgttcgctcc aagcgtgatt cgacaacggg gtcttcgtgt ttttttcttg      60
cactatccgg aggactttgc tcgccgcagc agatttccgg tgtagttcct tttctggggt     120
gctctggtga tatctaatcg ggcttcgcaa gtcccccgga aagtgggtct gggttagatc     180
tggtggaagc cgcatttgaa agcgaggtgt tgaaggagct gcggatcgac gctattaaa      239 atg gat gtt tct aca cct ttg ata aag aat gtt ctg ctt cta gat tcg      287
Met Asp Val Ser Thr Pro Leu Ile Lys Asn Val Leu Leu Leu Asp Ser
1               5                   10                  15 gaa ggg aag cgc gta gct gtt aag tat tac tcg gat gac tgg cct aag      335
Glu Gly Lys Arg Val Ala Val Lys Tyr Tyr Ser Asp Asp Trp Pro Lys
            20                  25                  30 ctt gct gat aaa ttg gcg tat gag aaa tcc gtg ttc acg aaa acc caa      383
Leu Ala Asp Lys Leu Ala Tyr Glu Lys Ser Val Phe Thr Lys Thr Gln
        35                  40                  45 cgc tcg att gcc cgc tca gaa gct gag att gga atg ttt gat gga tat      431
Arg Ser Ile Ala Arg Ser Glu Ala Glu Ile Gly Met Phe Asp Gly Tyr
    50                  55                  60 att gtg gtc tac aag ttc atc tca gac ctc cat ttc tat gtc acg gga      479
Ile Val Val Tyr Lys Phe Ile Ser Asp Leu His Phe Tyr Val Thr Gly
65                  70                  75                  80 ggt gag gat gag aac gaa ctg att gtg gca aca gtc ctg caa ggg ttc      527
Gly Glu Asp Glu Asn Glu Leu Ile Val Ala Thr Val Leu Gln Gly Phe
                85                  90                  95 ttt gac gcc gtc ggt tta ctt ctc aga aac aac gtc gac aaa aag agt      575
Phe Asp Ala Val Gly Leu Leu Leu Arg Asn Asn Val Asp Lys Lys Ser
            100                 105                 110 gtg ctg gaa aac cta gat ctc gtc ctt ctc tgc ctt gat gag atc ata      623
Val Leu Glu Asn Leu Asp Leu Val Leu Leu Cys Leu Asp Glu Ile Ile
        115                 120                 125 gat ggc ggc atc att cta gag act gat gcc aac gtc ata gcc ggc aga      671
Asp Gly Gly Ile Ile Leu Glu Thr Asp Ala Asn Val Ile Ala Gly Arg
    130                 135                 140 gtt tca atg cgg ggt gct gat gcg gat gtt ccc ctt tca gaa cag aca      719
Val Ser Met Arg Gly Ala Asp Ala Asp Val Pro Leu Ser Glu Gln Thr
145                 150                 155                 160 ctc gct caa gca ttg gcc acc gcc aag gag cat ttt gca aga tca ctt      767
Leu Ala Gln Ala Leu Ala Thr Ala Lys Glu His Phe Ala Arg Ser Leu
                165                 170                 175 ctc aag tag ggattagtag ttatttggta gcaaaagtg gacagaactg                816
Leu Lys cgactctgca gagttgctcc tcttactttt ttcaaggctt agccttgaaa tcttccatct     876
tttctgtatc acttgcctac ataatcaaaa tgtttacata aacgattcaa at            928

<210> SEQ ID NO 50
<211> LENGTH: 178
<212> TYPE: PRT
<213> ORGANISM: Physcomitrella patens

<400> SEQUENCE: 50
```

```
Met Asp Val Ser Thr Pro Leu Ile Lys Asn Val Leu Leu Asp Ser
1               5                   10                  15

Glu Gly Lys Arg Val Ala Val Lys Tyr Tyr Ser Asp Asp Trp Pro Lys
                20                  25                  30

Leu Ala Asp Lys Leu Ala Tyr Glu Lys Ser Val Phe Thr Lys Thr Gln
            35                  40                  45

Arg Ser Ile Ala Arg Ser Glu Ala Glu Ile Gly Met Phe Asp Gly Tyr
        50                  55                  60

Ile Val Val Tyr Lys Phe Ile Ser Asp Leu His Phe Tyr Val Thr Gly
65                  70                  75                  80

Gly Glu Asp Glu Asn Glu Leu Ile Val Ala Thr Val Leu Gln Gly Phe
                85                  90                  95

Phe Asp Ala Val Gly Leu Leu Leu Arg Asn Asn Val Asp Lys Lys Ser
            100                 105                 110

Val Leu Glu Asn Leu Asp Leu Val Leu Leu Cys Leu Asp Glu Ile Ile
        115                 120                 125

Asp Gly Gly Ile Ile Leu Glu Thr Asp Ala Asn Val Ile Ala Gly Arg
130                 135                 140

Val Ser Met Arg Gly Ala Asp Ala Asp Val Pro Leu Ser Glu Gln Thr
145                 150                 155                 160

Leu Ala Gln Ala Leu Ala Thr Ala Lys Glu His Phe Ala Arg Ser Leu
                165                 170                 175

Leu Lys

<210> SEQ ID NO 51
<211> LENGTH: 846
<212> TYPE: DNA
<213> ORGANISM: Vitis vinifera
<220> FEATURE:
<221> NAME/KEY: CDS
<222> LOCATION: (33)..(584)

<400> SEQUENCE: 51
cgcgatcgaa gctgagagtc gcatttggat ca atg gcg aac ttc tct act cac      53
                                    Met Ala Asn Phe Ser Thr His
                                    1               5 gga gct tgc ccc tct ata aaa aac att ctt ctt ctg gat tct gaa ggg    101
Gly Ala Cys Pro Ser Ile Lys Asn Ile Leu Leu Leu Asp Ser Glu Gly
        10                  15                  20 aag cgt gtg gca gtc aaa tat tac tcc gat gat tgg cca aca aat gct   149
Lys Arg Val Ala Val Lys Tyr Tyr Ser Asp Asp Trp Pro Thr Asn Ala
    25                  30                  35 gca aaa tta gct ttt gaa aag tcc gtc ttc act aaa act caa aag aca   197
Ala Lys Leu Ala Phe Glu Lys Ser Val Phe Thr Lys Thr Gln Lys Thr
40                  45                  50                  55 aat gct cgg act gag gcg gag ata gca atg ttt gag aac aac gta gtt   245
Asn Ala Arg Thr Glu Ala Glu Ile Ala Met Phe Glu Asn Asn Val Val
                60                  65                  70 atc tac aag ttt atc cag gat ctg cac ttc ttt gtg act gga ggt gat   293
Ile Tyr Lys Phe Ile Gln Asp Leu His Phe Phe Val Thr Gly Gly Asp
            75                  80                  85 gat gaa aac gaa ctc atc tta gcc aca gtt ctt cag ggc ttc tcc gat   341
Asp Glu Asn Glu Leu Ile Leu Ala Thr Val Leu Gln Gly Phe Ser Asp
        90                  95                  100 gca gtt gcc ctt ctc ctc agg aac aac att gac aag agg gag gca ctt   389
Ala Val Ala Leu Leu Leu Arg Asn Asn Ile Asp Lys Arg Glu Ala Leu
    105                 110                 115
```

```
gag aac ttg gat ctc att ctc cta tgc ctt gat gag att gtt gat gga      437
Glu Asn Leu Asp Leu Ile Leu Leu Cys Leu Asp Glu Ile Val Asp Gly
120                 125                 130                 135 ggg atg atc ctt gaa act gat gcc agt gtt att gag gga aaa gta gca      485
Gly Met Ile Leu Glu Thr Asp Ala Ser Val Ile Glu Gly Lys Val Ala
                140                 145                 150 gct cat agc att gat gct gga gct cca tta tct gag cag act cta acc      533
Ala His Ser Ile Asp Ala Gly Ala Pro Leu Ser Glu Gln Thr Leu Thr
                155                 160                 165 caa gca ttg gca aca gca cgt gaa cat ttg aca aga tcc ctt ctc aaa      581
Gln Ala Leu Ala Thr Ala Arg Glu His Leu Thr Arg Ser Leu Leu Lys
        170                 175                 180 tga tacgcactgc aaatgagttg gcttcccttt cttttgtgat taaattttc            634 ctcagtggaa cacccgttca tttccctttg gttatatttt gcttgaccct actggaaaac    694
gaggttcatg ctgtcaggcc ccctttatgg ccttcctcct ctttaccaat taattgattg    754
atcattggat ttgaagagtt tgtgattcac tgaatatagc ttatgttatg attcggtgaa    814
taatattcaa tgctagatac agatcttcaa aa                                  846

<210> SEQ ID NO 52
<211> LENGTH: 183
<212> TYPE: PRT
<213> ORGANISM: Vitis vinifera

<400> SEQUENCE: 52

Met Ala Asn Phe Ser Thr His Gly Ala Cys Pro Ser Ile Lys Asn Ile
1               5                   10                  15

Leu Leu Leu Asp Ser Glu Gly Lys Arg Val Ala Val Lys Tyr Tyr Ser
                20                  25                  30

Asp Asp Trp Pro Thr Asn Ala Ala Lys Leu Ala Phe Glu Lys Ser Val
            35                  40                  45

Phe Thr Lys Thr Gln Lys Thr Asn Ala Arg Thr Glu Ala Glu Ile Ala
        50                  55                  60

Met Phe Glu Asn Asn Val Val Ile Tyr Lys Phe Ile Gln Asp Leu His
65                  70                  75                  80

Phe Phe Val Thr Gly Gly Asp Asp Glu Asn Glu Leu Ile Leu Ala Thr
                85                  90                  95

Val Leu Gln Gly Phe Ser Asp Ala Val Ala Leu Leu Arg Asn Asn
                100                 105                 110

Ile Asp Lys Arg Glu Ala Leu Glu Asn Leu Asp Leu Ile Leu Leu Cys
            115                 120                 125

Leu Asp Glu Ile Val Asp Gly Gly Met Ile Leu Glu Thr Asp Ala Ser
        130                 135                 140

Val Ile Glu Gly Lys Val Ala Ala His Ser Ile Asp Ala Gly Ala Pro
145                 150                 155                 160

Leu Ser Glu Gln Thr Leu Thr Gln Ala Leu Ala Thr Ala Arg Glu His
                165                 170                 175

Leu Thr Arg Ser Leu Leu Lys
            180

<210> SEQ ID NO 53
<211> LENGTH: 587
<212> TYPE: DNA
<213> ORGANISM: Arabidopsis lyrata
<220> FEATURE:
<221> NAME/KEY: CDS
<222> LOCATION: (21)..(566)
```

```
<400> SEQUENCE: 53
tttatcttgg ttcaacaaca atg gca ggg act aat gat tct tgt cct ttg gta        53
                     Met Ala Gly Thr Asn Asp Ser Cys Pro Leu Val
                     1               5                  10 aag aac att ctt ctt cta gac tct gaa gga aag cgt gtg gct gtc aag          101
Lys Asn Ile Leu Leu Leu Asp Ser Glu Gly Lys Arg Val Ala Val Lys
        15                  20                  25 tat tac tca gat gat tgg aca act aat gct gcc aag tta gct ttt gaa          149
Tyr Tyr Ser Asp Asp Trp Thr Thr Asn Ala Ala Lys Leu Ala Phe Glu
            30                  35                  40 aaa tat gtc ttc tcg aag acc tct aaa acc aat gct cgc aca gaa gcg          197
Lys Tyr Val Phe Ser Lys Thr Ser Lys Thr Asn Ala Arg Thr Glu Ala
45                  50                  55 gag atc aca ctg ttg gag aat aat att gtt gtc tat aag ttt gcc cag          245
Glu Ile Thr Leu Leu Glu Asn Asn Ile Val Val Tyr Lys Phe Ala Gln
60                  65                  70                  75 gat ctg cat ttc ttt gtt acc gga ggt gaa aat gaa aac gag ctc gtc          293
Asp Leu His Phe Phe Val Thr Gly Gly Glu Asn Glu Asn Glu Leu Val
                80                  85                  90 tta tca tct gtt ctt caa ggc ttt ttt gat gct gtt gca tta ctt ctg          341
Leu Ser Ser Val Leu Gln Gly Phe Phe Asp Ala Val Ala Leu Leu Leu
            95                  100                 105 agg aac aat gtt gaa aag atg gaa gcc ctt gaa aac ttg gat ctc atc          389
Arg Asn Asn Val Glu Lys Met Glu Ala Leu Glu Asn Leu Asp Leu Ile
        110                 115                 120 ttt ttg tgc ctt gat gag atg gtt gat caa ggg atg gta ctc gaa aca          437
Phe Leu Cys Leu Asp Glu Met Val Asp Gln Gly Met Val Leu Glu Thr
    125                 130                 135 gac gcc aat gtt att gcg gga aaa gta gca atg caa agc gca gaa gca          485
Asp Ala Asn Val Ile Ala Gly Lys Val Ala Met Gln Ser Ala Glu Ala
140                 145                 150                 155 agt ggt tca ctc tct gaa cag acg tta act caa gca ttg gca aca gct          533
Ser Gly Ser Leu Ser Glu Gln Thr Leu Thr Gln Ala Leu Ala Thr Ala
                160                 165                 170 cgg gag cac ctt gca aga agt ctt ctt aca taa ttttcatcgt gggagagaaa       586
Arg Glu His Leu Ala Arg Ser Leu Leu Thr
            175                 180 t                                                                        587

<210> SEQ ID NO 54
<211> LENGTH: 181
<212> TYPE: PRT
<213> ORGANISM: Arabidopsis lyrata

<400> SEQUENCE: 54

Met Ala Gly Thr Asn Asp Ser Cys Pro Leu Val Lys Asn Ile Leu Leu
1               5                   10                  15

Leu Asp Ser Glu Gly Lys Arg Val Ala Val Lys Tyr Tyr Ser Asp Asp
            20                  25                  30

Trp Thr Thr Asn Ala Ala Lys Leu Ala Phe Glu Lys Tyr Val Phe Ser
        35                  40                  45

Lys Thr Ser Lys Thr Asn Ala Arg Thr Glu Ala Glu Ile Thr Leu Leu
    50                  55                  60

Glu Asn Asn Ile Val Val Tyr Lys Phe Ala Gln Asp Leu His Phe Phe
65                  70                  75                  80

Val Thr Gly Gly Glu Asn Glu Asn Glu Leu Val Leu Ser Ser Val Leu
                85                  90                  95

Gln Gly Phe Phe Asp Ala Val Ala Leu Leu Leu Arg Asn Asn Val Glu
            100                 105                 110
```

```
Lys Met Glu Ala Leu Glu Asn Leu Asp Leu Ile Phe Leu Cys Leu Asp
        115                 120                 125

Glu Met Val Asp Gln Gly Met Val Leu Glu Thr Asp Ala Asn Val Ile
130                 135                 140

Ala Gly Lys Val Ala Met Gln Ser Ala Glu Ala Ser Gly Ser Leu Ser
145                 150                 155                 160

Glu Gln Thr Leu Thr Gln Ala Leu Ala Thr Ala Arg Glu His Leu Ala
                165                 170                 175

Arg Ser Leu Leu Thr
            180

<210> SEQ ID NO 55
<211> LENGTH: 1954
<212> TYPE: DNA
<213> ORGANISM: Volvox carteri
<220> FEATURE:
<221> NAME/KEY: CDS
<222> LOCATION: (127)..(681)

<400> SEQUENCE: 55
attcgggaat agagttggaa atataacaaa tagattgtgt gctatccgag cgttcataat      60
cggctacttt ttcttgggct gggtacatag ttacgtgtga actcactttg ggtaacttttt    120 gtaaga atg gct act atg gac ccc acg ctc cca att gtg aag aac ctg        168
       Met Ala Thr Met Asp Pro Thr Leu Pro Ile Val Lys Asn Leu
       1               5                   10 ctg ttg ttg gac tcg gag ggc aag cgc atc gcc gtc aag tat tac aca        216
Leu Leu Leu Asp Ser Glu Gly Lys Arg Ile Ala Val Lys Tyr Tyr Thr
15                  20                  25                  30 cct gag tgg tcg act gtg gca agc cag gga acc ttt gag aag gcg ctt        264
Pro Glu Trp Ser Thr Val Ala Ser Gln Gly Thr Phe Glu Lys Ala Leu
                35                  40                  45 tgg aac aag acg agt cga acg aac gca cga gca gag gcg gaa att atc        312
Trp Asn Lys Thr Ser Arg Thr Asn Ala Arg Ala Glu Ala Glu Ile Ile
            50                  55                  60 atg ttt gat aat gtg gtg gtc gtg tac aag tac atc ggc gac ttg atg        360
Met Phe Asp Asn Val Val Val Val Tyr Lys Tyr Ile Gly Asp Leu Met
        65                  70                  75 ttc tat gtg acg ggc agc cag gac gag aac gag ctc gtc cta tac acg        408
Phe Tyr Val Thr Gly Ser Gln Asp Glu Asn Glu Leu Val Leu Tyr Thr
    80                  85                  90 gtc ctc caa gct ttc tac gag tcg gtg aca atc ctc ttg aga caa caa        456
Val Leu Gln Ala Phe Tyr Glu Ser Val Thr Ile Leu Leu Arg Gln Gln
95                  100                 105                 110 gtg gag aag aag acc gtc ctc gaa aac ctg gat cta gtc ctc ctg gca        504
Val Glu Lys Lys Thr Val Leu Glu Asn Leu Asp Leu Val Leu Leu Ala
                115                 120                 125 atc gat gaa att gtt gac ggc ggt atc att ctg gag acg gag cca gcg        552
Ile Asp Glu Ile Val Asp Gly Gly Ile Ile Leu Glu Thr Glu Pro Ala
            130                 135                 140 gtc att gcc tcg cgg gta acg atg cgg gga gcg gac gga gag cag gct        600
Val Ile Ala Ser Arg Val Thr Met Arg Gly Ala Asp Gly Glu Gln Ala
        145                 150                 155 gcg atg ccg atc acg gag cag acg ttc tcc aag gcg ctg gcc tcc gca        648
Ala Met Pro Ile Thr Glu Gln Thr Phe Ser Lys Ala Leu Ala Ser Ala
    160                 165                 170 aag gag cac ttg gcg cgt tcg ctt ctc aaa taa ggagaggggg accccaccgg     701
Lys Glu His Leu Ala Arg Ser Leu Leu Lys
175                 180
```

```
gaacggcccg cgctgcacca tggaaatcca cgtggattac gggattttca atatcagccg    761
cggcacacag tcccgcgttg tgcggcgcgg gcaggtgcgt ctgctcggga cacggctttc    821
agcttgggag cattgcttgc gtttgggcgc agcgcgcagc agcacagttt tgcacgggcg    881
gggcatgccg tggggcatgt tccggacatc tagaggcga tagctgcgca tgggactatg     941
gacatatttg gtttgggcac gcaggtatcc gcttgcggct tgaactcgtt tagtgagcag   1001
tggacggagg tggagctggg gtggagagct tcaaataatt tgggggatct gcatggtctt   1061
ggacaacaac agggttttag ggagggcca accgggagag gggggacgaa gccccaccc     1121 tcgtactcgc cccgcggatg tgtgggcgag tactcgaggc tcgtgcgtgc ggagctctgc   1181
ggcaaaagtt ctctcatgtt taagcacctc ctttattgac ttgcgaggta cgtgtacaag   1241
ggtgtgtgag caggaggcgc cgtgctctga ggagcacacc cgtgacgacg aaaagacgga   1301
aactgggtgg ggatcttgct tgcttttagcg ctcgattggg cttcatggag aagactttgg  1361
ggcgaagatg cccggctggt ctgttctggg gtaacctagc agcatgctgt ccagtacgct   1421
atgggacttt tggtcgggtt tcgggtgcgg aatatcaggg tttaagggta aaggacacac   1481
gctcgacaaa aggtatggga gattatgctt tggctcgaca agagctatgg gggataatgc   1541
tttggctatc tgtgactcac tgccgtttgt gaaagctccg gtctagggtt atcgtaggct   1601
cgttgggttg gctacagatg agtgcacgag cgatgatacg gattctcgag cgagtcaagg   1661
cggaagtgga ccgacatatg gattccgtgt acgtactacg tttatgatta tgtttagcgc   1721
ttcggagccg ttgtgggtcg gagccggcgc tccagccagc tgccgggcgc tgacattgca   1781
tgaagcattg cttttttaagg aggttccaat gttgcaatga acctaatca acaatcgccg    1841 tcgttcttcc tactggaaag ccaagtatgc tatctgggtg aaggtcgtgt ataggttcga   1901
gggggctggt gtccgttgaa cggccgctct ctccacattg tacggatgga tgg          1954
```

<210> SEQ ID NO 56
<211> LENGTH: 184
<212> TYPE: PRT
<213> ORGANISM: Volvox carteri

<400> SEQUENCE: 56

Met Ala Thr Met Asp Pro Thr Leu Pro Ile Val Lys Asn Leu Leu Leu
1               5                   10                  15

Leu Asp Ser Glu Gly Lys Arg Ile Ala Val Lys Tyr Tyr Thr Pro Glu
            20                  25                  30

Trp Ser Thr Val Ala Ser Gln Gly Thr Phe Glu Lys Ala Leu Trp Asn
        35                  40                  45

Lys Thr Ser Arg Thr Asn Ala Arg Ala Glu Ala Glu Ile Ile Met Phe
    50                  55                  60

Asp Asn Val Val Val Tyr Lys Tyr Ile Gly Asp Leu Met Phe Tyr
65                  70                  75                  80

Val Thr Gly Ser Gln Asp Glu Asn Glu Leu Val Leu Tyr Thr Val Leu
                85                  90                  95

Gln Ala Phe Tyr Glu Ser Val Thr Ile Leu Leu Arg Gln Gln Val Glu
            100                 105                 110

Lys Lys Thr Val Leu Glu Asn Leu Asp Leu Val Leu Leu Ala Ile Asp
        115                 120                 125

Glu Ile Val Asp Gly Gly Ile Ile Leu Glu Thr Glu Pro Ala Val Ile
    130                 135                 140

Ala Ser Arg Val Thr Met Arg Gly Ala Asp Gly Glu Gln Ala Ala Met
145                 150                 155                 160

```
Pro Ile Thr Glu Gln Thr Phe Ser Lys Ala Leu Ala Ser Ala Lys Glu
            165                 170                 175

His Leu Ala Arg Ser Leu Leu Lys
            180

<210> SEQ ID NO 57
<211> LENGTH: 639
<212> TYPE: DNA
<213> ORGANISM: Selaginella moellendorffii
<220> FEATURE:
<221> NAME/KEY: CDS
<222> LOCATION: (1)..(540)

<400> SEQUENCE: 57 atg gga gag ctg ctg gat ccg ttc gtg agc aac ata ctg ctg ctg gac        48
Met Gly Glu Leu Leu Asp Pro Phe Val Ser Asn Ile Leu Leu Leu Asp
1               5                   10                  15 gac gag ggc aag cgc gtg gcc gtc aag tac tac agc gac tat tgg ccc        96
Asp Glu Gly Lys Arg Val Ala Val Lys Tyr Tyr Ser Asp Tyr Trp Pro
                20                  25                  30 aac aac gcg gcc aag ctc gcc ttc gag aag tcg gtc ttc acc aag acg       144
Asn Asn Ala Ala Lys Leu Ala Phe Glu Lys Ser Val Phe Thr Lys Thr
            35                  40                  45 cag cgc atg aac gcc cgc cag gaa gcg gag att ggt ttg tac gag ggc       192
Gln Arg Met Asn Ala Arg Gln Glu Ala Glu Ile Gly Leu Tyr Glu Gly
        50                  55                  60 cat gtc gtg gtg ttt aag ttc gtg gcc gac ctc tac ttc tac gtg act       240
His Val Val Val Phe Lys Phe Val Ala Asp Leu Tyr Phe Tyr Val Thr
65                  70                  75                  80 ggc agg gag gac gag aac gag ctc atc ctc gcg act gtt ctt caa gcg       288
Gly Arg Glu Asp Glu Asn Glu Leu Ile Leu Ala Thr Val Leu Gln Ala
                85                  90                  95 ttt ttc gac gct gtg tcg att cta ctc aga ggc aat gtg gac aag aag       336
Phe Phe Asp Ala Val Ser Ile Leu Leu Arg Gly Asn Val Asp Lys Lys
            100                 105                 110 acg gtc ctg gag aac ctg gat ttg atc ctt ttg tgc ttg gac gag att       384
Thr Val Leu Glu Asn Leu Asp Leu Ile Leu Leu Cys Leu Asp Glu Ile
        115                 120                 125 gtc gac gga ggc acc gtt ttg gag act gat gcc aac agc ata gct tca       432
Val Asp Gly Gly Thr Val Leu Glu Thr Asp Ala Asn Ser Ile Ala Ser
    130                 135                 140 aag gta gcc atg cgc ggc gcg gag tcc gac gtc cca ttc tca gaa cag       480
Lys Val Ala Met Arg Gly Ala Glu Ser Asp Val Pro Phe Ser Glu Gln
145                 150                 155                 160 acg ttt tct caa gca ctt gct aca gcc aag gaa cat cta acg agg tct       528
Thr Phe Ser Gln Ala Leu Ala Thr Ala Lys Glu His Leu Thr Arg Ser
                165                 170                 175 ctt ctc aag tga attgtttctt ccgattgttt ccattatggg atccaagcat           580
Leu Leu Lys tagttcgggt aacttaagct tgcaagaatc aatcgttcta taaatagcc attctttt        639

<210> SEQ ID NO 58
<211> LENGTH: 179
<212> TYPE: PRT
<213> ORGANISM: Selaginella moellendorffii

<400> SEQUENCE: 58

Met Gly Glu Leu Leu Asp Pro Phe Val Ser Asn Ile Leu Leu Leu Asp
1               5                   10                  15

Asp Glu Gly Lys Arg Val Ala Val Lys Tyr Tyr Ser Asp Tyr Trp Pro
```

```
                    20                  25                  30
Asn Asn Ala Ala Lys Leu Ala Phe Glu Lys Ser Val Phe Thr Lys Thr
            35                  40                  45

Gln Arg Met Asn Ala Arg Gln Glu Ala Glu Ile Gly Leu Tyr Glu Gly
        50                  55                  60

His Val Val Val Phe Lys Phe Val Ala Asp Leu Tyr Phe Tyr Val Thr
65                  70                  75                  80

Gly Arg Glu Asp Glu Asn Glu Leu Ile Leu Ala Thr Val Leu Gln Ala
                85                  90                  95

Phe Phe Asp Ala Val Ser Ile Leu Leu Arg Gly Asn Val Asp Lys Lys
            100                 105                 110

Thr Val Leu Glu Asn Leu Asp Leu Ile Leu Leu Cys Leu Asp Glu Ile
        115                 120                 125

Val Asp Gly Gly Thr Val Leu Glu Thr Asp Ala Asn Ser Ile Ala Ser
    130                 135                 140

Lys Val Ala Met Arg Gly Ala Glu Ser Asp Val Pro Phe Ser Glu Gln
145                 150                 155                 160

Thr Phe Ser Gln Ala Leu Ala Thr Ala Lys Glu His Leu Thr Arg Ser
                165                 170                 175

Leu Leu Lys

<210> SEQ ID NO 59
<211> LENGTH: 822
<212> TYPE: DNA
<213> ORGANISM: Glycine max
<220> FEATURE:
<221> NAME/KEY: CDS
<222> LOCATION: (49)..(594)

<400> SEQUENCE: 59
tactatatat agagtcccgc actctgtaac tgattctatt tctcggaa atg gcg tct         57
                                                    Met Ala Ser
                                                    1 tat ggc tca tgt ccg tcg ata aag aat att ctt ctt cta gac tca gag        105
Tyr Gly Ser Cys Pro Ser Ile Lys Asn Ile Leu Leu Leu Asp Ser Glu
    5                   10                  15 gga aag cgt gtg gca gtc aag tat ttt tca gac gac tgg cca acc aac        153
Gly Lys Arg Val Ala Val Lys Tyr Phe Ser Asp Asp Trp Pro Thr Asn
20                  25                  30                  35 aac tca aag atc gct ttt gag aag ttt gtg ttt agt aag act gtt aag        201
Asn Ser Lys Ile Ala Phe Glu Lys Phe Val Phe Ser Lys Thr Val Lys
            40                  45                  50 aca aat gct cga aca gaa gct gag atc aca tta ctc gac aac aat atc        249
Thr Asn Ala Arg Thr Glu Ala Glu Ile Thr Leu Leu Asp Asn Asn Ile
        55                  60                  65 att att tac aaa ttt gta caa gat ctc cat ttc ttt gtc act ggt ggc        297
Ile Ile Tyr Lys Phe Val Gln Asp Leu His Phe Phe Val Thr Gly Gly
    70                  75                  80 gat gat gca aat gag atc att tta gct tca gtt ctt cag ggt tcc ttt        345
Asp Asp Ala Asn Glu Ile Ile Leu Ala Ser Val Leu Gln Gly Phe Phe
85                  90                  95 gat gca atc acg ctt ctc ttg agg aac aat gtt gac aaa aga gag gcg        393
Asp Ala Ile Thr Leu Leu Leu Arg Asn Asn Val Asp Lys Arg Glu Ala
100                 105                 110                 115 ctg gaa aac ttg gac ctc att ctt tta tgc ctt gat gag att gtt gat        441
Leu Glu Asn Leu Asp Leu Ile Leu Leu Cys Leu Asp Glu Ile Val Asp
            120                 125                 130 gga ggg atg ata ctt gaa aca aat gga cca ctt att gct gaa aaa gtt        489
```

```
                                Gly Gly Met Ile Leu Glu Thr Asn Gly Pro Leu Ile Ala Glu Lys Val
                                            135                 140                 145 acc tcc cat agc atg gat ggt gct gaa tcc ccc ctg tct gag cag aca         537
Thr Ser His Ser Met Asp Gly Ala Glu Ser Pro Leu Ser Glu Gln Thr
            150                 155                 160 cta act caa gcc tgg gct aca gct aga gaa cat ttg aca aga acc ctt         585
Leu Thr Gln Ala Trp Ala Thr Ala Arg Glu His Leu Thr Arg Thr Leu
    165                 170                 175 cta aaa taa agttcgcctg caaaggagct tcgttatatt ctagagtctt                 634
Leu Lys
180 ttttttattt attatctaca cagttgtttt aatgttttat cttctcattt gttgtgagat       694 actgcgatat gagtttcata tcatattcaa cgctgatttt tttattcatt attattcctg       754 ttattttttt ttgaatactg aaaggattt atttatccta ataaccagt taacccccca         814 aaaaaatg                                                                822

<210> SEQ ID NO 60
<211> LENGTH: 181
<212> TYPE: PRT
<213> ORGANISM: Glycine max

<400> SEQUENCE: 60

Met Ala Ser Tyr Gly Ser Cys Pro Ser Ile Lys Asn Ile Leu Leu Leu
1               5                   10                  15

Asp Ser Glu Gly Lys Arg Val Ala Val Lys Tyr Phe Ser Asp Asp Trp
            20                  25                  30

Pro Thr Asn Asn Ser Lys Ile Ala Phe Glu Lys Phe Val Phe Ser Lys
        35                  40                  45

Thr Val Lys Thr Asn Ala Arg Thr Glu Ala Glu Ile Thr Leu Leu Asp
    50                  55                  60

Asn Asn Ile Ile Ile Tyr Lys Phe Val Gln Asp Leu His Phe Phe Val
65                  70                  75                  80

Thr Gly Gly Asp Asp Ala Asn Glu Ile Ile Leu Ala Ser Val Leu Gln
                85                  90                  95

Gly Phe Phe Asp Ala Ile Thr Leu Leu Leu Arg Asn Asn Val Asp Lys
            100                 105                 110

Arg Glu Ala Leu Glu Asn Leu Asp Leu Ile Leu Leu Cys Leu Asp Glu
        115                 120                 125

Ile Val Asp Gly Gly Met Ile Leu Glu Thr Asn Gly Pro Leu Ile Ala
    130                 135                 140

Glu Lys Val Thr Ser His Ser Met Asp Gly Ala Glu Ser Pro Leu Ser
145                 150                 155                 160

Glu Gln Thr Leu Thr Gln Ala Trp Ala Thr Ala Arg Glu His Leu Thr
                165                 170                 175

Arg Thr Leu Leu Lys
            180

<210> SEQ ID NO 61
<211> LENGTH: 1007
<212> TYPE: DNA
<213> ORGANISM: Brachypodium distachyon
<220> FEATURE:
<221> NAME/KEY: CDS
<222> LOCATION: (145)..(678)

<400> SEQUENCE: 61
aataagaact tctcctcgtt gtcatttctg ttcgtcttgg tcgccttccc tgcccttgcg       60
```

```
cttgcacagc acagcaatcg gcgacgcaat ccctcaggcc atcactcgct tctttcccca      120
cgctcgcaaa tctacctttc cgag atg ggg tcc tgc cct tcg gtt aag aac         171
                           Met Gly Ser Cys Pro Ser Val Lys Asn
                             1               5 att ctt gtg ctg gat tcc gaa ggg aag cgc gtg gcc gtg aag tac tac        219
Ile Leu Val Leu Asp Ser Glu Gly Lys Arg Val Ala Val Lys Tyr Tyr
 10              15                  20                  25 agc gat gaa tgg ccc tcc gtg tct tcc aag tta gct ttc gag aag tca        267
Ser Asp Glu Trp Pro Ser Val Ser Ser Lys Leu Ala Phe Glu Lys Ser
                 30                  35                  40 gtc ttt gtg aag acc cag aaa acg agt gct aga aca gaa gct gag gta        315
Val Phe Val Lys Thr Gln Lys Thr Ser Ala Arg Thr Glu Ala Glu Val
             45                  50                  55 gta atg ttt gat ggt tac atc att gtc tac aag ttc atc caa gat cta        363
Val Met Phe Asp Gly Tyr Ile Ile Val Tyr Lys Phe Ile Gln Asp Leu
         60                  65                  70 cac ttc ttt gta acc gga gga gat gag gag aat gag ctc att tta gcg        411
His Phe Phe Val Thr Gly Gly Asp Glu Glu Asn Glu Leu Ile Leu Ala
 75                  80                  85 tca gtt ctt cag ggg ttt tct gat gct gtt ggc cta ctt ctc aga aac        459
Ser Val Leu Gln Gly Phe Ser Asp Ala Val Gly Leu Leu Leu Arg Asn
 90                  95                 100                 105 aat gta gac aaa agg act gca ctc gaa aat ctt gat ctc atc ttt tta        507
Asn Val Asp Lys Arg Thr Ala Leu Glu Asn Leu Asp Leu Ile Phe Leu
                110                 115                 120 tgc ctt gat gaa gtt gtt gat gga ggg att gtt ctt gaa aca gat gca        555
Cys Leu Asp Glu Val Val Asp Gly Gly Ile Val Leu Glu Thr Asp Ala
            125                 130                 135 aat ctg ata gct gag aag gta tca ggt cat gga ttg gaa gga gct gga        603
Asn Leu Ile Ala Glu Lys Val Ser Gly His Gly Leu Glu Gly Ala Gly
        140                 145                 150 tca ttc act gag cag aca ata agc caa gcc ctg gcg aca gca aga gag        651
Ser Phe Thr Glu Gln Thr Ile Ser Gln Ala Leu Ala Thr Ala Arg Glu
    155                 160                 165 cac ttt gca agg tca ctt ctc aag taa gaggttggca tccttcaggt              698
His Phe Ala Arg Ser Leu Leu Lys
170                 175 tgacgatgag ctgttgtcga aatggggtcc cgtagctcag tccgcccgat tgtgagaaa       758 gaaagaaagt gaactgaatc tttgtgtgtg agttgatccg ttattgtggc cgtcgacatt      818
ttgttgctgg gatgtatctg cagaccgact ggttaactag tctattaaga ttttcagaa       878 gcttgtgtgc agcagatcat gttgtttcta ctctgtttgt tgtattaccg tcgagcagca      938
gcgcgacttg tgtgacctac aactctcaag atggttggaa aagctggatt atcataatcc      998
acctcaaag                                                             1007

<210> SEQ ID NO 62
<211> LENGTH: 177
<212> TYPE: PRT
<213> ORGANISM: Brachypodium distachyon

<400> SEQUENCE: 62

Met Gly Ser Cys Pro Ser Val Lys Asn Ile Leu Val Leu Asp Ser Glu
  1               5                  10                  15

Gly Lys Arg Val Ala Val Lys Tyr Tyr Ser Asp Glu Trp Pro Ser Val
             20                  25                  30

Ser Ser Lys Leu Ala Phe Glu Lys Ser Val Phe Val Lys Thr Gln Lys
         35                  40                  45
```

```
Thr Ser Ala Arg Thr Glu Ala Glu Val Val Met Phe Asp Gly Tyr Ile
    50                  55                  60

Ile Val Tyr Lys Phe Ile Gln Asp Leu His Phe Val Thr Gly Gly
65              70                  75                  80

Asp Glu Glu Asn Glu Leu Ile Leu Ala Ser Val Leu Gln Gly Phe Ser
                85                  90                  95

Asp Ala Val Gly Leu Leu Leu Arg Asn Asn Val Asp Lys Arg Thr Ala
                100                 105                 110

Leu Glu Asn Leu Asp Leu Ile Phe Leu Cys Leu Asp Glu Val Val Asp
            115                 120                 125

Gly Gly Ile Val Leu Glu Thr Asp Ala Asn Leu Ile Ala Glu Lys Val
        130                 135                 140

Ser Gly His Gly Leu Glu Gly Ala Gly Ser Phe Thr Glu Gln Thr Ile
145                 150                 155                 160

Ser Gln Ala Leu Ala Thr Ala Arg Glu His Phe Ala Arg Ser Leu Leu
                165                 170                 175

Lys

<210> SEQ ID NO 63
<211> LENGTH: 471
<212> TYPE: DNA
<213> ORGANISM: Saccharomyces cerevisiae
<220> FEATURE:
<221> NAME/KEY: CDS
<222> LOCATION: (1)..(471)

<400> SEQUENCE: 63 atg acg caa tta aaa tat ttg ttg ctg gtt tct agg caa gga aaa atc      48
Met Thr Gln Leu Lys Tyr Leu Leu Leu Val Ser Arg Gln Gly Lys Ile
1               5                   10                  15 aga tta aag aaa tgg tac acg gca atg tcc gct ggt gaa aag gca aaa      96
Arg Leu Lys Lys Trp Tyr Thr Ala Met Ser Ala Gly Glu Lys Ala Lys
                20                  25                  30 att gtg aaa gac ttg aca cct acg ata tta gca aga aaa ccc aaa atg     144
Ile Val Lys Asp Leu Thr Pro Thr Ile Leu Ala Arg Lys Pro Lys Met
            35                  40                  45 tgt aac atc atc gag tat aat gac cac aaa gta gta tac aag cga tat     192
Cys Asn Ile Ile Glu Tyr Asn Asp His Lys Val Val Tyr Lys Arg Tyr
50                  55                  60 gct agt cta tat ttt att gtt ggg atg acg ccc gat gtt gac aat gaa     240
Ala Ser Leu Tyr Phe Ile Val Gly Met Thr Pro Asp Val Asp Asn Glu
65                  70                  75                  80 ctg ctg acc ttg gaa att atc cat cgg ttt gtc gaa aca atg gac aca     288
Leu Leu Thr Leu Glu Ile Ile His Arg Phe Val Glu Thr Met Asp Thr
                85                  90                  95 tat ttc ggc aat gtt tgt gag cta gac att ata ttt aac ttc agt aag     336
Tyr Phe Gly Asn Val Cys Glu Leu Asp Ile Ile Phe Asn Phe Ser Lys
            100                 105                 110 gtc tac gat atc ttg aat gag atg att atg tgc gat ggc tcc atc gca     384
Val Tyr Asp Ile Leu Asn Glu Met Ile Met Cys Asp Gly Ser Ile Ala
        115                 120                 125 gag agc agt agg aag gaa gta ctg cac cat gtg acc gtg atg gac acc     432
Glu Ser Ser Arg Lys Glu Val Leu His His Val Thr Val Met Asp Thr
130                 135                 140 atg gag agc aac gat aat ctt gaa agg gta ttg agt tag                 471
Met Glu Ser Asn Asp Asn Leu Glu Arg Val Leu Ser
145                 150                 155
```

<210> SEQ ID NO 64
<211> LENGTH: 156
<212> TYPE: PRT
<213> ORGANISM: Saccharomyces cerevisiae

<400> SEQUENCE: 64

```
Met Thr Gln Leu Lys Tyr Leu Leu Val Ser Arg Gln Gly Lys Ile
1               5                   10                  15

Arg Leu Lys Lys Trp Tyr Thr Ala Met Ser Ala Gly Glu Lys Ala Lys
            20                  25                  30

Ile Val Lys Asp Leu Thr Pro Thr Ile Leu Ala Arg Lys Pro Lys Met
        35                  40                  45

Cys Asn Ile Ile Glu Tyr Asn Asp His Lys Val Val Tyr Lys Arg Tyr
50                  55                  60

Ala Ser Leu Tyr Phe Ile Val Gly Met Thr Pro Asp Val Asp Asn Glu
65                  70                  75                  80

Leu Leu Thr Leu Glu Ile Ile His Arg Phe Val Glu Thr Met Asp Thr
                85                  90                  95

Tyr Phe Gly Asn Val Cys Glu Leu Asp Ile Ile Phe Asn Phe Ser Lys
            100                 105                 110

Val Tyr Asp Ile Leu Asn Glu Met Ile Met Cys Asp Gly Ser Ile Ala
        115                 120                 125

Glu Ser Ser Arg Lys Glu Val Leu His His Val Thr Val Met Asp Thr
    130                 135                 140

Met Glu Ser Asn Asp Asn Leu Glu Arg Val Leu Ser
145                 150                 155
```

<210> SEQ ID NO 65
<211> LENGTH: 444
<212> TYPE: DNA
<213> ORGANISM: Saccharomyces cerevisiae
<220> FEATURE:
<221> NAME/KEY: CDS
<222> LOCATION: (1)..(444)

<400> SEQUENCE: 65

```
atg gca gta cag ttt ata ttg tgc ttt aat aag cag ggt gtg gtg cgg    48
Met Ala Val Gln Phe Ile Leu Cys Phe Asn Lys Gln Gly Val Val Arg
1               5                   10                  15 ttg gta aga tgg ttc gat gta cac agt tcg gat cct cag cgt agc cag    96
Leu Val Arg Trp Phe Asp Val His Ser Ser Asp Pro Gln Arg Ser Gln
            20                  25                  30 gat gcc att gcg cag att tat aga ctc ata tct tcc aga gat cat aag   144
Asp Ala Ile Ala Gln Ile Tyr Arg Leu Ile Ser Ser Arg Asp His Lys
        35                  40                  45 cat cag agt aac ttc gta gag ttt tcc gat tcg acg aaa ctc ata tac   192
His Gln Ser Asn Phe Val Glu Phe Ser Asp Ser Thr Lys Leu Ile Tyr
50                  55                  60 agg agg tat gcg ggt ctg tat ttt gtc atg ggt gtg gac tta ctt gac   240
Arg Arg Tyr Ala Gly Leu Tyr Phe Val Met Gly Val Asp Leu Leu Asp
65                  70                  75                  80 gat gaa ccc ata tat ttg tgc cac atc cat ctg ttt gtg gag gtg cta   288
Asp Glu Pro Ile Tyr Leu Cys His Ile His Leu Phe Val Glu Val Leu
                85                  90                  95 gat gca ttt ttc ggc aat gtc tgt gaa ctg gat atc gta ttc aac ttt   336
Asp Ala Phe Phe Gly Asn Val Cys Glu Leu Asp Ile Val Phe Asn Phe
            100                 105                 110 tac aaa gtc tat atg ata atg gac gag atg ttt att gga ggg gaa ata   384
Tyr Lys Val Tyr Met Ile Met Asp Glu Met Phe Ile Gly Gly Glu Ile
        115                 120                 125
```

```
caa gaa att tca aag gat atg ctg tta gaa aga cta agt att tta gat    432
Gln Glu Ile Ser Lys Asp Met Leu Leu Glu Arg Leu Ser Ile Leu Asp
        130                 135                 140 aga cta gac tag                                                    444
Arg Leu Asp
145

<210> SEQ ID NO 66
<211> LENGTH: 147
<212> TYPE: PRT
<213> ORGANISM: Saccharomyces cerevisiae

<400> SEQUENCE: 66

Met Ala Val Gln Phe Ile Leu Cys Phe Asn Lys Gln Gly Val Val Arg
1               5                   10                  15

Leu Val Arg Trp Phe Asp Val His Ser Ser Asp Pro Gln Arg Ser Gln
            20                  25                  30

Asp Ala Ile Ala Gln Ile Tyr Arg Leu Ile Ser Ser Arg Asp His Lys
        35                  40                  45

His Gln Ser Asn Phe Val Glu Phe Ser Asp Ser Thr Lys Leu Ile Tyr
    50                  55                  60

Arg Arg Tyr Ala Gly Leu Tyr Phe Val Met Gly Val Asp Leu Leu Asp
65                  70                  75                  80

Asp Glu Pro Ile Tyr Leu Cys His Ile His Leu Phe Val Glu Val Leu
                85                  90                  95

Asp Ala Phe Phe Gly Asn Val Cys Glu Leu Asp Ile Val Phe Asn Phe
            100                 105                 110

Tyr Lys Val Tyr Met Ile Met Asp Glu Met Phe Ile Gly Gly Glu Ile
        115                 120                 125

Gln Glu Ile Ser Lys Asp Met Leu Leu Glu Arg Leu Ser Ile Leu Asp
    130                 135                 140

Arg Leu Asp
145

<210> SEQ ID NO 67
<211> LENGTH: 585
<212> TYPE: DNA
<213> ORGANISM: Saccharomyces cerevisiae
<220> FEATURE:
<221> NAME/KEY: CDS
<222> LOCATION: (1)..(585)

<400> SEQUENCE: 67 atg att cat gca gtt cta ata ttc aat aag aaa tgc caa cca aga tta    48
Met Ile His Ala Val Leu Ile Phe Asn Lys Lys Cys Gln Pro Arg Leu
1               5                   10                  15 gtg aaa ttc tac acg ccg gtc gac ctt cca aag caa aaa ctg cta tta    96
Val Lys Phe Tyr Thr Pro Val Asp Leu Pro Lys Gln Lys Leu Leu Leu
            20                  25                  30 gag caa gta tat gaa ttg att tct caa agg aat agc gat ttt caa agt   144
Glu Gln Val Tyr Glu Leu Ile Ser Gln Arg Asn Ser Asp Phe Gln Ser
        35                  40                  45 tct ttt tta gtc acg cca cca tcg ctt ctg tta agc aat gaa aat aat   192
Ser Phe Leu Val Thr Pro Pro Ser Leu Leu Leu Ser Asn Glu Asn Asn
    50                  55                  60 aat gat gag gta aac aat gaa gat att caa atc atc tat aaa aac tac   240
Asn Asp Glu Val Asn Asn Glu Asp Ile Gln Ile Ile Tyr Lys Asn Tyr
65                  70                  75                  80 gct aca cta tat ttc act ttc atc gtg gat gat caa gaa tca gaa ctg   288
```

```
Ala Thr Leu Tyr Phe Thr Phe Ile Val Asp Asp Gln Glu Ser Glu Leu
                    85                  90                  95 gcc ata tta gat ctg atc caa act ttt gtg gaa tca ttg gac cgt tgt        336
Ala Ile Leu Asp Leu Ile Gln Thr Phe Val Glu Ser Leu Asp Arg Cys
            100                 105                 110 ttt act gaa gtc aat gaa ctt gat ttg att ttt aac tgg caa act ttg        384
Phe Thr Glu Val Asn Glu Leu Asp Leu Ile Phe Asn Trp Gln Thr Leu
                115                 120                 125 gaa agt gta tta gaa gaa atc gtg cag ggg ggc atg gtc att gaa aca        432
Glu Ser Val Leu Glu Glu Ile Val Gln Gly Gly Met Val Ile Glu Thr
        130                 135                 140 aat gtg aac aga ata gtt gct tct gtt gac gaa ctc aac aaa gct gcc        480
Asn Val Asn Arg Ile Val Ala Ser Val Asp Glu Leu Asn Lys Ala Ala
145                 150                 155                 160 gag tcc aca gat agt aaa att gga aga cta acg tcc act gga ttt gga        528
Glu Ser Thr Asp Ser Lys Ile Gly Arg Leu Thr Ser Thr Gly Phe Gly
                165                 170                 175 agc gca cta caa gcg ttt gct caa ggc gga ttt gca caa tgg gca acg        576
Ser Ala Leu Gln Ala Phe Ala Gln Gly Gly Phe Ala Gln Trp Ala Thr
            180                 185                 190 ggg caa taa                                                            585
Gly Gln <210> SEQ ID NO 68
<211> LENGTH: 194
<212> TYPE: PRT
<213> ORGANISM: Saccharomyces cerevisiae

<400> SEQUENCE: 68

Met Ile His Ala Val Leu Ile Phe Asn Lys Lys Cys Gln Pro Arg Leu
1               5                   10                  15

Val Lys Phe Tyr Thr Pro Val Asp Leu Pro Lys Gln Lys Leu Leu Leu
            20                  25                  30

Glu Gln Val Tyr Glu Leu Ile Ser Gln Arg Asn Ser Asp Phe Gln Ser
        35                  40                  45

Ser Phe Leu Val Thr Pro Pro Ser Leu Leu Leu Ser Asn Glu Asn Asn
    50                  55                  60

Asn Asp Glu Val Asn Asn Glu Asp Ile Gln Ile Ile Tyr Lys Asn Tyr
65                  70                  75                  80

Ala Thr Leu Tyr Phe Thr Phe Ile Val Asp Asp Gln Glu Ser Glu Leu
                85                  90                  95

Ala Ile Leu Asp Leu Ile Gln Thr Phe Val Glu Ser Leu Asp Arg Cys
            100                 105                 110

Phe Thr Glu Val Asn Glu Leu Asp Leu Ile Phe Asn Trp Gln Thr Leu
        115                 120                 125

Glu Ser Val Leu Glu Glu Ile Val Gln Gly Gly Met Val Ile Glu Thr
    130                 135                 140

Asn Val Asn Arg Ile Val Ala Ser Val Asp Glu Leu Asn Lys Ala Ala
145                 150                 155                 160

Glu Ser Thr Asp Ser Lys Ile Gly Arg Leu Thr Ser Thr Gly Phe Gly
                165                 170                 175

Ser Ala Leu Gln Ala Phe Ala Gln Gly Gly Phe Ala Gln Trp Ala Thr
            180                 185                 190

Gly Gln

<210> SEQ ID NO 69
<211> LENGTH: 570
<212> TYPE: DNA
```

<213> ORGANISM: Saccharomyces cerevisiae
<220> FEATURE:
<221> NAME/KEY: CDS
<222> LOCATION: (1)..(570)

<400> SEQUENCE: 69

| | | | | | | | | | | | | | | | | |
|---|---|---|---|---|---|---|---|---|---|---|---|---|---|---|---|---|
| atg | tct | tct | tta | tcg | cta | tat | act | gtt | cag | gct | gtt | tta | ata | cta | gat | 48 |
| Met | Ser | Ser | Leu | Ser | Leu | Tyr | Thr | Val | Gln | Ala | Val | Leu | Ile | Leu | Asp | |
| 1 | | | | 5 | | | | | 10 | | | | | 15 | | |
| cag | caa | gga | gaa | cga | att | tat | gca | aag | tat | tat | caa | cct | cct | cat | aga | 96 |
| Gln | Gln | Gly | Glu | Arg | Ile | Tyr | Ala | Lys | Tyr | Tyr | Gln | Pro | Pro | His | Arg | |
| | | | 20 | | | | | 25 | | | | | 30 | | | |
| tct | gat | gaa | gga | cac | caa | ttg | ctc | ttc | aat | tcg | gtg | aag | aag | caa | aaa | 144 |
| Ser | Asp | Glu | Gly | His | Gln | Leu | Leu | Phe | Asn | Ser | Val | Lys | Lys | Gln | Lys | |
| | | 35 | | | | | 40 | | | | | 45 | | | | |
| gag | ttt | gag | aaa | caa | cta | tac | cgt | aag | act | cac | aag | caa | gat | tcg | gag | 192 |
| Glu | Phe | Glu | Lys | Gln | Leu | Tyr | Arg | Lys | Thr | His | Lys | Gln | Asp | Ser | Glu | |
| | 50 | | | | | 55 | | | | | 60 | | | | | |
| att | tta | atc | ttc | gag | gat | cat | tta | gtc | ctt | tac | aaa | gaa | tac | att | gat | 240 |
| Ile | Leu | Ile | Phe | Glu | Asp | His | Leu | Val | Leu | Tyr | Lys | Glu | Tyr | Ile | Asp | |
| 65 | | | | | 70 | | | | | 75 | | | | | 80 | |
| atc | acg | ata | tat | tta | gtt | gct | tcg | ctg | gaa | gag | aat | gaa | att | gtt | ctt | 288 |
| Ile | Thr | Ile | Tyr | Leu | Val | Ala | Ser | Leu | Glu | Glu | Asn | Glu | Ile | Val | Leu | |
| | | | | 85 | | | | | 90 | | | | | 95 | | |
| cag | caa | gga | ttt | tca | gca | atc | aga | gga | gct | ttg | gat | ttg | att | ttg | aac | 336 |
| Gln | Gln | Gly | Phe | Ser | Ala | Ile | Arg | Gly | Ala | Leu | Asp | Leu | Ile | Leu | Asn | |
| | | | 100 | | | | | 105 | | | | | 110 | | | |
| tca | gga | atg | gac | aaa | aaa | aac | atc | caa | gaa | aac | tat | gat | atg | gtt | tta | 384 |
| Ser | Gly | Met | Asp | Lys | Lys | Asn | Ile | Gln | Glu | Asn | Tyr | Asp | Met | Val | Leu | |
| | | 115 | | | | | 120 | | | | | 125 | | | | |
| tta | gct | att | gat | gaa | acc | att | gat | aat | ggt | gtt | atc | ctc | gaa | act | gac | 432 |
| Leu | Ala | Ile | Asp | Glu | Thr | Ile | Asp | Asn | Gly | Val | Ile | Leu | Glu | Thr | Asp | |
| | 130 | | | | | 135 | | | | | 140 | | | | | |
| tct | aac | act | atc | gca | tcc | aga | gtt | tct | aaa | cca | cct | acg | aac | gaa | ccc | 480 |
| Ser | Asn | Thr | Ile | Ala | Ser | Arg | Val | Ser | Lys | Pro | Pro | Thr | Asn | Glu | Pro | |
| 145 | | | | | 150 | | | | | 155 | | | | | 160 | |
| caa | atg | gca | tta | gat | ttg | gat | aag | ggt | ttc | tta | ggc | gcg | tgg | ggt | ttc | 528 |
| Gln | Met | Ala | Leu | Asp | Leu | Asp | Lys | Gly | Phe | Leu | Gly | Ala | Trp | Gly | Phe | |
| | | | | 165 | | | | | 170 | | | | | 175 | | |
| gca | aag | agc | aag | ttt | caa | gaa | agg | tta | cag | caa | ggc | tta | tga | | | 570 |
| Ala | Lys | Ser | Lys | Phe | Gln | Glu | Arg | Leu | Gln | Gln | Gly | Leu | | | | |
| | | | 180 | | | | | 185 | | | | | | | | |

<210> SEQ ID NO 70
<211> LENGTH: 189
<212> TYPE: PRT
<213> ORGANISM: Saccharomyces cerevisiae

<400> SEQUENCE: 70

Met Ser Ser Leu Ser Leu Tyr Thr Val Gln Ala Val Leu Ile Leu Asp
1               5                   10                  15

Gln Gln Gly Glu Arg Ile Tyr Ala Lys Tyr Tyr Gln Pro Pro His Arg
            20                  25                  30

Ser Asp Glu Gly His Gln Leu Leu Phe Asn Ser Val Lys Lys Gln Lys
        35                  40                  45

Glu Phe Glu Lys Gln Leu Tyr Arg Lys Thr His Lys Gln Asp Ser Glu
    50                  55                  60

Ile Leu Ile Phe Glu Asp His Leu Val Leu Tyr Lys Glu Tyr Ile Asp
65                  70                  75                  80

Ile Thr Ile Tyr Leu Val Ala Ser Leu Glu Glu Asn Glu Ile Val Leu

```
                    85                  90                  95
Gln Gln Gly Phe Ser Ala Ile Arg Gly Ala Leu Asp Leu Ile Leu Asn
                100                 105                 110

Ser Gly Met Asp Lys Lys Asn Ile Gln Glu Asn Tyr Asp Met Val Leu
            115                 120                 125

Leu Ala Ile Asp Glu Thr Ile Asp Asn Gly Val Ile Leu Glu Thr Asp
    130                 135                 140

Ser Asn Thr Ile Ala Ser Arg Val Ser Lys Pro Pro Thr Asn Glu Pro
145                 150                 155                 160

Gln Met Ala Leu Asp Leu Asp Lys Gly Phe Leu Gly Ala Trp Gly Phe
                165                 170                 175

Ala Lys Ser Lys Phe Gln Glu Arg Leu Gln Gln Gly Leu
            180                 185
```

<210> SEQ ID NO 71
<211> LENGTH: 42
<212> TYPE: DNA
<213> ORGANISM: Artificial Sequence
<220> FEATURE:
<223> OTHER INFORMATION: synthetic DNA

<400> SEQUENCE: 71
tccccgggtg gtcagtccct tatgtctcct gattcttgtc ct              42

<210> SEQ ID NO 72
<211> LENGTH: 47
<212> TYPE: DNA
<213> ORGANISM: Artificial Sequence
<220> FEATURE:
<223> OTHER INFORMATION: synthetic DNA

<400> SEQUENCE: 72
ttgaacgatc ggggaaattc gagctctcat gtaagcagac ttcttgc         47

<210> SEQ ID NO 73
<211> LENGTH: 45
<212> TYPE: DNA
<213> ORGANISM: Artificial Sequence
<220> FEATURE:
<223> OTHER INFORMATION: synthetic DNA

<400> SEQUENCE: 73
ttggagagaa cacgggggac tctagaggat cccgggtggt cagtc           45

<210> SEQ ID NO 74
<211> LENGTH: 42
<212> TYPE: DNA
<213> ORGANISM: Artificial Sequence
<220> FEATURE:
<223> OTHER INFORMATION: synthetic DNA

<400> SEQUENCE: 74
tccccgggtg gtcagtccct tatggcaggg actaatgatt ct              42

<210> SEQ ID NO 75
<211> LENGTH: 47
<212> TYPE: DNA
<213> ORGANISM: Artificial Sequence
<220> FEATURE:
<223> OTHER INFORMATION: synthetic DNA

<400> SEQUENCE: 75
ttgaacgatc ggggaaattc gagctcttat gtaagaagac ttctcgc         47

<210> SEQ ID NO 76
<211> LENGTH: 45
<212> TYPE: DNA
<213> ORGANISM: Artificial Sequence
<220> FEATURE:
<223> OTHER INFORMATION: synthetic DNA

<400> SEQUENCE: 76
ttggagagaa cacgggggac tctagaggat cccgggtggt cagtc            45

<210> SEQ ID NO 77
<211> LENGTH: 21
<212> TYPE: DNA
<213> ORGANISM: Artificial Sequence
<220> FEATURE:
<223> OTHER INFORMATION: synthetic DNA

<400> SEQUENCE: 77
atgtctcctg attcttgtcc t            21

<210> SEQ ID NO 78
<211> LENGTH: 25
<212> TYPE: DNA
<213> ORGANISM: Artificial Sequence
<220> FEATURE:
<223> OTHER INFORMATION: synthetic DNA

<400> SEQUENCE: 78
cacctcatgt aagcagactt cttgc            25

<210> SEQ ID NO 79
<211> LENGTH: 21
<212> TYPE: DNA
<213> ORGANISM: Artificial Sequence
<220> FEATURE:
<223> OTHER INFORMATION: synthetic DNA

<400> SEQUENCE: 79
atggcaggga ctaatgattc t            21

<210> SEQ ID NO 80
<211> LENGTH: 25
<212> TYPE: DNA
<213> ORGANISM: Artificial Sequence
<220> FEATURE:
<223> OTHER INFORMATION: synthetic DNA

<400> SEQUENCE: 80
caccttatgt aagaagactt ctcgc            25

<210> SEQ ID NO 81
<211> LENGTH: 21
<212> TYPE: DNA
<213> ORGANISM: Artificial Sequence
<220> FEATURE:
<223> OTHER INFORMATION: synthetic DNA

<400> SEQUENCE: 81
ggaaagtagc aatgcaaagc g            21

<210> SEQ ID NO 82
<211> LENGTH: 24
<212> TYPE: DNA
<213> ORGANISM: Artificial Sequence
<220> FEATURE:

```
<223> OTHER INFORMATION: synthetic DNA

<400> SEQUENCE: 82
agatatggtt ggttacaagg gctt                                          24

<210> SEQ ID NO 83
<211> LENGTH: 23
<212> TYPE: DNA
<213> ORGANISM: Artificial Sequence
<220> FEATURE:
<223> OTHER INFORMATION: synthetic DNA

<400> SEQUENCE: 83
ttcttgaaac ggatccaaac gtc                                           23

<210> SEQ ID NO 84
<211> LENGTH: 21
<212> TYPE: DNA
<213> ORGANISM: Artificial Sequence
<220> FEATURE:
<223> OTHER INFORMATION: synthetic DNA

<400> SEQUENCE: 84
attgtgtcgc catgatggaa c                                             21

<210> SEQ ID NO 85
<211> LENGTH: 21
<212> TYPE: DNA
<213> ORGANISM: Artificial Sequence
<220> FEATURE:
<223> OTHER INFORMATION: synthetic DNA

<400> SEQUENCE: 85
tcacaatttc caaggtgctg c                                             21

<210> SEQ ID NO 86
<211> LENGTH: 20
<212> TYPE: DNA
<213> ORGANISM: Artificial Sequence
<220> FEATURE:
<223> OTHER INFORMATION: synthetic DNA

<400> SEQUENCE: 86
tcatctgggt ttggatccgt                                               20
```